(12) United States Patent
Bodhuri et al.

(10) Patent No.: US 10,301,322 B2
(45) Date of Patent: May 28, 2019

(54) PROCESSES FOR THE PREPARATION OF EDOXABAN AND INTERMEDIATES THEREOF

(71) Applicant: Apotex Inc., Toronto (CA)

(72) Inventors: Prabhudas Bodhuri, Brantford (CA); Avedis Karadeolian, Cambridge (CA); Eduardo Gustavo Cammisa, Markham (CA); Stuart P. Green, Mount Pleasant (CA); Melanie R. A. Green, Milton (CA); Alfredo Paul Ceccarelli, Brantford (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 15/850,882

(22) Filed: Dec. 21, 2017

(65) Prior Publication Data
US 2018/0179226 A1 Jun. 28, 2018

Related U.S. Application Data

(60) Provisional application No. 62/439,248, filed on Dec. 27, 2016.

(51) Int. Cl.
*C07D 513/04* (2006.01)
*C07C 271/36* (2006.01)
*C07F 7/08* (2006.01)

(52) U.S. Cl.
CPC .......... *C07D 513/04* (2013.01); *C07C 271/36* (2013.01); *C07F 7/0812* (2013.01); *C07C 2601/14* (2017.05)

(58) Field of Classification Search
CPC .................................................. C07D 513/04
USPC .......................................... 546/114; 514/301
See application file for complete search history.

(56) References Cited

U.S. PATENT DOCUMENTS

| | | | |
|---|---|---|---|
| 7,342,014 B2 * | 3/2008 | Ohta | C07D 209/42 514/252.04 |
| 7,365,205 B2 | 4/2008 | Ohta et al. | |
| 7,547,786 B2 | 6/2009 | Nagasawa et al. | |
| 8,357,808 B2 | 1/2013 | Koyama et al. | |
| 8,686,189 B2 | 4/2014 | Sato et al. | |
| 2012/0035369 A1 | 2/2012 | Kawanami | |
| 2016/0016974 A1 | 1/2016 | Nakamura et al. | |
| 2017/0050983 A1 | 2/2017 | Ueda | |

FOREIGN PATENT DOCUMENTS

| | | |
|---|---|---|
| CA | 2940001 A1 | 8/2015 |
| CN | 104761571 A | 7/2015 |
| CN | 105198776 A | 12/2015 |

OTHER PUBLICATIONS

Liu et al.; "Synthesis of a non-hydrolyzable estrone sulfate analogue bearing the difluoromethanesulfonamide group and its evaluation as a steroid sulfatase inhibitor"; Org. Biomol. Chem.; 2005; pp. 3329-3335; vol. 3.

Nagata et al.; "Stereoselective synthesis and biological evaluation of 3,4-diaminocyclohexanecarboxylic acid derivatives as factor Xa inhibitors"; Bioorganic & Medicinal Chemistry Letters; 2008; pp. 4587-4592; vol. 18.

Zheng et al.; "Au-Catalyzed Piperidine Synthesis via Tandem Acyloxy Migration/Intramolecular [3+2] Cycloaddition of Enynyl Esters"; Organic Letters; 2011; pp. 6448-6451; vol. 13:24.

* cited by examiner

*Primary Examiner* — Patricia L Morris
(74) *Attorney, Agent, or Firm* — The Webb Law Firm

(57) ABSTRACT

The present invention provides processes for the preparation of Edoxaban (1) and salts thereof, as well as intermediates thereof. In particular, intermediate compounds and/or salts of the Formulae (3), (4), (6-A), (7-A), (8-A), (9-A) and (10-AS) are provided.

3 Claims, No Drawings

PROCESSES FOR THE PREPARATION OF EDOXABAN AND INTERMEDIATES THEREOF

CROSS-REFERENCE TO RELATED APPLICATION

This application claims benefit of U.S. Provisional Patent Application No. 62/439,248, filed Dec. 27, 2016, the disclosure of which is hereby incorporated in its entirety by reference.

TECHNICAL FIELD

The present invention relates to processes for the preparation of Edoxaban and intermediates used in the preparation thereof.

BACKGROUND

Edoxaban tosylate monohydrate, an oral anti-coagulant, is marketed in the United States as SAVAYSA®, and is indicated to reduce the risk of stroke and systemic embolism (SE) in patients with nonvalvular atrial fibrillation (NVAF), and for the treatment of deep vein thrombosis (DVT) and pulmonary embolism (PE) following 5 to 10 days of initial therapy with a parenteral anticoagulant. Edoxaban (1) is a factor Xa ("FXa") inhibitor having the chemical name $N^1$-(5-chloro-2-pyridinyl)-$N^2$-[(1S,2R,4S)-4-[(dimethylamino)carbonyl]-2-[[(4,5,6,7-tetrahydro-5-methylthiazolo[5,4-c]pyridin-2-yl)carbonyl]amino]cyclohexyl]ethanediamide, and the following structural formula:

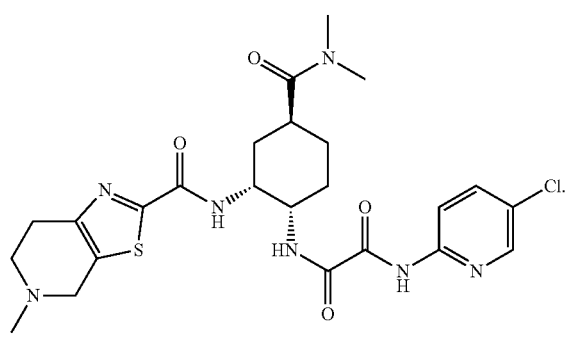

(1)

U.S. Pat. No. 7,365,205 B2 discloses preparation of Edoxaban (1) and salts thereof as a member of a class of diamine derivatives that inhibit FXa. Two routes for the preparation of Edoxaban, as shown in Schemes 1 and 2 below, are provided. However, the synthesis of intermediate (III) in either route requires the use of sodium azide as a nitrogen source for the introduction of the two cis-amino groups on the cyclohexyl ring. Sodium azide is a highly toxic reagent having deleterious effects on the environment, which poses safety concerns when used on an industrial scale. Additionally, following mesylation of intermediate (II), the azide displacement of the mesyloxy group to yield intermediate (III) produces as much as 10% to 15% of the undesired trans-isomer (III-B), which can carry through subsequent steps as an impurity if not removed. A discussion of the formation of this impurity is provided in Nagata et al. *Bioorg. Med. Chem. Lett.* 2008, 18(16), 4587-4592.

Scheme 1 (Prior Art)

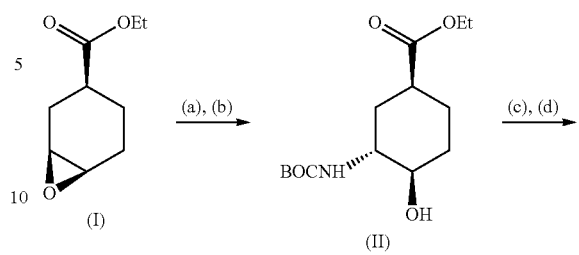

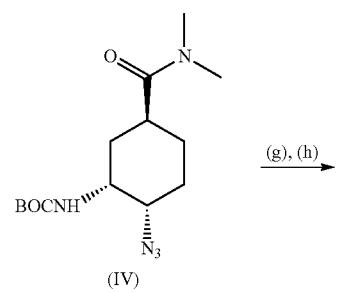

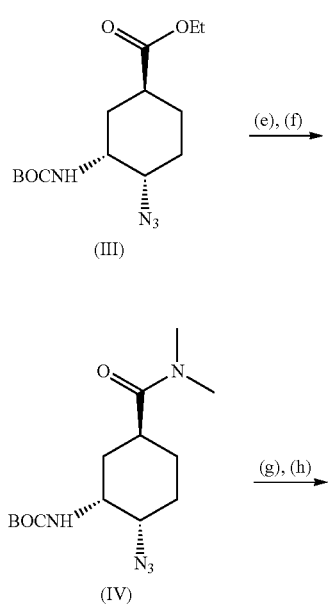

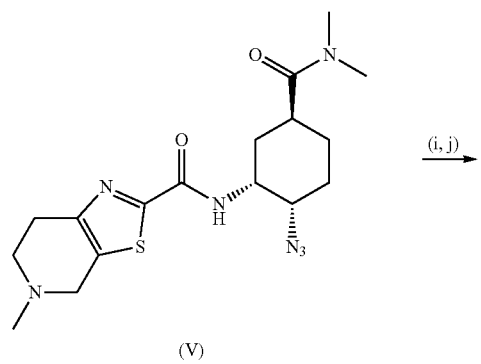

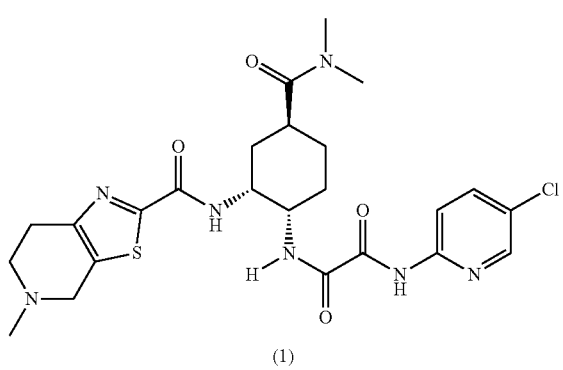

(1)

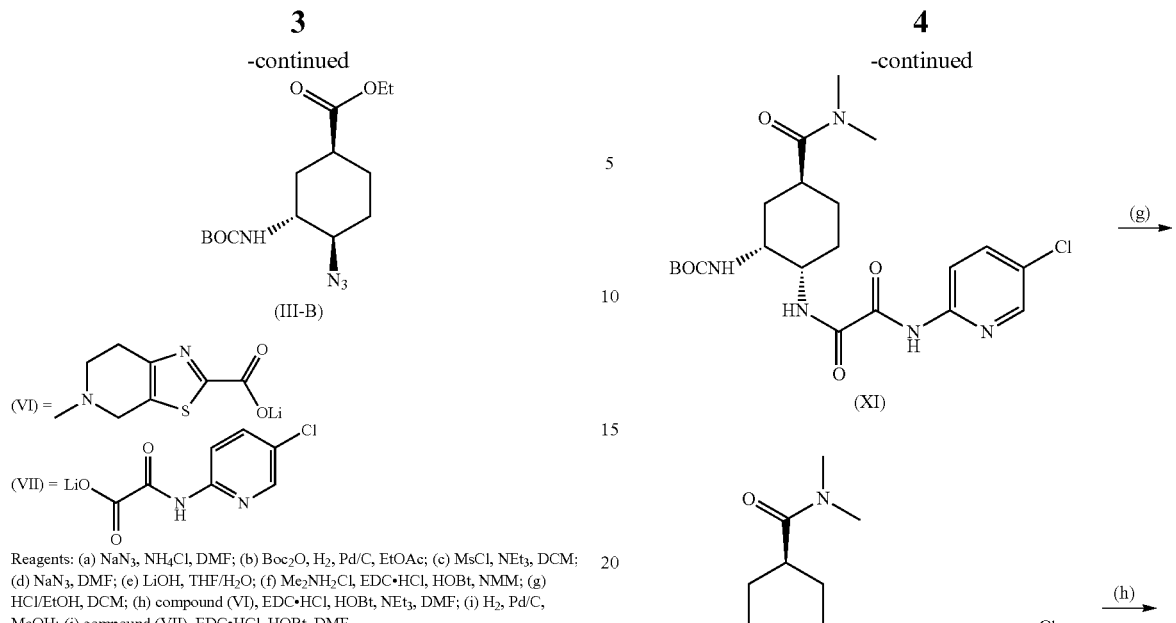

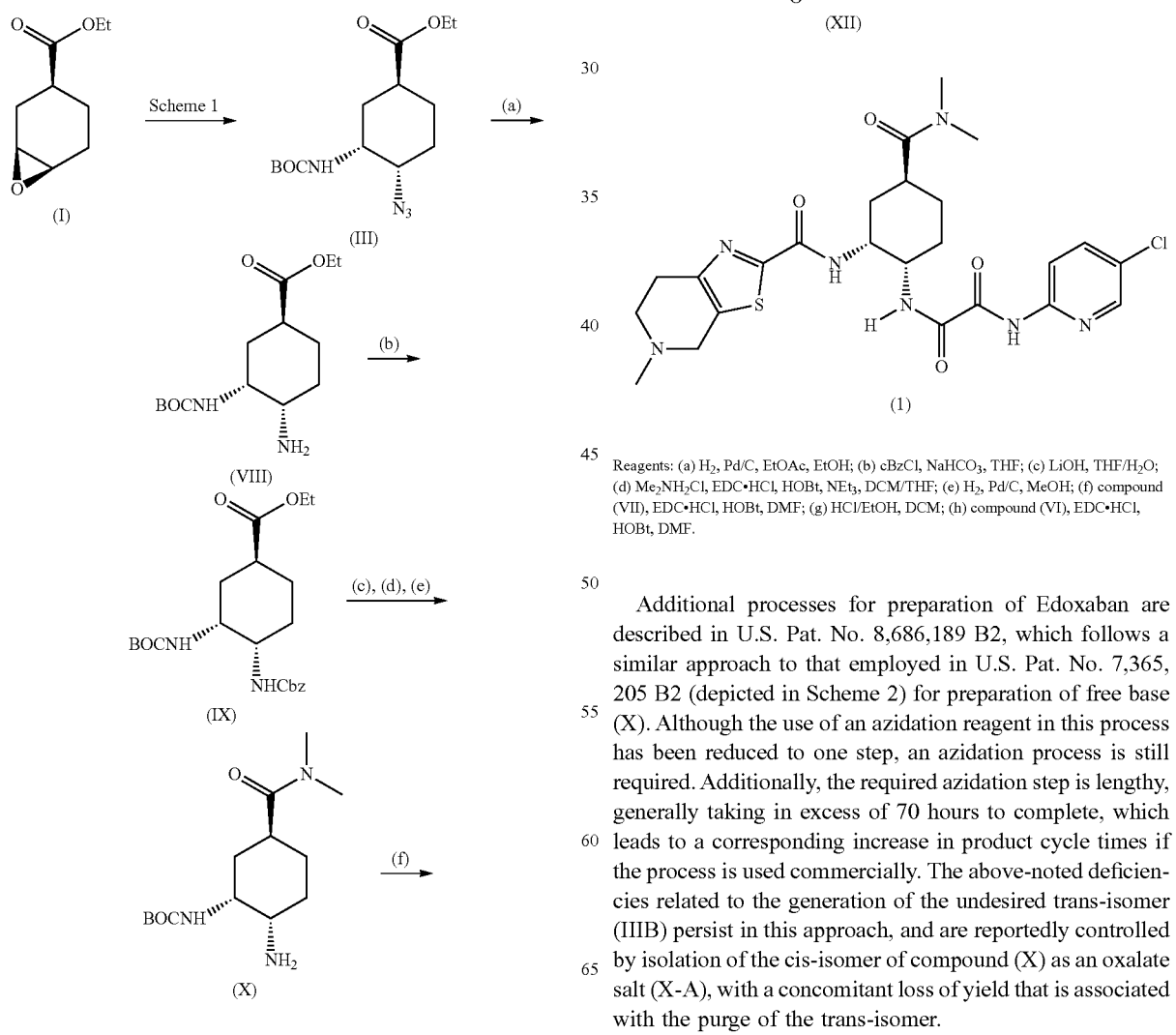

Reagents: (a) H₂, Pd/C, EtOAc, EtOH; (b) cBzCl, NaHCO₃, THF; (c) LiOH, THF/H₂O; (d) Me₂NH₂Cl, EDC•HCl, HOBt, NEt₃, DCM/THF; (e) H₂, Pd/C, MeOH; (f) compound (VII), EDC•HCl, HOBt, DMF; (g) HCl/EtOH, DCM; (h) compound (VI), EDC•HCl, HOBt, DMF.

Additional processes for preparation of Edoxaban are described in U.S. Pat. No. 8,686,189 B2, which follows a similar approach to that employed in U.S. Pat. No. 7,365,205 B2 (depicted in Scheme 2) for preparation of free base (X). Although the use of an azidation reagent in this process has been reduced to one step, an azidation process is still required. Additionally, the required azidation step is lengthy, generally taking in excess of 70 hours to complete, which leads to a corresponding increase in product cycle times if the process is used commercially. The above-noted deficiencies related to the generation of the undesired trans-isomer (IIIB) persist in this approach, and are reportedly controlled by isolation of the cis-isomer of compound (X) as an oxalate salt (X-A), with a concomitant loss of yield that is associated with the purge of the trans-isomer.

(X-A)

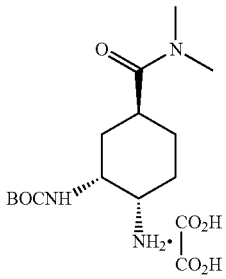

(X-A)

U.S. Pat. No. 8,357,808 B2 discloses conditions for the preparation of Edoxaban intermediate (XI) (see Scheme 2). In this process, the generation of 'Impurity X', which is formed during the subsequent reaction of oxalate salt (X-A), is reportedly minimized by controlling the order of addition of reaction components, and adding a tertiary amine in divided portions. However, this approach to impurity control can be operationally challenging to implement on an industrial scale.

'Impurity X'

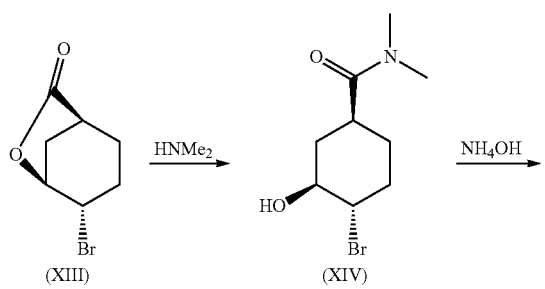

Further processes for the preparation of Edoxaban and/or intermediates thereof are disclosed in US 2012/0035369 A1, CA 2 940 001 A1, CN 104761571 A and CN 105198776 A. However, where these processes reference the use of the core cis-diamino cyclohexyl unit, it is prepared using azidation, which has the drawbacks noted above.

In US 2016/0016974 A1, a process is disclosed for preparation of Edoxaban and intermediates thereof where the cis-diamino groups on the cyclohexyl ring in compounds (XVIII) and (XIX) are introduced by an intramolecular cyclization substitution reaction as part of a multi-step process, as shown in Scheme 3.

Scheme 3 (Prior Art)

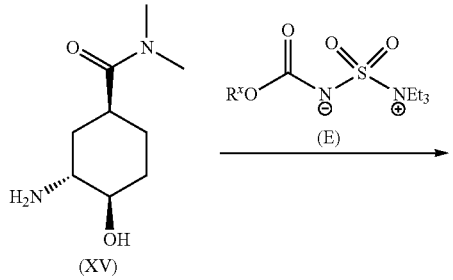

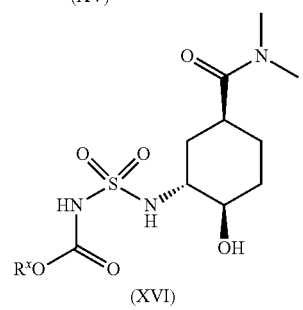

(XV)

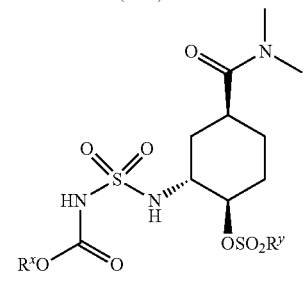

(XVI)

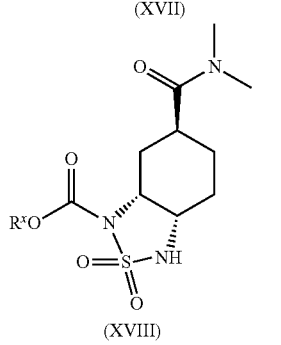

(XVII)

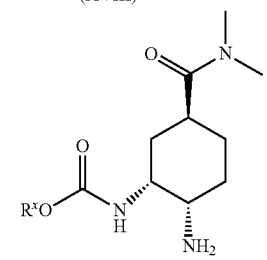

(XVIII)

(XIX)

$R^x$ = t-butyl, benzyl;
$R^y$ = methyl, 4-methylphenyl

In US 2016/0016974 A1, the treatment of intermediate (XVII) with base provides thiadiazole (XVIII), reportedly by progression through an aziridine intermediate and migration of the carbamate-protected nitrogen, which is said to control the stereo- and regio-chemistry of the two amino positions. The free amine position of compound (XIX) is further reacted with a chloropyridinyl amino(oxo)acetate moiety, followed by deprotection of the carbamate group and coupling with the tetrahydrothiazolo pyridine unit to yield Edoxaban. The cyclization/substitution steps provided in this route directs the carbamate protecting group $R^xCO_2$— to the position shown in compound (XIX) in Scheme 3. However, careful control of the subsequent coupling conditions using this intermediate is required to avoid generation of 'Impurity X'.

In view of the foregoing issues associated with the known process for the preparation of Edoxaban, there remains a need in the art for improved processes for use in the preparation of Edoxaban that reduce the number of steps involved, provide greater control of impurities, and reduce the need to use undesirable reagents.

SUMMARY

The present invention provides improved processes for the preparation of Edoxaban (1), as well as processes for the preparation of intermediates useful in the preparation of Edoxaban, as depicted in Scheme 4. The improved processes of the present invention provided herein avoid the use of azide reagents and provide a high degree of regio- and stereo-selectivity during introduction of the diamino groups at the 3- and 4-positions of the cyclohexyl ring in compound (4). Advantageously, the positioning of the carbamate protecting group of compound (4) in the process of the present invention simplifies the later introduction of the two ring units while also limiting the generation of 'Impurity X'. Intermediate compound (5) may be converted to Edoxaban (1) using the methods described herein.

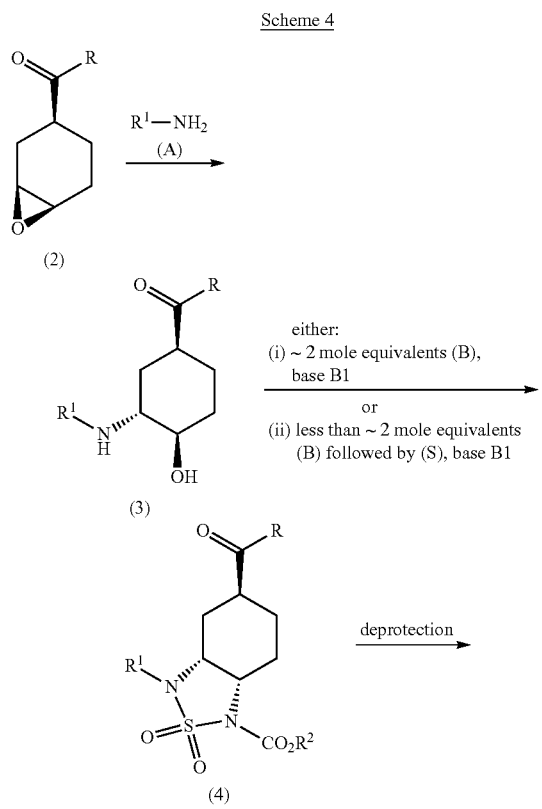

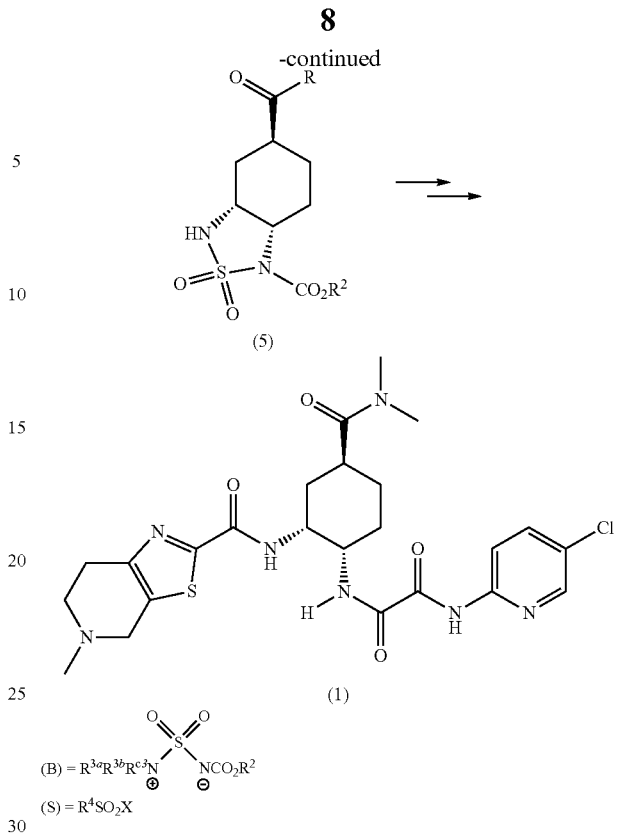

In Scheme 4 above:

R is selected from the group consisting of alkoxy, substituted alkoxy, aryloxy, substituted aryloxy, arylalkoxy, substituted arylalkoxy and dialkylamino;

$R^1$ is $CR^{1a}R^{1b}R^{1c}$;

$R^{1a}$, $R^{1b}$ and $R^{1c}$ are independently selected from the group consisting of H, alkyl, —C≡$CR^{1d}$, —$CR^{1e}$=$C(R^{1e})_2$, aryl and substituted aryl;

$R^{1d}$ is selected from the group consisting of H, alkyl, substituted alkyl, aryl, substituted aryl, arylalkyl, and substituted arylalkyl;

$R^{1e}$ is either (a) three independent groups selected from the group consisting of H, alkyl, substituted alkyl, aryl, substituted aryl, arylalkyl, and substituted arylalkyl or (b) two $R^{1e}$ taken together form a cyclic hydrocarbon ring with the carbon or carbons to which they are bonded, and the other $R^{1e}$ is selected from the group consisting of H, alkyl, substituted alkyl, aryl, substituted aryl, arylalkyl, and substituted arylalkyl;

at least one of $R^{1a}$, $R^{1b}$ and $R^{1c}$ is —C≡$CR^{1d}$, —$CR^{1e}$=C$(R^{1e})_2$, aryl or substituted aryl;

$R^2$ is selected from the group consisting of an aliphatic group, substituted aliphatic group, aryl, substituted aryl, arylalkyl, and substituted arylalkyl;

$R^{3a}$, $R^{3b}$ and $R^{3c}$ are either (a) three independent C1-C6 alkyl groups, (b) $R^{3a}$ is C1-C6 alkyl and $R^{3b}$ and $R^{3c}$ together form a saturated hetero monocyclic ring group with the N to which they are bonded or (c) $R^{3a}$, $R^{3b}$ and $R^{3c}$ together form a saturated hetero bicyclic ring group with the N to which they are bonded;

X is halogen or —$OSO_2R^5$; and $R^4$ and $R^5$ are independently selected from the group consisting of alkyl, substituted alkyl, phenyl and substituted phenyl.

Preferably, intermediate compound (5) is a compound of formula (5-A), and compound (5-A) is converted to Edoxaban (1) by the following process depicted in Scheme 5.

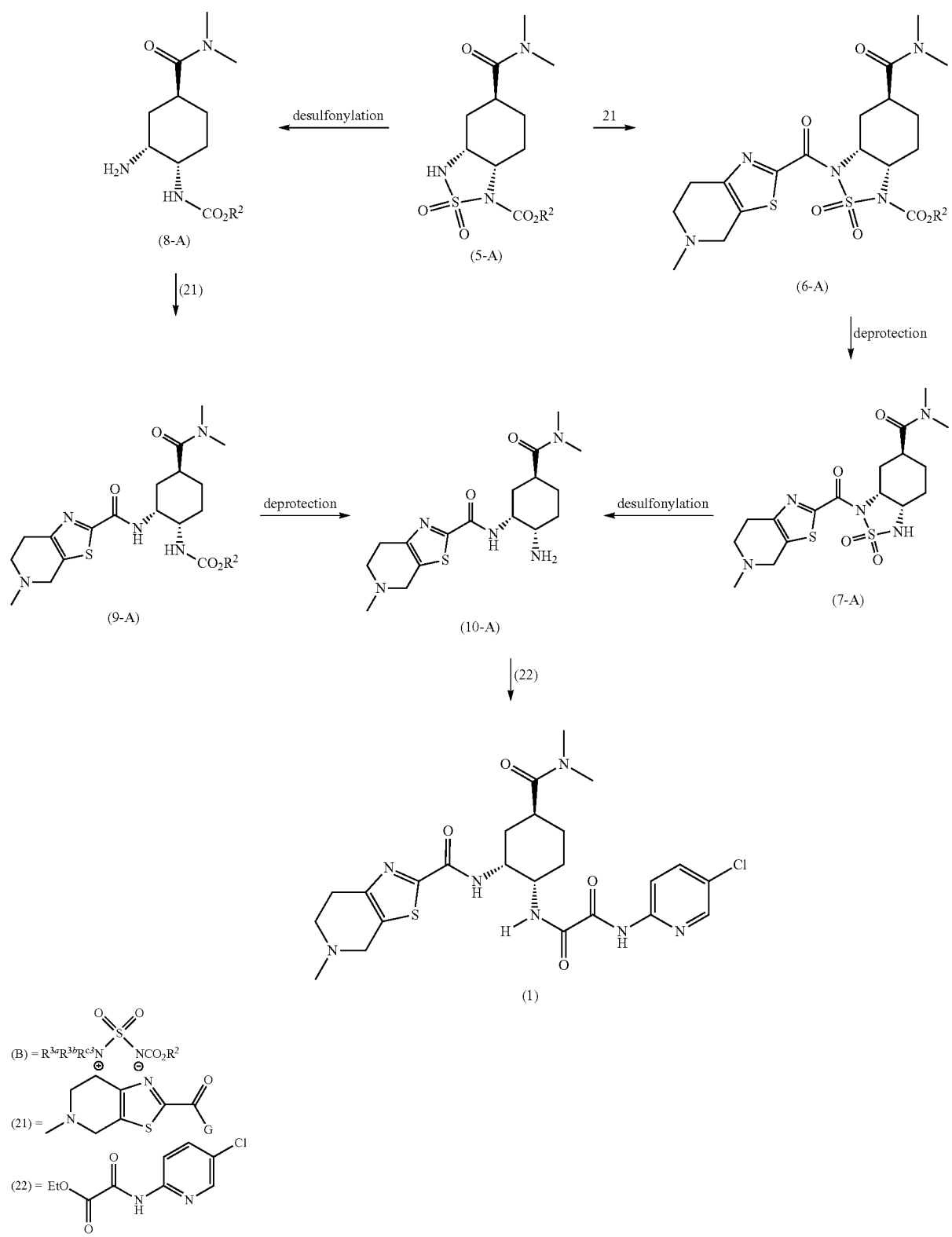
Scheme 5
When Edoxaban (1) is prepared from intermediate compound (5-A) according to this process, further advantages are afforded in the provision of novel intermediates, and salt forms thereof, that offer opportunities for isolation and purification, if desired. For example, in aspects of the invention, salts of embodiments of the intermediate compounds (3), (8) and (10) are more crystalline than the free forms, thereby providing a more convenient means for the isolation and purification of these intermediates.

Accordingly, in a first aspect of the present invention, there is provided a process for the preparation of a compound of Formula (3):

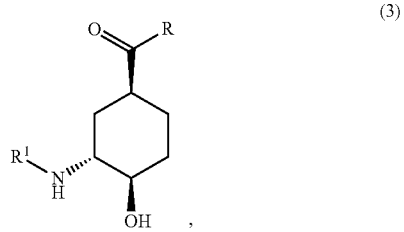
(3)

the process comprising reacting a compound of Formula (2):

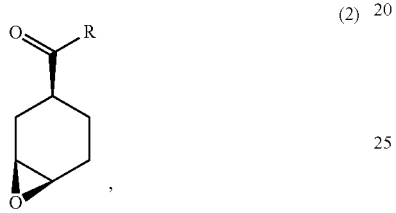
(2)

with a compound of Formula (20):

R$^1$—NH$_2$  (20), wherein
R is selected from the group consisting of alkoxy, substituted alkoxy, aryloxy, substituted aryloxy, arylalkoxy, substituted arylalkoxy and dialkylamino;
R$^1$ is CR$^{1a}$R$^{1b}$R$^{1c}$;
R$^{1a}$, R$^{1b}$ and R$^{1c}$ are independently selected from the group consisting of H, alkyl, —C≡CR$^{1d}$, —CR$^{1e}$=C(R$^{1e}$)$_2$, aryl and substituted aryl;
R$^{1d}$ is selected from the group consisting of H, alkyl, substituted alkyl, aryl, substituted aryl, arylalkyl, and substituted arylalkyl;
R$^{1e}$ is either (a) three independent groups selected from the group consisting of H, alkyl, substituted alkyl, aryl, substituted aryl, arylalkyl, and substituted arylalkyl or (b) two R$^{1e}$ taken together form a cyclic hydrocarbon ring with the carbon or carbons to which they are bonded, and the other R$^{1e}$ is selected from the group consisting of H, alkyl, substituted alkyl, aryl, substituted aryl, arylalkyl, and substituted arylalkyl; and
at least one of R$^{1a}$, R$^{1b}$ and R$^{1c}$ is —C≡CR$^{1d}$, —CR$^{1e}$=C(R$^{1e}$)$_2$, aryl or substituted aryl.

In a preferred embodiment of the first aspect, the compound of Formula (3) is further reacted with an acid of Formula HA to produce a salt of Formula (3-S):

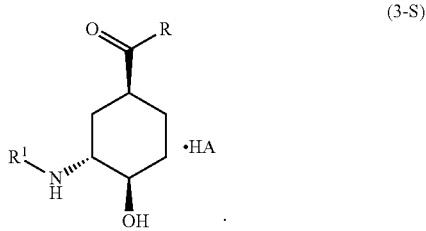
(3-S)

wherein the acid of Formula HA is an organic or inorganic acid. More preferably, the acid of Formula HA is selected from the group consisting of hydrogen bromide, hydrogen chloride, formic acid, acetic acid, oxalic acid, methanesulfonic acid, p-toluenesulfonic acid and camphorsulfonic acid. Most preferably, the acid of Formula HA is methanesulfonic acid.

In further independent preferred embodiments of the first aspect, R is dimethylamino; and R$^{1a}$, R$^{1b}$ and R$^{1c}$ are independently selected from the group consisting of H, aryl, and substituted aryl; and at least one of R$^{1a}$, R$^{1b}$ and R$^{1c}$ is aryl or substituted aryl. Preferably, R$^{1a}$ and R$^{1b}$ are both H; and R$^{1c}$ is phenyl.

In a second aspect of the present invention, there is provided a compound of Formula (3) or a salt thereof:

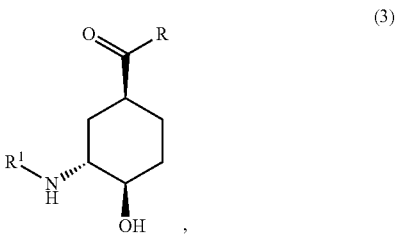
(3)

wherein
R is selected from the group consisting of alkoxy, substituted alkoxy, aryloxy, substituted aryloxy, arylalkoxy, substituted arylalkoxy and dialkylamino;
R$^1$ is CR$^{1a}$R$^{1b}$R$^{1c}$;
R$^{1a}$, R$^{1b}$ and R$^{1c}$ are independently selected from the group consisting of H, alkyl, —C≡CR$^{1d}$, —CR$^{1e}$=C(R$^{1e}$)$_2$, aryl and substituted aryl;
R$^{1d}$ is selected from the group consisting of H, alkyl, substituted alkyl, aryl, substituted aryl, arylalkyl, and substituted arylalkyl;
R$^{1e}$ is either (a) three independent groups selected from the group consisting of H, alkyl, substituted alkyl, aryl, substituted aryl, arylalkyl, and substituted arylalkyl or (b) two R$^{1e}$ taken together form a cyclic hydrocarbon ring with the carbon or carbons to which they are bonded, and the other R$^{1e}$ is selected from the group consisting of H, alkyl, substituted alkyl, aryl, substituted aryl, arylalkyl, and substituted arylalkyl; and
at least one of R$^{1a}$, R$^{1b}$ and R$^{1c}$ is —C≡CR$^{1d}$, —CR$^{1e}$=C (R$^{1e}$)$_2$, aryl or substituted aryl.

In a preferred embodiment of the second aspect, R is dimethylamino, R$^{1a}$ and R$^{1b}$ are both H, and R$^{1c}$ is phenyl or substituted phenyl.

In a further preferred embodiment of the second aspect the compound of Formula (3) is a salt of Formula (3-1AS):

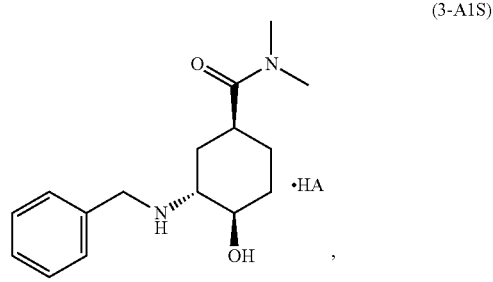
(3-A1S)

wherein HA is an organic or inorganic acid. Preferably, HA is selected from the group consisting of hydrogen halides, monocarboxylic acids, dicarboxylic acids, and sulfonic acids. More preferably, HA is selected from the group consisting of hydrogen bromide, hydrogen chloride, formic acid, acetic acid, oxalic acid, methanesulfonic acid, p-toluenesulfonic acid and camphorsulfonic acid.

In a third aspect of the present invention, there is provided a process for the preparation of a compound of Formula (4):

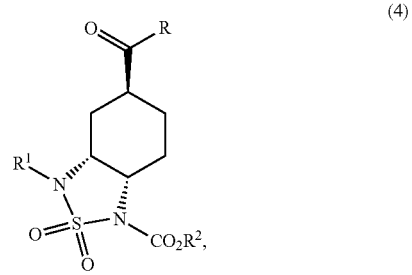

(4)

the process comprising reacting, a compound of Formula (3) or a salt thereof:

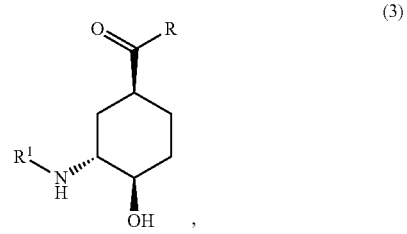

(3)

with a compound of Formula (B):

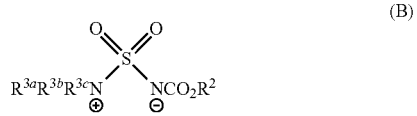

(B)

wherein

R is selected from the group consisting of alkoxy, substituted alkoxy, aryloxy, substituted aryloxy, arylalkoxy, substituted arylalkoxy and dialkylamino;

$R^1$ is $CR^{1a}R^{1b}R^{1c}$;

$R^{1a}$, $R^{1b}$ and $R^{1c}$ are independently selected from the group consisting of H, $-C \equiv CR^{1d}$, $-CR^{1e} = C(R^{1e})_2$, aryl and substituted aryl;

$R^{1d}$ is selected from the group consisting of H, alkyl, substituted alkyl, aryl, substituted aryl, arylalkyl, and substituted arylalkyl;

$R^{1e}$ is either (a) three independent groups selected from the group consisting of H, alkyl, substituted alkyl, aryl, substituted aryl, arylalkyl, and substituted arylalkyl or (b) two $R^{1e}$ taken together form a cyclic hydrocarbon ring with the carbon or carbons to which they are bonded, and the other $R^{1e}$ is selected from the group consisting of H, alkyl, substituted alkyl, aryl, substituted aryl, arylalkyl, and substituted arylalkyl;

at least one of $R^{1a}$, $R^{1b}$ and $R^{1c}$ is $-C \equiv CR^{1d}$, $-CR^{1e} = C(R^{1e})_2$, aryl or substituted aryl;

$R^2$ is selected from the group consisting of an aliphatic group, substituted aliphatic group, aryl, substituted aryl, arylalkyl, and substituted arylalkyl; and $R^{3a}$, $R^{3b}$ and $R^{3c}$ are either (a) three independent C1-C6 alkyl groups, (b) $R^{3a}$ is C1-C6 alkyl and $R^{3b}$ and $R^{3c}$ together form a saturated hetero monocyclic ring group with the N to which they are bonded or (c) $R^{3a}$, $R^{3b}$ and $R^{3c}$ together form a saturated hetero bicyclic ring group with the N to which they are bonded.

In a preferred embodiment of the third aspect, $R^{3a}$, $R^{3b}$ and $R^{3c}$ are three independent C1-C6 alkyl groups. Preferably, each of $R^{3a}$, $R^{3b}$ and $R^{3c}$ is ethyl.

In another preferred embodiment of the third aspect, an amount of at least about 2 mole equivalents of the compound of Formula (B) with respect to the compound of Formula (3) is used. Preferably, the compound of Formula (3) is first reacted with less than about 2 mole equivalents of a compound of Formula (B) with respect to a compound of Formula (3) to form an intermediate compound, and the compound of Formula (4) is produced by further reacting the intermediate compound with a sulfonylating agent (S):

$$R^4SO_2X \quad\quad (S)$$

wherein X is halogen or $-OSO_2R^5$; and $R^4$ and $R^5$ are independently selected from the group consisting of alkyl, substituted alkyl, phenyl and substituted phenyl.

In a further preferred embodiment of the third aspect, the compound of Formula (B) is prepared in situ by reacting together chlorosulfonylisocyanate, $R^2OH$ and $NR^{3a}R^{3b}R^{3c}$, wherein $R^2$ is selected from the group consisting of an aliphatic group, substituted aliphatic group, aryl, substituted aryl, arylalkyl, and substituted arylalkyl; and $R^{3a}$, $R^{3b}$ and $R^{3c}$ are either (a) three independent C1-C6 alkyl groups, (b) $R^{3a}$ is C1-C6 alkyl and $R^{3b}$ and $R^{3c}$ together form a saturated hetero monocyclic ring group with the N to which they are bonded or (c) $R^{3a}$, $R^{3b}$ and $R^{3c}$ together form a saturated hetero bicyclic ring group with the N to which they are bonded. Preferably, $R^{3a}$, $R^{3b}$ and $R^{3c}$ are three independent C1-C6 alkyl groups. More preferably, each of $R^{3a}$, $R^{3b}$ and $R^{3c}$ is ethyl.

In another preferred embodiment of the third aspect, the compound of Formula (3) is a salt of Formula (3-S):

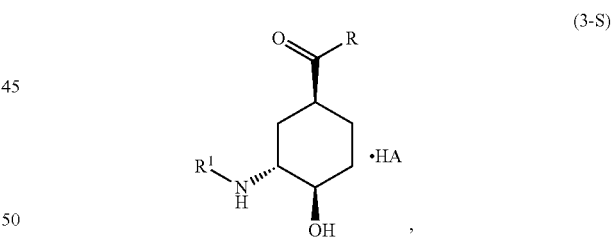

(3-S)

wherein HA is an organic or inorganic acid. Preferably, HA is selected from the group consisting of hydrogen bromide, hydrogen chloride, formic acid, acetic acid, oxalic acid, methanesulfonic acid, p-toluenesulfonic acid and camphorsulfonic acid. More preferably, HA is methanesulfonic acid.

In further independent preferred embodiments of the third aspect, R is dimethylamino; and $R^{1a}$, $R^{1b}$ and $R^{1c}$ are independently selected from the group consisting of H, aryl, and substituted aryl; and at least one of $R^{1a}$, $R^{1b}$ and $R^{1c}$ is aryl or substituted aryl. Preferably, $R^{1a}$ and $R^{1b}$ are both H; and $R^{1c}$ is phenyl. In a further preferred embodiment of the third aspect, $R^{1a}$, $R^{1b}$ and $R^{1c}$ are independently selected from the group consisting of H, aryl, and substituted aryl; and at least one of $R^{1a}$, $R^{1b}$ and $R^{1c}$ is aryl or substituted aryl; and $R^2$ is an aliphatic group or a substituted aliphatic group. Preferably, $R^{1a}$ and $R^{1b}$ are both H; $R^{1c}$ is phenyl; and $R^2$ is selected from the group consisting of t-butyl, 2-methyl-2-hexanyl, 1-methylcyclohexyl and 2-trimethylsilylethyl.

In a fourth aspect of the present invention, there is provided a compound of Formula (4):

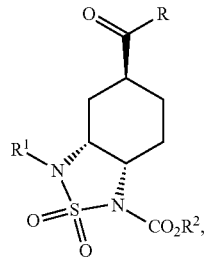

(4)

wherein

R is selected from the group consisting of alkoxy, substituted alkoxy, aryloxy, substituted aryloxy, arylalkoxy, substituted arylalkoxy and dialkylamino;

$R^1$ is $CR^{1a}R^{1b}R^{1c}$;

$R^{1a}$, $R^{1b}$ and $R^{1c}$ are independently selected from the group consisting of H, alkyl, —C≡$CR^{1d}$, —$CR^{1e}$=$C(R^{1e})_2$, aryl and substituted aryl;

$R^{1d}$ is selected from the group consisting of H, alkyl, substituted alkyl, aryl, substituted aryl, arylalkyl, and substituted arylalkyl;

$R^{1e}$ is either (a) three independent groups selected from the group consisting of H, alkyl, substituted alkyl, aryl, substituted aryl, arylalkyl, and substituted arylalkyl or (b) two $R^{1e}$ taken together form a cyclic hydrocarbon ring with the carbon or carbons to which they are bonded, and the other $R^{1e}$ is selected from the group consisting of H, alkyl, substituted alkyl, aryl, substituted aryl, arylalkyl, and substituted arylalkyl;

at least one of $R^{1a}$, $R^{1b}$ and $R^{1c}$ is —C≡$CR^d$, —$CR^{1e}$=C$(R^{1e})_2$, aryl or substituted aryl; and $R^2$ is selected from the group consisting of an aliphatic group, substituted aliphatic group, aryl, substituted aryl, arylalkyl, and substituted arylalkyl.

In a preferred embodiment of the fourth aspect, R is dimethylamino; $R^{1a}$, $R^{1b}$ and $R^{1c}$ are independently selected from the group consisting of H, aryl, and substituted aryl; at least one of $R^{1a}$, $R^{1b}$ and $R^{1c}$ is aryl or substituted aryl; and $R^2$ is an aliphatic group or a substituted aliphatic group. More preferably, R is dimethylamino; $R^{1a}$ and $R^{1b}$ are both H; $R^{1c}$ is phenyl; and $R^2$ is an aliphatic group or a substituted aliphatic group. Most preferably, R is dimethylamino; $R^{1a}$ and $R^{1b}$ are both H; $R^{1c}$ is phenyl; and $R^2$ is selected from the group consisting of t-butyl, 2-methyl-2-hexanyl, 1-methylcyclohexyl and 2-trimethylsilylethyl.

In a fifth embodiment of the present invention, there is provided a process for the preparation of a compound of Formula (5):

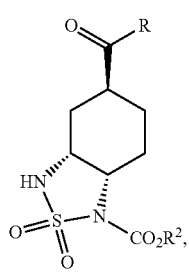

(5)

the process comprising deprotecting a compound of Formula (4):

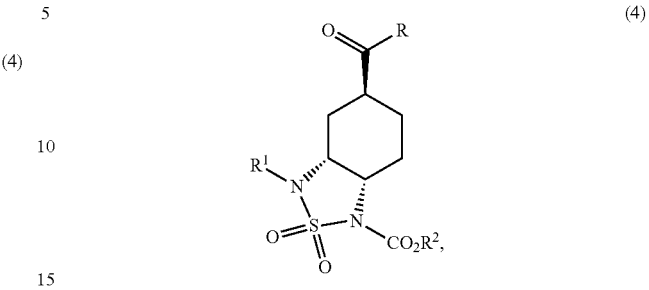

wherein

R is selected from the group consisting of alkoxy, substituted alkoxy, aryloxy, substituted aryloxy, arylalkoxy, substituted arylalkoxy and dialkylamino;

$R^1$ is $CR^{1a}R^{1b}R^{1c}$;

$R^{1a}$, $R^{1b}$ and $R^{1c}$ are independently selected from the group consisting of H, alkyl, —C≡$CR^{1d}$, —$CR^{1e}$=$C(R^{1e})_2$, aryl and substituted aryl;

$R^{1d}$ is selected from the group consisting of H, alkyl, substituted alkyl, aryl, substituted aryl, arylalkyl, and substituted arylalkyl;

$R^{1e}$ is either (a) three independent groups selected from the group consisting of H, alkyl, substituted alkyl, aryl, substituted aryl, arylalkyl, and substituted arylalkyl or (b) two $R^{1e}$ taken together form a cyclic hydrocarbon ring with the carbon or carbons to which they are bonded, and the other $R^{1e}$ is selected from the group consisting of H, alkyl, substituted alkyl, aryl, substituted aryl, arylalkyl, and substituted arylalkyl;

at least one of $R^{1a}$, $R^{1b}$ and $R^{1c}$ is —C≡$CR^{1d}$, —$CR^{1e}$=C$(R^{1e})_2$, aryl or substituted aryl; and $R^2$ is selected from the group consisting of aliphatic group, substituted aliphatic group, aryl, substituted aryl, arylalkyl, and substituted arylalkyl.

In a preferred embodiment of the fifth aspect, the deprotection of the compound of Formula (4) occurs by hydrogenolysis. Preferably, the hydrogenolysis is conducted in the presence of a hydrogen source and palladium catalyst selected from the group consisting of palladium on carbon and palladium hydroxide on carbon. Preferably, the hydrogen source is sodium formate or a salt thereof, and the process is conducted in a C1-C3 alcohol as solvent.

In further independent preferred embodiments of the fifth aspect, R is dimethylamino; and $R^{1a}$, $R^{1b}$ and $R^{1c}$ are independently selected from the group consisting of H, aryl, and substituted aryl; and at least one of $R^{1a}$, $R^{1b}$ and $R^{1c}$ is aryl or substituted aryl. Preferably, $R^{1a}$ and $R^{1b}$ are both H; and $R^{1c}$ is phenyl. In a further preferred embodiment of the third aspect, $R^{1a}$, $R^{1b}$ and $R^{1c}$ are independently selected from the group consisting of H, aryl, and substituted aryl; and at least one of $R^{1a}$, $R^{1b}$ and $R^{1c}$ is aryl or substituted aryl; and $R^2$ is an aliphatic group or a substituted aliphatic group. Preferably, $R^{1a}$ and $R^{1b}$ are both H; $R^{1c}$ is phenyl; and $R^2$ is selected from the group consisting of t-butyl, 2-methyl-2-hexanyl, 1-methylcyclohexyl and 2-trimethylsilylethyl.

In a sixth aspect of the invention, there is provided a process for the preparation of a compound of Formula (1), or a salt thereof:

(1)

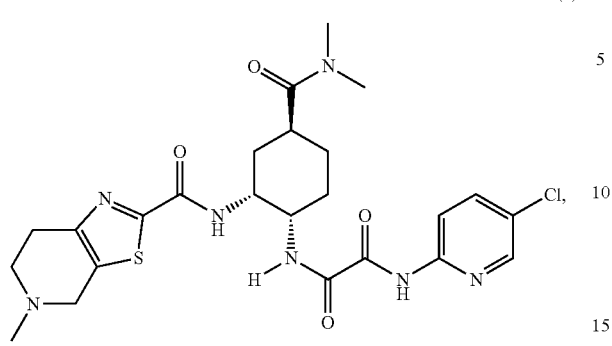

the process comprising:

(a) reacting a compound of Formula (5-A):

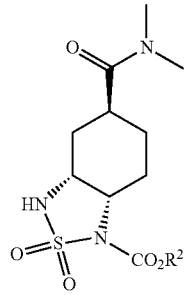

(5-A)

with a compound of Formula (21) or a salt thereof:

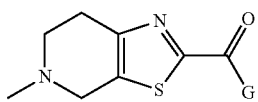

(21)

in the presence of a base B2 and, optionally in the presence of a coupling agent, to produce a compound of Formula (6-A):

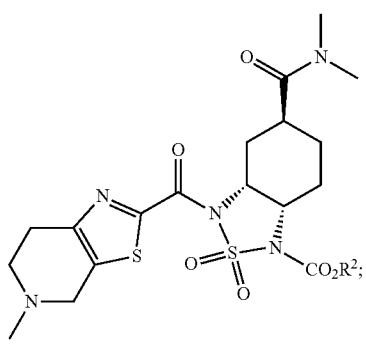

(6-A)

(b) deprotecting a compound of Formula (6-A) to produce a compound of Formula (7-A):

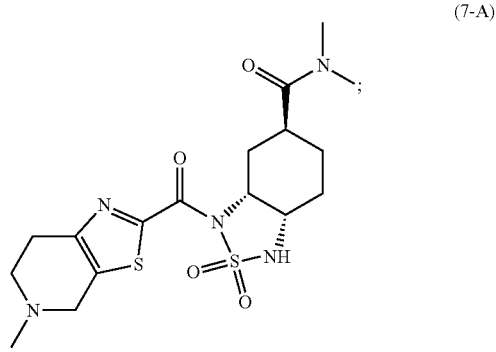

(7-A)

(c) desulfonylating a compound of Formula (7-A) to produce a compound of Formula (10-A):

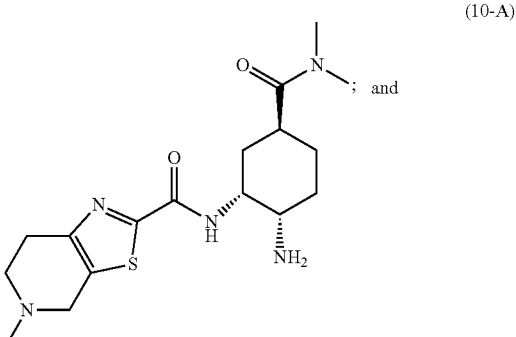

(10-A)

(d) reacting, in the presence of a base B3, a compound of Formula (10-A) or a salt thereof with a compound of Formula (22) or a salt thereof:

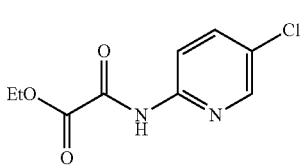

(22)

wherein

G is selected from the group consisting of OH, halide and $OR^6$;

$R^2$ is selected from the group consisting of an aliphatic group, substituted aliphatic group, aryl, substituted aryl, arylalkyl, and substituted arylalkyl;

$R^6$ is selected from the group consisting of an aliphatic group, substituted aliphatic group, aryl, substituted aryl, arylalkyl, and substituted arylalkyl;

the base B2 is selected from the group consisting of tertiary amines, metal carbonates and metal bicarbonates; and the base B3 is selected from the group consisting of organic and inorganic bases.

In a preferred embodiment of the sixth aspect, G in the compound of Formula (21) is halide. Preferably, in the preferred embodiment of the sixth aspect, a hydrogen halide salt of the compound of Formula (21) is used.

In a further preferred embodiment of the sixth aspect, $R^2$ is an aliphatic group or a substituted aliphatic group. Preferably, $R^2$ is selected from the group consisting of t-butyl, 2-methyl-2-hexanyl, 1-methylcyclohexyl and 2-trimethylsilylethyl.

In another preferred embodiment of the sixth aspect, the deprotection of the compound of Formula (6-A) occurs in the presence of trifluoroacetic acid. In a yet further preferred embodiment of the sixth aspect, the desulfonylation of the compound of Formula (7-A) occurs in the presence of pyridine. In a still yet further preferred embodiment of the sixth aspect, a hydrogen chloride salt of the compound of Formula (22) is used.

In another preferred embodiment of the sixth aspect, the compound of Formula (10-A) is further reacted with an acid HA to produce a salt of Formula (10-AS):

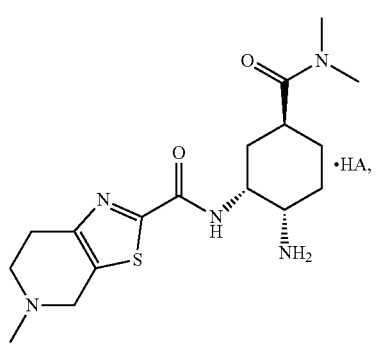

(10-AS)

wherein HA is an organic or inorganic acid. Preferably, HA is a sulfonic acid. More preferably, HA is camphorsulfonic acid. Most preferably, HA is (R)-camphorsulfonic acid.

In a seventh aspect of the present invention, there is provided a process for the preparation of a compound of Formula (10-A) or a salt thereof:

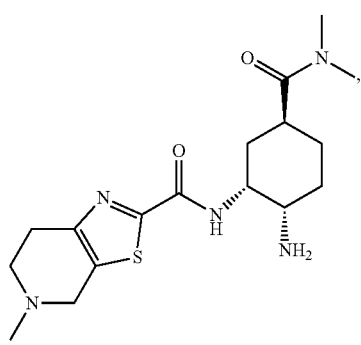

(10-A)

the process comprising desulfonylating a compound of Formula (7-A):

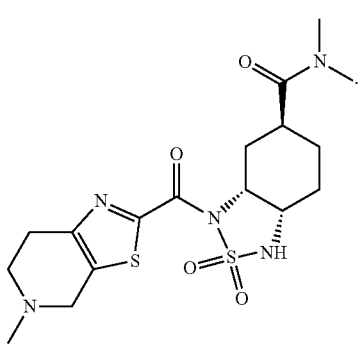

(7-A)

In a preferred embodiment of the seventh aspect, the desulfonylation of the compound of Formula (7-A) occurs in the presence of an aqueous base. Preferably, the aqueous base is aqueous pyridine.

In an eighth aspect of the present invention, there is provided a compound of Formula (6-A):

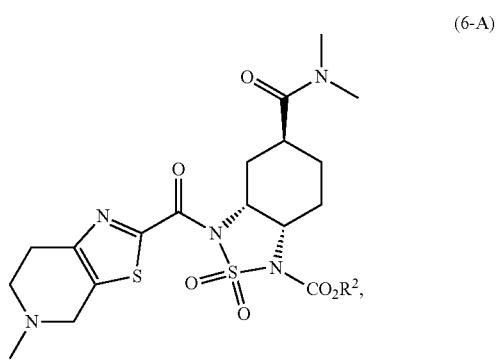

(6-A)

wherein $R^2$ is selected from the group consisting of an aliphatic group, substituted aliphatic group, aryl, substituted aryl, arylalkyl, and substituted arylalkyl. In a preferred embodiment of the eighth aspect, $R^2$ is an aliphatic group or a substituted aliphatic group. Preferably, $R^2$ is selected from the group consisting of t-butyl, 2-methyl-2-hexanyl, 1-methylcyclohexyl and 2-trimethylsilylethyl.

In a ninth aspect of the present invention, there is provided a compound of Formula (7-A):

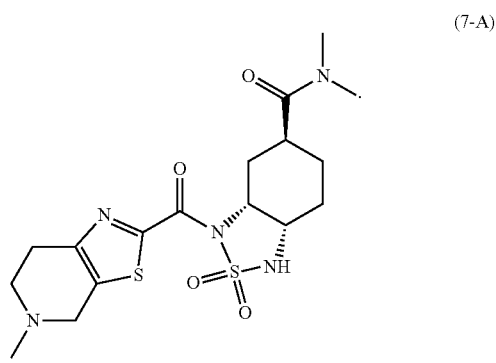

(7-A)

In a tenth aspect of the present invention, there is provided a process for the preparation of a compound of Formula (1) or a salt thereof:

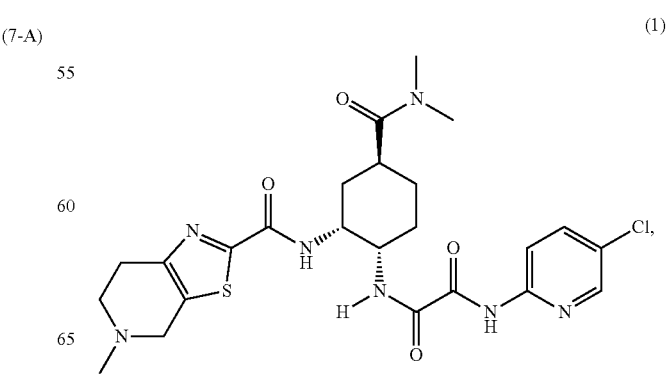

(1)

the process comprising:

(a) deprotecting a compound of Formula (4-A):

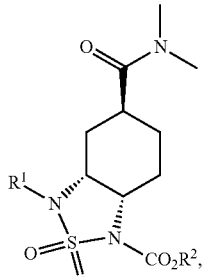
(4-A)

to produce a compound of Formula (5-A):

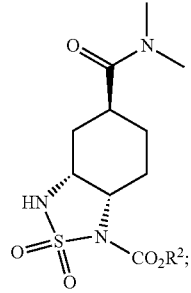
(5-A)

(b) desulfonylating a compound of Formula (5-A) to produce a compound of Formula (8-A):

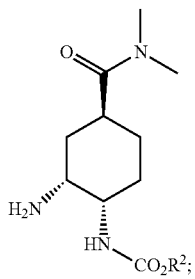
(8-A)

(c) reacting a compound of Formula (8-A) or a salt thereof with a compound of Formula (21) or a salt thereof:

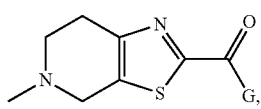
(21)

in the presence of a base B4 and, optionally in the presence of a coupling agent, to produce a compound of Formula (9-A):

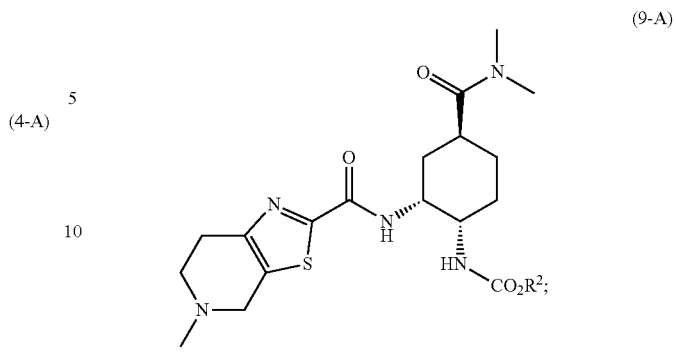
(9-A)

(d) deprotecting a compound of Formula (9-A) to produce a compound of Formula (10-A):

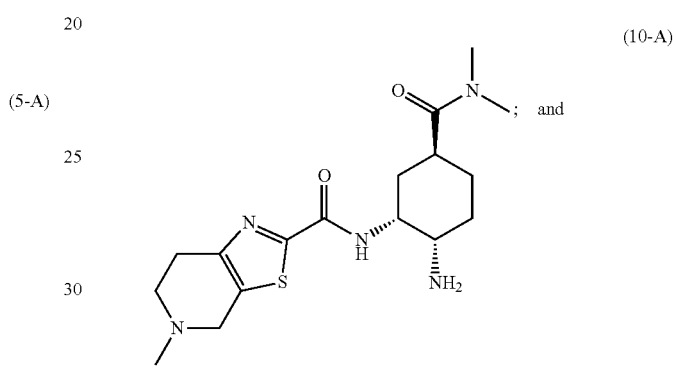
(10-A)

and (e) reacting, in the presence of a base B3, a compound of Formula (10-A) or a salt thereof with a compound of Formula (22) or a salt thereof:

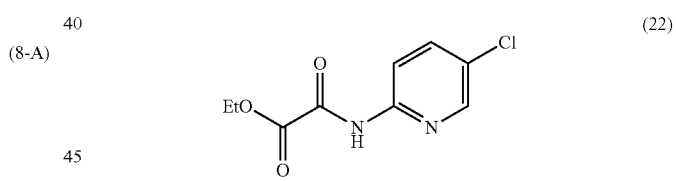
(22)

wherein
G is selected from the group consisting of OH, halide and $OR^6$;

$R^1$ is $CR^{1a}R^{1b}R^{1c}$;

$R^{1a}$, $R^{1b}$ and $R^{1c}$ are independently selected from the group consisting of H, alkyl, —C≡$CR^{1d}$, —$CR^{1e}$=$C(R^{1e})_2$, aryl and substituted aryl;

$R^{1d}$ is selected from the group consisting of H, alkyl, substituted alkyl, aryl, substituted aryl, arylalkyl, and substituted arylalkyl;

$R^{1e}$ is either (a) three independent groups selected from the group consisting of H, alkyl, substituted alkyl, aryl, substituted aryl, arylalkyl, and substituted arylalkyl or (b) two $R^{1e}$ taken together form a cyclic hydrocarbon ring with the carbon or carbons to which they are bonded, and the other $R^{1e}$ is selected from the group consisting of H, alkyl, substituted alkyl, aryl, substituted aryl, arylalkyl, and substituted arylalkyl;

at least one of $R^{1a}$, $R^{1b}$ and $R^{1c}$ is —C≡$CR^{1d}$, —$CR^{1e}$=$C(R^{1e})_2$, aryl or substituted aryl;

$R^2$ is selected from the group consisting of an aliphatic group, substituted aliphatic group, aryl, substituted aryl, arylalkyl, and substituted arylalkyl; and $R^6$ is selected from the group consisting of an aliphatic group, substituted aliphatic group, aryl, substituted aryl, arylalkyl, and substituted arylalkyl.

In a preferred embodiment of the tenth aspect, the deprotection in step (a) occurs by hydrogenolysis. Preferably, the hydrogenolysis is conducted in the presence of a hydrogen source and a palladium catalyst selected from the group consisting of palladium on carbon and palladium hydroxide on carbon. Preferably, the hydrogen source is sodium formate.

In a further preferred embodiment of the tenth aspect, step (b) is conducted without isolation of the compound of Formula (5-A) in step (a). In yet another preferred embodiment of the tenth aspect, the desulfonylation in step (b) occurs in the presence of pyridine.

In a further preferred embodiment of the tenth aspect, the compound of Formula (8-A) is further reacted with an acid HA to produce a salt of Formula (8-AS):

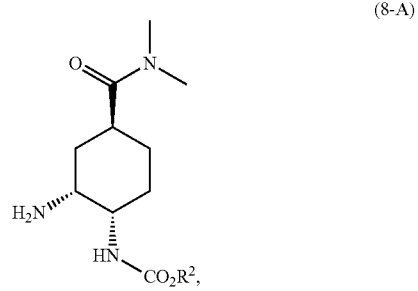
(8-A)

wherein $R^2$ is selected from the group consisting of a C5-C10 aliphatic group, substituted aliphatic group, aryl, substituted aryl, arylalkyl, and substituted arylalkyl. In a preferred embodiment of the eleventh aspect, $R^2$ is an aliphatic group or a substituted aliphatic group. Preferably, the compounds of formula (8-A) is a compound selected from the group consisting of:

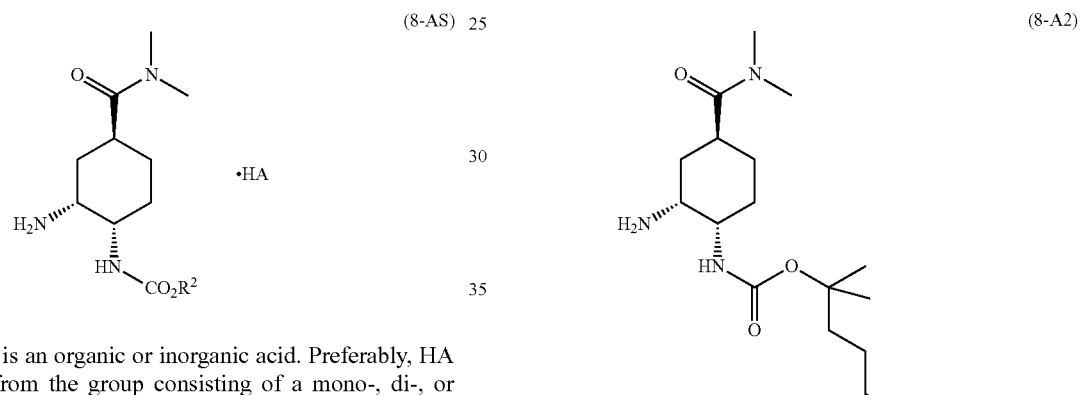

wherein HA is an organic or inorganic acid. Preferably, HA is selected from the group consisting of a mono-, di-, or tricarboxylic acid, a mineral acid and a sulfonic acid. More preferably, HA is selected from the group consisting of sulfuric acid, benzoic acid, tartaric acid, citric acid, camphorsulfonic acid and p-toluenesulfonic acid.

In another preferred embodiment of the tenth aspect, G in the compound of Formula (21) is OH and the reaction in step (c) occurs in the presence of a coupling agent which is N-(3-dimethylaminopropyl)-N'-ethylcarbodiimide hydrochloride/1-hydroxybenzo triazole.

In further independent preferred embodiments of the tenth aspect, the deprotection in step (d) occurs in the presence of acid; step (e) is conducted without isolation of the compound of Formula (10-A) or a salt thereof in step (d); a hydrogen halide salt of the compound of Formula (22) is used. R is dimethylamino; and $R^{1a}$, $R^{1b}$ and $R^{1c}$ are independently selected from the group consisting of H, aryl, and substituted aryl; and at least one of $R^{1a}$, $R^{1b}$ and $R^{1c}$ is aryl or substituted aryl. Preferably, $R^{1a}$ and $R^{1b}$ are both H; and $R^{1c}$ is phenyl. In a further preferred embodiment of the third aspect, $R^{1a}$, $R^{1b}$ and $R^{1c}$ are independently selected from the group consisting of H, aryl, and substituted aryl; and at least one of $R^{1a}$, $R^{1b}$ and $R^{1c}$ is aryl or substituted aryl; and $R^2$ is an aliphatic group or a substituted aliphatic group. Preferably, $R^{1a}$ and $R^{1b}$ are both H; $R^{1c}$ is phenyl; and $R^2$ is selected from the group consisting of t-butyl, 2-methyl-2-hexanyl, 1-methylcyclohexyl and 2-trimethylsilylethyl.

In an eleventh aspect of the present invention, there is provided a compound of Formula (8-A) or a salt thereof:

or a salt thereof.

In a further preferred embodiment of the eleventh aspect, the compound of Formula (8-A) is a salt of Formula (8-A4S):

(8-A4S)

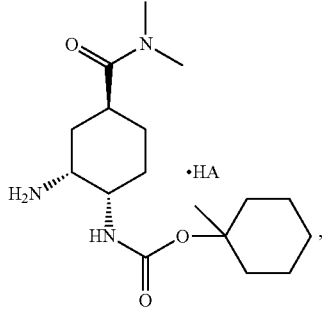

wherein HA is an organic or inorganic acid. Preferably, HA is selected from the group consisting of a mono-, di-, and tricarboxylic acids, mineral acids and sulfonic acid. More preferably, HA is selected from the group consisting of sulfuric acid, benzoic acid, tartaric acid, citric acid, camphorsulfonic acid and p-toluenesulfonic acid.

In a twelfth aspect of the present invention, there is provided a compound of Formula (9-A):

(9-A)

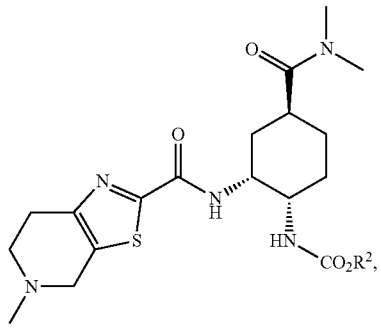

wherein $R^2$ is selected from the group consisting of an aliphatic group, substituted aliphatic group, aryl, substituted aryl, arylalkyl, and substituted arylalkyl. In a preferred embodiment of the twelfth aspect, $R^2$ is an aliphatic group or a substituted aliphatic group. Preferably, the compound of Formula (9-A) is a compound selected from the group consisting of:

(9-A2)

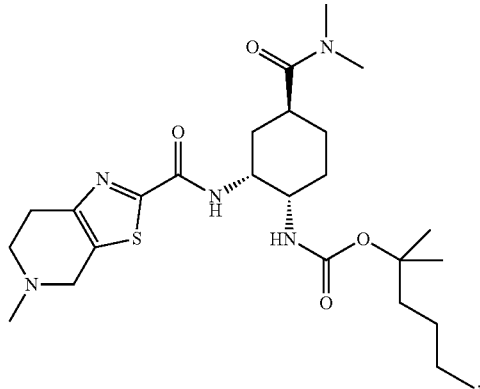

(9-A3)

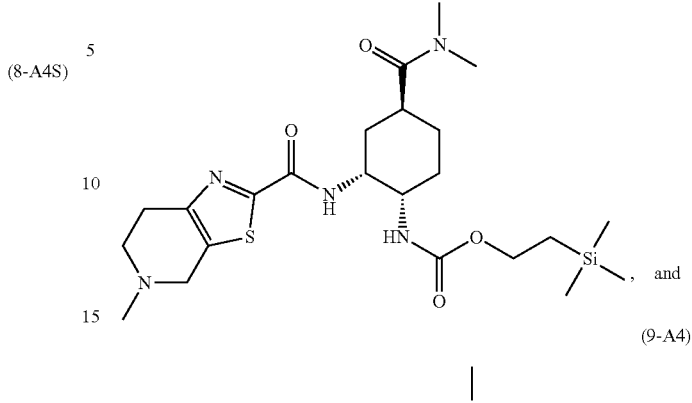

, and (9-A4)

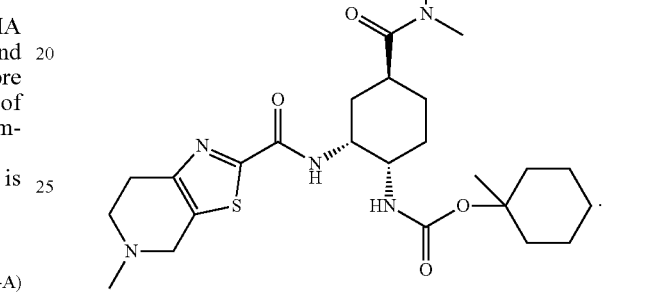

In a thirteenth aspect of the present invention, there is provided a salt of Formula (10-AS):

(10-AS)

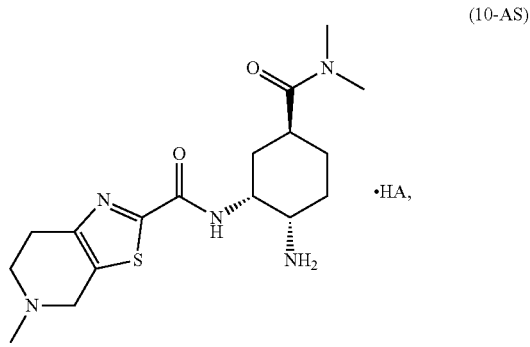 [SMILES: CN1CCc2nc(C(=O)N[C@@H]3C[C@@H](C(=O)N(C)C)CC[C@@H]3N)sc2C1]

wherein HA is an organic or inorganic acid. In a preferred embodiment of the thirteenth aspect, HA is a mono-, di-, or tricarboxylic acid, a mineral acid or a sulfonic acid. Preferably, HA is camphorsulfonic acid. More preferably, HA is (R)-camphorsulfonic acid.

DETAILED DESCRIPTION

Development of the processes provided herein followed from the discovery of the inventors that treatment of a suitably substituted amino alcohol (3) with an ammonium-sulfonyl carbamate Burgess-type reagent provides a thiadiazole (4) wherein the position of the nitrogen bearing the carbamate protecting group is reversed in relation to comparable processes. Based on this discovery, the present invention provides improved processes for the preparation of Edoxaban (1), as well as processes for the preparation of intermediates useful in the preparation of Edoxaban. The improved processes of the present invention provided herein avoid the use of azide reagents and provide a high degree of regio- and stereo-selectivity during introduction of the diamino groups at the 3- and 4-positions of the cyclohexyl ring in compound (4).

Advantageously, the positioning of the carbamate protecting group of compound (4) in the process of the present invention simplifies the later introduction of the two ring units while also limiting the generation of 'Impurity X'.

As used herein, the designation C1-Cx refers to the total number of carbon atoms in the indicated group, including substituent groups, with C1-Cx including C1-C2, C1-C3 . . . C1-Cx. For example, a group designated as "C1-C4" indicates that there are one to four carbon atoms in the moiety, i.e., groups containing 1 carbon atom, 2 carbon atoms, 3 carbon atoms or 4 carbon atoms. Thus, by way of example only, "C1-C4 alkyl" indicates that there are one to four carbon atoms in the alkyl group, i.e. the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

As used herein, the term "aliphatic", alone or as part of another substituent, means, unless otherwise stated, a straight chain, branched chain or cyclic hydrocarbon radical, or a combination thereof, which may be fully saturated, or mono- or polyunsaturated, and can include di- and multivalent radicals, having the number of carbon atoms designated. Examples of saturated hydrocarbon radicals include, but are not limited to, groups such as methyl, ethyl, n-propyl, iso-propyl, n-butyl, t-butyl, iso-butyl, sec-butyl, hexanyl, 2-methyl-2-hexanyl, cyclohexyl, 1-methylcyclohexyl, cyclopropylmethyl, and isomers of, for example, n-pentyl, n-hexyl, n-heptyl, n-octyl, and the like. An unsaturated hydrocarbon radical is one having one or more double bonds or triple bonds. Examples of unsaturated hydrocarbon radicals include, but are not limited to, vinyl, 2-propenyl, crotyl, 2-isopentenyl, 2-(butadienyl), 2,4-pentadienyl, 3-(1,4-pentadienyl), ethynyl, 1-propynyl, 2-propynyl, 3-butynyl, and the higher homologs and isomers.

As used herein, the term "alkyl", alone or as part of another substituent, means, unless otherwise stated, a straight or branched chain, saturated hydrocarbon radical having the number of carbon atoms designated (e.g. C1-C4 means one to four carbon atoms). When there is no indication of the number of carbon atoms in the alkyl, it is meant, unless otherwise indicated by context, that there are from 1 to 10 carbons. Examples of saturated hydrocarbon groups include methyl, ethyl, n-propyl, iso-propyl, n-butyl, t-butyl, iso-butyl and sec-butyl.

As used herein, the term "aryl", alone or as part of another substituent, means, unless otherwise stated, a polyunsaturated, aromatic, hydrocarbon radical which can be a single ring or multiple rings (preferably from 1 to 3 rings) which are fused together or linked covalently having the number of carbon atoms designated. When there is no indication of the number of carbon atoms in the aryl, it is meant, unless otherwise indicated by context, that there are from 6 to 18 carbons. Non-limiting examples of aryl groups include: phenyl, 1-naphthyl, 2-naphthyl and 4-biphenyl.

As used herein, the term "arylalkyl", alone or as part of another substituent, means, unless otherwise stated, an aryl substituent as defined herein attached through an alkyl radical to the parent structure. When there is no indication of the number of carbon atoms in the arylalkyl group, it is meant, unless otherwise indicated by context, that there are from 7 to 20 carbons. Non-limiting examples of arylalkyl groups include benzyl, and phenethyl.

As used herein, the term "heteroaryl" refers to an aryl radical that contains from one to four heteroatoms selected from N, O, and S, wherein the nitrogen and sulfur atoms are optionally oxidized, and the nitrogen atom(s) are optionally quaternized. A heteroaryl group can optionally be attached to the remainder of the molecule through a heteroatom. Non-limiting examples of heteroaryl groups include: 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

As used herein, the terms "alkoxy" or "alkoxy group", alone or as part of another substituent, means, unless otherwise stated, a radical of the formula AlkO- wherein Alk is an alkyl group as defined above. This term is exemplified by groups such as methoxy, ethoxy, propoxy, isopropoxy, butoxy, sec-butoxy, tert-butoxy, pentoxy, and the like.

As used herein, the terms "aryloxy" or "aryloxy group", alone or as part of another substituent, means, unless otherwise stated, a radical of the formula ArO—, wherein Ar is aryl as defined above. This term is exemplified by groups such as phenoxy, naphthoxy, and the like.

As used herein, the term "saturated hetero monocyclic ring group", alone or as part of another substituent, means, unless otherwise stated, a saturated monocyclic ring having the number of carbon atoms designated that contains from one to four heteroatoms selected from N, O, and S. When there is no indication of the number of carbon atoms in the ring, it is meant, unless otherwise indicated by context, that there are from 1 to 10 carbons. Examples of saturated hetero monocyclic ring group include pyrrolidine, morpholine and piperidine.

As used herein, the term "saturated hetero bicyclic ring group", alone or as part of another substituent, means, unless otherwise stated, a group having two rings that are either fused together across a bond between two atoms or a joined by a bridge across a series of atoms. When there is no indication of the number of carbon atoms in the ring, it is meant, unless otherwise indicated by context, that there are from 1 to 10 carbons. Examples of saturated hetero bicyclic ring group include 1,4-diazabicyclo[2.2.2]octane and quinuclidine.

As used herein, the term "substituted" refers to the replacement of one or more hydrogen atoms with any one of a variety of substituents. A substituent may be a non-hydrogen atom or multiple atoms of which at least one is a non-hydrogen atom and one or more may or may not be hydrogen atoms. A substituted group (e.g., substituted —$CH_2CH_3$) may be fully substituted (e.g. —$CF_2CF_3$), mono-substituted (e.g. —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc.). Substituted compounds may comprise substituents selected from the group consisting of: R''', OR'', NR''R''', SR'', halogen, SiR'''R'''R''', OCOR''', COR'', $CO_2$R'', CONR''R''', NR''$CO_2$R''', NR''COR''', SOR''', $SO_2$R''', CN, $NO_2$ and $CF_3$. As used herein, each R'' may be selected, independently, from the group consisting of hydrogen, an aliphatic group, aryl and arylalkyl. As used herein, each R''' may be selected, independently, from the group consisting of an aliphatic group, aryl and arylalkyl. An example of a substituted aliphatic group (e.g., substituted ethyl) includes 2-trimethylsilylethyl. Examples of substituent groups on substituted aliphatic groups include trialkylsilyl such as trimethylsilyl. Examples of substituent groups on substituted aryls include methoxy, methyl, nitro, and chloro.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

As used herein, wt % or % w/w refers to weight percent and is used to express weight solute/weight solution as a percentage.

As used herein, the term "volumes" refers to the parts of solvent or liquids by volume (mL) with respect to the weight of solute (g). For example, when a reaction is conducted using 1 g of starting material and 100 mL of solvent, it is said that 100 volumes of solvent are used.

As used herein, "room temperature" generally refers to a temperature of 20-25° C.

As used herein, the term "coupling reagent" or "coupling agent" refers to a compound that aids in bringing about a reaction to couple one compound to another compound.

As used herein, the term "about" means "close to" and that variation from the exact value that follows the term is within amounts that a person of skill in the art would understand to be reasonable. For example, when the term "about" is used with respect to temperature, a variation of ±5° C. is generally acceptable when carrying out the processes of the present invention; when used with respect to mole equivalents, a variation of ±0.1 moles is generally acceptable; and when used with respect to volumes, a variation of 10% is generally acceptable.

In preferred embodiments of the present invention, Edoxaban (1) and the intermediates thereof may be prepared by exemplary processes as set out in Scheme 6. Exemplary reagents and conditions for these reactions are disclosed herein.

Scheme 6

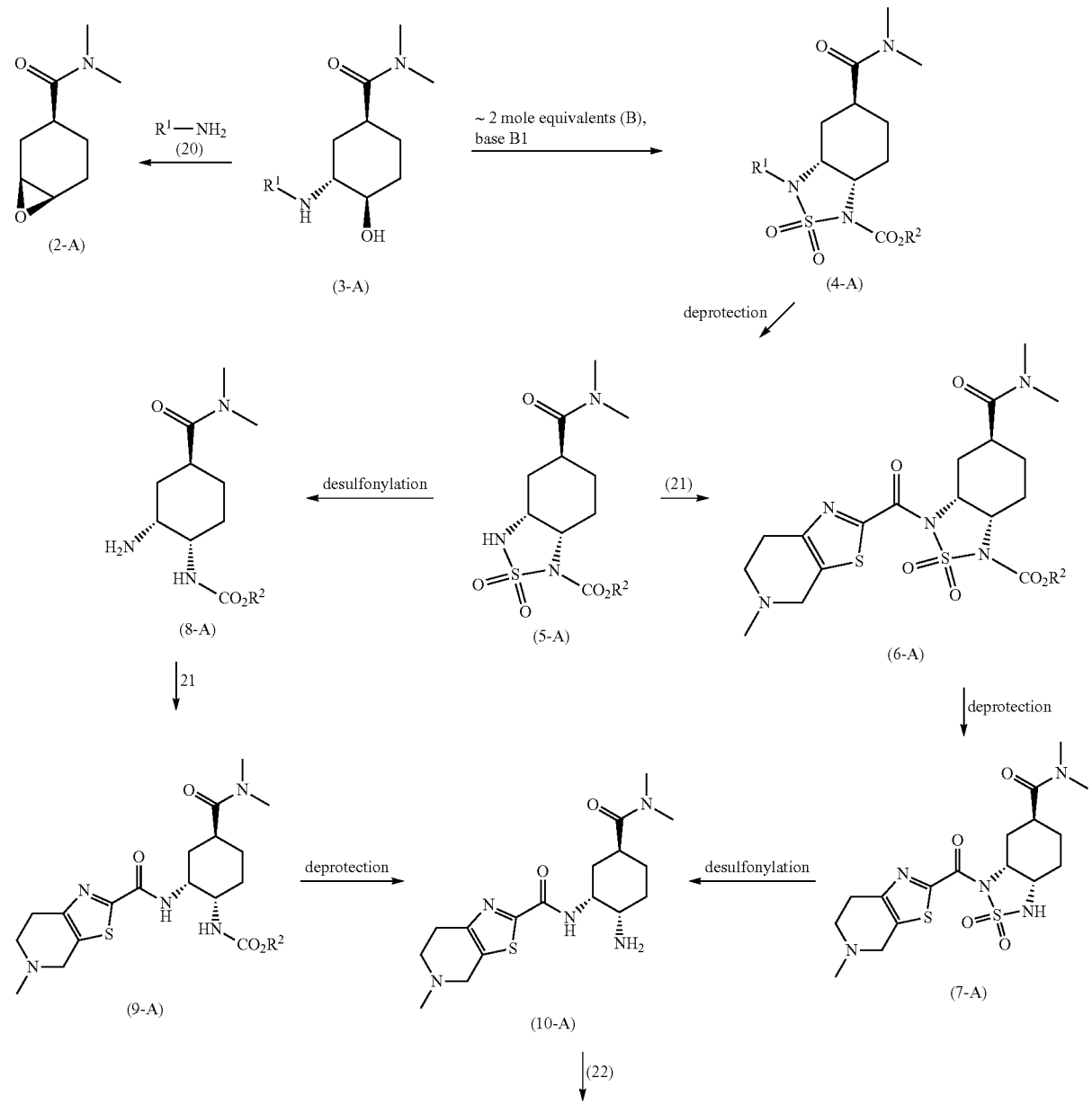

-continued

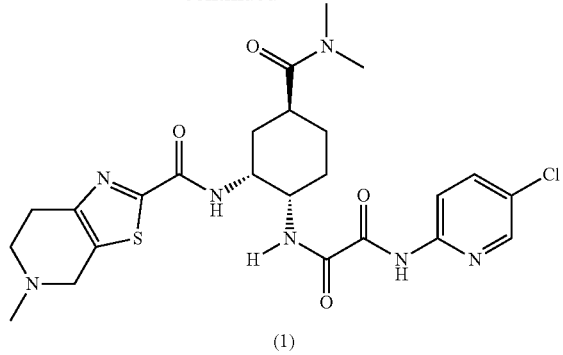

(1)

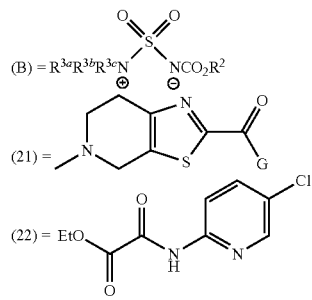

In Scheme 6 above, $R^1$ is $CR^{1a}R^{1b}R^{1c}$;

$R^{1a}$, $R^{1b}$ and $R^{1c}$ are independently selected from the group consisting of H, alkyl, —C≡$CR^{1d}$, —$CR^{1e}$=$C(R^{1e})_2$, aryl and substituted aryl;

$R^{1d}$ is H, alkyl, substituted alkyl, aryl, substituted aryl, arylalkyl, and substituted arylalkyl;

$R^{1e}$ is either (a) three independent groups selected from the group consisting of H, alkyl, substituted alkyl, aryl, substituted aryl, arylalkyl, and substituted arylalkyl or (b) two $R^{1e}$ taken together form a cyclic hydrocarbon ring with the carbon or carbons to which they are bonded, and the other $R^{1e}$ is selected from the group consisting of H, alkyl, substituted alkyl, aryl, substituted aryl, arylalkyl, and substituted arylalkyl;

at least one of $R^{1a}$, $R^{1b}$ and $R^{1c}$ is —C≡$CR^{1d}$, —$CR^{1e}$=$C(R^{1e})_2$, aryl or substituted aryl;

$R^2$ is selected from the group consisting of an aliphatic group, substituted aliphatic group, aryl, substituted aryl, arylalkyl, and substituted arylalkyl;

$R^{3a}$, $R^{3b}$ and $R^{3c}$ are either (a) three independent C1-C6 alkyl groups, (b) $R^{3a}$ is C1-C6 alkyl and $R^{3b}$ and $R^{3c}$ together form a saturated hetero monocyclic ring group with the N to which they are bonded or (c) $R^{3a}$, $R^{3b}$ and $R^{3c}$ together form a saturated hetero bicyclic ring group with the N to which they are bonded;

G is selected from the group consisting of OH, halide and $OR^6$; and $R^6$ is selected from the group consisting of an aliphatic group, substituted aliphatic group, aryl, substituted aryl, arylalkyl, and substituted arylalkyl.

In the compounds, salts and processes described herein, R is selected from the group consisting of alkoxy, substituted alkoxy, aryloxy, substituted aryloxy, arylalkoxy, substituted arylalkoxy and dialkylamino. Preferably, R is selected from the group consisting of C1-C4 alkoxy and C1-C6 dialkylamino. More preferably, R is dimethylamino.

In the compounds, salts and processes described herein, $R^1$ is $CR^{1a}R^{1b}R^{1c}$; wherein $R^{1a}$, $R^{1b}$ and $R^{1c}$ are independently selected from the group consisting of H, alkyl, —C≡$CR^{1d}$, —$CR^{1e}$=$C(R^{1e})_2$, aryl and substituted aryl; $R^{1d}$ is H, alkyl, substituted alkyl, aryl, substituted aryl, arylalkyl, and substituted arylalkyl; $R^{1e}$ is either (a) three independent groups selected from the group consisting of H, alkyl, substituted alkyl, aryl, substituted aryl, arylalkyl, and substituted arylalkyl or (b) two $R^{1e}$ taken together form a cyclic hydrocarbon ring with the carbon or carbons to which they are bonded, and the other $R^{1e}$ is selected from the group consisting of H, alkyl, substituted alkyl, aryl, substituted aryl, arylalkyl, and substituted arylalkyl; wherein at least one of $R^{1a}$, $R^{1b}$ and $R^{1c}$ is —C≡$CR^{1d}$, —$CR^{1e}$=$C(R^{1e})_2$, aryl or substituted aryl.

Preferably, $R^{1a}$, $R^{1b}$ and $R^{1c}$ are independently selected from the group consisting of H, aryl, and substituted aryl. More preferably, $R^{1a}$ and $R^{1b}$ are H, and $R^{1c}$ is phenyl ($R^1$ is benzyl); $R^{1a}$, $R^{1b}$ and $R^{1c}$ are phenyl ($R^1$ is trityl); $R^{1a}$ and $R^{1b}$ are H, and $R^{1c}$ is substituted phenyl ($R^1$ is substituted benzyl), wherein the substituent is selected from R''', OR''', halogen, and $NO_2$, wherein R''' is methyl; $R^{1a}$ and $R^{1b}$ are H, and $R^{1c}$ is —CH=$CH_2$ ($R^1$ is allyl); or $R^{1a}$ and $R^{1b}$ are H, and $R^{1c}$ is —C≡CH ($R^1$ is propargyl). Most preferably, $R^1$ is benzyl.

In the compounds, salts and processes described herein, $R^2$ is selected from the group consisting of an aliphatic group, substituted aliphatic group, aryl, substituted aryl, arylalkyl and substituted arylalkyl. The aliphatic group is preferably selected from the group consisting of methyl, ethyl, n-propyl, isopropyl, n-butyl, t-butyl, isobutyl, sec-butyl, 2-methyl-2-hexanyl, 1-methylcyclohexyl, cyclopropylmethyl, (cyclohexyl)methyl, isomers of n-pentyl, isomers of n-hexyl, isomers of n-heptyl, and isomers of n-octyl. Preferably, the substituted aliphatic group is substituted with trimethylsilyl or halide. The aryl group is preferably selected from the group consisting of phenyl, 1-naphthyl, 2-naphthyl and 4-biphenyl. The substituted aryl group is preferably substituted with one or more substituents selected from the group consisting of R''', OR''', halogen, and $NO_2$, wherein each R''' is methyl. Preferably, arylalkyl is selected from the group consisting of benzyl and phenethyl. Substituted arylalkyl is preferably substituted with one or more substituents selected from the group consisting of R''', OR''', halogen and NO$_2$, wherein each R''' is methyl.

Preferably, R$^2$ is an aliphatic group or a substituted aliphatic group. More preferably, R$^2$ is selected from the group consisting of t-butyl, 2-methyl-2-hexanyl, 2-trimethylsilylethyl and 1-methylcyclohexyl.

In the compounds, salts and processes described herein, R$^{3a}$, R$^{3b}$ and R$^{3c}$ may be either (a) three independent C1 to C6 alkyl groups. Alternatively, R$^{3a}$ may be a C1-C6 alkyl, and R$^{3b}$ and R$^{3c}$, together with the N to which they are bound, form a hetero monocyclic ring group. Preferably, the hetero monocyclic ring group is a pyrrolidine, piperidine or morpholine ring group. As a further alternative, R$^{3a}$, R$^{3b}$ and R$^{3c}$, together with the N to which they are bound, may form a saturated hetero bicyclic ring group. Preferably, the saturated hetero bicyclic ring group is 1,4-diazabicyclo[2.2.2]octane or quinuclidine. Most preferably, each of R$^{3a}$, R$^{3b}$ and R$^{3c}$ is ethyl.

In the compounds, salts and processes described herein, G is selected from the group consisting of OH, halide and OR$^6$, wherein R$^6$ is selected from the group consisting of an aliphatic group, substituted aliphatic group, aryl, substituted aryl, arylalkyl, and substituted arylalkyl. The aliphatic group is preferably selected from the group consisting of methyl, ethyl, n-propyl, isopropyl, n-butyl, t-butyl, isobutyl, sec-butyl, 2-methyl-2-hexanyl, 1-methylcyclohexyl, cyclopropylmethyl, (cyclohexyl)methyl, isomers of n-pentyl, isomers of n-hexyl, isomers of n-heptyl, and isomers of n-octyl. Preferably, the substituted aliphatic group is substituted with trimethylsilyl or halide. The aryl group is preferably selected from the group consisting of phenyl, 1-naphthyl, 2-naphthyl and 4-biphenyl. The substituted aryl group is preferably substituted with one or more substituents selected from the group consisting of R''', OR''', halogen, and NO$_2$, wherein each R''' is methyl. Preferably, arylalkyl is selected from the group consisting of benzyl and phenethyl. Substituted arylalkyl is preferably substituted with one or more substituents selected from the group consisting of R''', OR''', halogen and NO$_2$, wherein each R''' is methyl. Most preferably, G is OH or chloride.

In one embodiment of the present invention, a process is provided for the preparation of a compound of Formula (3):

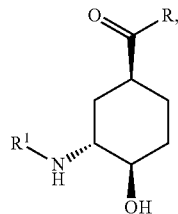

(3)

the process comprising reacting a compound of Formula (2):

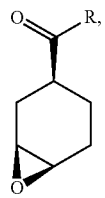

(2)

with a compound of Formula (20):

R$^1$—NH$_2$     (20), wherein R and R$^1$ are as defined above.

The reaction of a compound of Formula (2) and a compound of Formula (20) may be conducted with or without a solvent. When a solvent is used, the solvent is selected from the group consisting of alcohols, nitriles, N,N-dialkylamides, sulfoxides, ethers, aromatic hydrocarbons, aqueous mixtures thereof and water. For example, the solvent may be selected from the group consisting of methanol, ethanol, isopropanol, acetonitrile, N,N-dimethylformamide, N,N-dimethylacetamide, dimethyl sulfoxide, 1,2-dimethoxyethane, 1,2-diethoxyethane, diglyme, tetrahydrofuran, 1,4-dioxane, methyl t-butyl ether, anisole, toluene, xylene, aqueous mixtures thereof and water. Preferably, the solvent is water.

The reaction of a compound of Formula (2) and a compound of Formula (20) may be conducted at any suitable temperature. Preferably, the reaction temperature is in the range of room temperature to the boiling point of the reaction mixture. Most preferably, the reaction temperature is in the range of 75° C. to 95° C.

The compound of Formula (3) may be further reacted with an acid of Formula HA to produce a salt of Formula (3-S):

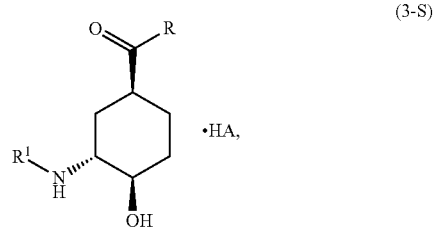

(3-S)

wherein R and R$^1$ are as defined above.

In the salt of Formula (3-S), HA may be any suitable organic or inorganic acid. For example, acid HA may be selected from the group consisting of hydrogen bromide, hydrogen chloride, citric acid, malonic acid, tartaric acid, succinic acid, formic acid, acetic acid, oxalic acid, methanesulfonic acid, p-toluenesulfonic acid and camphorsulfonic acid. Preferably, HA is methanesulfonic acid.

In another embodiment of the present invention, there is provided a compound of Formula (3) or a salt thereof:

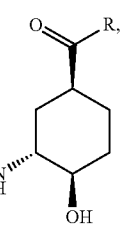

(3)

wherein R and R$^1$ are as defined above.

Preferably, the salt has the Formula (3-A1S):

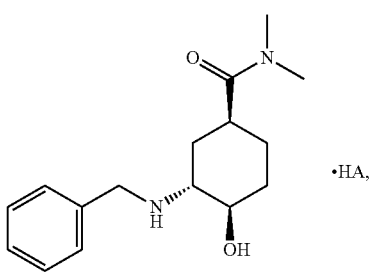

(3-A1S)

In the salt of Formula (3-A1S), HA may be any suitable organic or inorganic acid. For example, acid HA may be selected from the group consisting of a hydrogen halide, monocarboxylic acid, a dicarboxylic acid, a tricarboxylic acid and a sulfonic acid, hydrogen bromide, hydrogen chloride, citric acid, malonic acid, tartaric acid, succinic acid, formic acid, acetic acid, oxalic acid, methanesulfonic acid, p-toluenesulfonic acid and camphorsulfonic acid. Preferably, HA is methanesulfonic acid.

An embodiment of compound (3), for example, wherein R is dimethylamine and $R^1$ is benzyl, is a viscous oil. Conversion of an oil to an isolatable solid salt provides an improvement in the physical handling of the substance and furthermore provides an opportunity for purification, if required.

In another embodiment of the present invention, there is provided a process for the preparation of a compound of Formula (4):

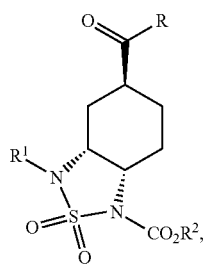

(4)

the process comprising reacting, a compound of Formula (3) or a salt thereof:

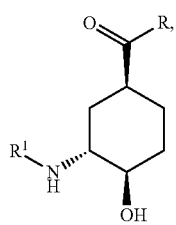

(3)

with a compound of Formula (B):

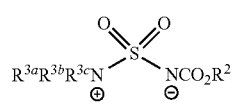

(B)

wherein R, $R^1$, $R^2$, $R^{3a}$, $R^{3b}$, and $R^{3c}$ are as defined above.

In the reaction of a compound of Formula (3) with a compound of Formula (B), about 2 mole equivalents of the compound of Formula (B) with respect to the compound of Formula (3) may be used. When 2 mole equivalents of the compound of Formula (B) are used, it is generally unnecessary for a separate step of activating the alcohol position with a separate activating group to provide a leaving group. Without wishing to be bound to any theory, it is believed that the second equivalent of the compound of Formula (B) reacts at the alcohol position to activate the alcohol and transform it into a better leaving group during formation of the compound of Formula (4).

Alternatively, in the reaction of a compound of Formula (3) with a compound of Formula (B), the compound of Formula (3) may first react with less than about 2 mole equivalents of a compound of Formula (B), with respect to a compound of Formula (3), to form an intermediate and then the compound of Formula (4) may be produced by further reacting the intermediate with a sulfonylating agent (S):

$$R^4SO_2X \qquad (S)$$

wherein

X is halogen or $-OSO_2R^5$; and $R^4$ and $R^5$ are independently selected from the group consisting of alkyl, substituted alkyl, phenyl and substituted phenyl.

In the sulfonylating agent of Formula (S), $R^4$ is preferably selected from the group consisting of C1-C6 alkyl, substituted C1-C6 alkyl wherein the substituent is halide, phenyl and substituted phenyl group wherein the substituent is selected from C1-C6 alkyl, C1-C6 alkoxy, halide and $NO_2$. More preferably, $R^4$ in the sulfonylating agent (S) is methyl and X is chloride.

The compound of Formula (B) may be provided as a preformed reagent or it may be prepared in situ by reacting together approximately equimolar amounts of chlorosulfonylisocyanate, $R^2OH$ and $NR^{3a}R^{3b}R^{3c}$. The formed compound of Formula (B) may then be reacted with a compound of Formula (3).

Preferably, the reaction of a compound of Formula (3) and a compound of Formula (B) occurs in the presence of a base B1, selected from the group of inorganic and organic bases. Preferably, base B1 is an inorganic base or an organic base. The base may be selected from the group consisting of tertiary amines, metal carbonates, metal bicarbonates and metal hydroxides. For example, base B1 may be selected from the group consisting of triethylamine, pyridine, DBU, potassium carbonate, cesium carbonate, sodium carbonate, sodium bicarbonate, sodium hydroxide and potassium hydroxide. Preferably, an excess amount of the amine $NR^{3a}R^{3b}R^{3c}$ used to make Formula (B) is used as the base B1.

The reaction of a compound of Formula (3) and a compound of Formula (B) may be conducted in a solvent selected from the group consisting of nitriles, chlorinated hydrocarbons, esters, ethers, aromatic hydrocarbons, N,N-dialkylamides and sulfoxides. For example, the solvent may be selected from the group consisting of acetonitrile, dichloromethane, ethyl acetate, isopropyl acetate, 1,2-dimethoxyethane, 1,2-diethoxyethane, diglyme, tetrahydrofuran, 1,4-dioxane, methyl t-butyl ether, anisole, toluene, xylene, N,N-dimethylformamide, N,N-dimethylacetamide and dimethyl sulfoxide. Preferably, the solvent is acetonitrile.

The reaction of a compound of Formula (3) and a compound of Formula (B) may be conducted at any suitable temperature. Preferably, the initial reaction temperature is in the range of −15° C. to room temperature and thereafter the reaction temperature is raised to between room temperature and the boiling point of the solvent to complete the reaction. More preferably, the initial reaction temperature is in the range of −10° C. to 10° C., and the final reaction temperature is in the range of 70° C. to 90° C.

Optionally, a compound of Formula (B) may be reacted with a salt of Formula (3-S):

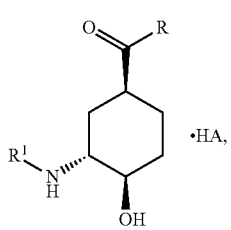

(3-S)

wherein HA is an organic or inorganic acid.

Acid HA may be a suitable organic or inorganic acid. For example, acid HA may be selected from the group consisting of hydrogen bromide, hydrogen chloride, formic acid, acetic acid, oxalic acid, methanesulfonic acid, p-toluenesulfonic acid and camphorsulfonic acid. Preferably, HA is methanesulfonic acid.

In the reaction of a salt of Formula (3-S) and a compound of Formula (B), additional base B1 may be used during the reaction to liberate the free base form of Formula (3-S).

In another embodiment of the present invention, there is provided a compound of Formula (4):

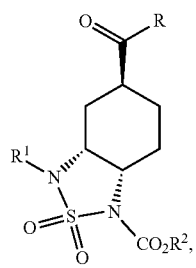

(4)

wherein R, $R^1$ and $R^2$ are as defined above.

A compound of Formula (4) wherein R is alkoxy, substituted alkoxy, aryloxy, substituted aryloxy, arylalkoxy or substituted arylalkoxy may, if desired, be converted to a compound of Formula (4-A) by known methods of ester hydrolysis and amide formation such as those reported in, for example, U.S. Pat. No. 8,686,189 B2. A compound of Formula (4-A) may be converted to a compound of Formula (1) according to the methods described herein.

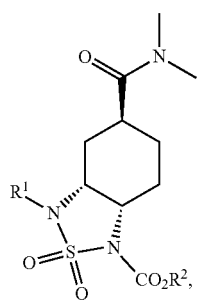

(4-A)

In another embodiment of the present invention, a process is provided for the preparation of a compound of Formula (5):

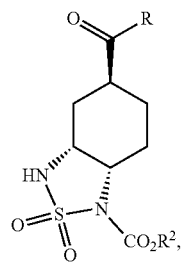

(5)

the process comprising deprotecting a compound of Formula (4):

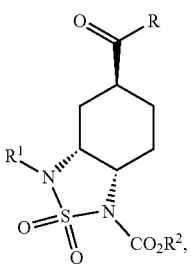

(4)

wherein R, $R^1$ and $R^2$ are as defined above.

Preferably, in the compound of Formula (4), $R^1$ is a substituted or unsubstituted benzylic protecting group. More preferably, $R^1$ is benzyl.

In the deprotection of a compound of Formula (4), that is, removal of the group $R^1$, suitable conditions for cleavage of benzylic, allylic and propargylic protecting groups from an amine may be employed. For example, suitable methods may be found in Greene, T. W.; Wuts, P. G. M. *Protective Groups in Organic Synthesis*; Fourth edition; Wiley: New York, 2007, in Liu, Yong et al. *Org. Biomol. Chem.* 2005, 3(18), 3329-3335 (de-allylation) and in Zheng, Huaiji et al. *Org. Lett.,* 2011, 13(24), 6448-6451 (de-propargylation). Preferably, hydrogenolysis conditions are employed.

Hydrogenolysis may be conducted in the presence of a suitable catalyst selected from the group consisting of palladium, platinum, rhodium, ruthenium, and Raney-nickel. The suitable catalyst may be finely dispersed solids or adsorbed on an inert support such as carbon or alumina. The suitable catalyst may be wet or dry. Preferably, the suitable catalyst is palladium hydroxide on carbon ($Pd(OH)_2$/C) or palladium on carbon (Pd/C). More preferably, the catalyst is 10 wt % palladium on carbon (10% w/w), 66% wet. The catalyst loading may be from about 0.1 wt % to about 20 wt % palladium with respect to the weight of a compound of Formula (4). Preferably, the catalyst loading is 20 wt % palladium with respect to the weight of a compound of Formula (4).

Hydrogenolysis is conducted in the presence of a hydrogen source selected from hydrogen gas or a hydrogen transfer reagent. The hydrogen transfer reagent may be a derivative of formic acid selected from the group consisting of cyclohexadiene, tetralin, sodium formate, ammonium formate, triethyl ammonium formate and formic acid. Preferably, the hydrogen source is sodium formate.

The deprotection of a compound of Formula (4) is conducted in a solvent selected from the group consisting of alcohols, ethers, aqueous mixtures thereof and water. For example, the solvent may be selected from the group consisting of methanol, ethanol, isopropanol, 1,2-dimethoxyethane, 1,2-diethoxyethane, diglyme, tetrahydrofuran, 1,4-dioxane, methyl t-butyl ether and anisole, aqueous mixtures thereof and water. Preferably, the solvent is selected from group consisting of C1-C3 alcohols.

The deprotection of a compound of Formula (4) is conducted at any suitable temperature. Preferably, the temperature is in the range of about 40° C. to about 85° C.

In another embodiment of the present invention, a process is provided for the preparation of a compound of Formula (1), or a salt thereof:

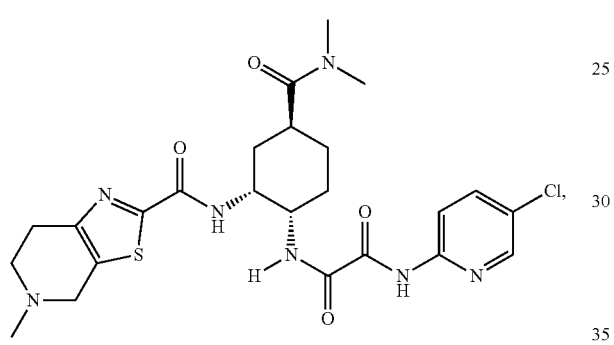

(1)

the process comprising:

(a) reacting a compound of Formula (5-A):

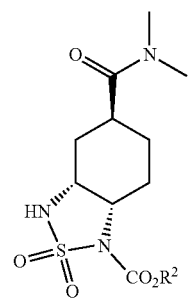

(5-A)

with a compound of Formula (21) or a salt thereof:

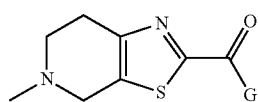

(21)

in the presence of a base B2 and, optionally in the presence of a coupling agent, to produce a compound of Formula (6-A):

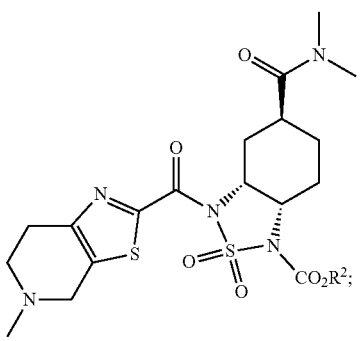

(6-A)

(b) deprotecting a compound of Formula (6-A) to produce a compound of Formula (7-A):

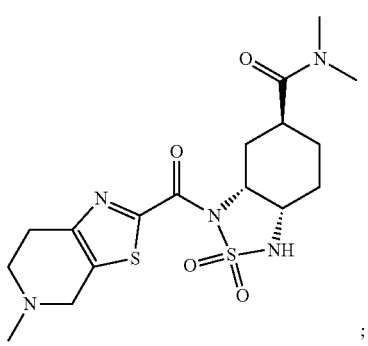

(7-A)

(c) desulfonylating a compound of Formula (7-A) to produce a compound of Formula (10-A):

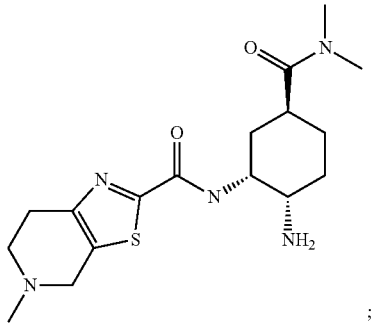

(10-A)

(d) reacting, in the presence of a base B3, a compound of Formula (10-A) or a salt thereof with a compound of Formula (22) or a salt thereof:

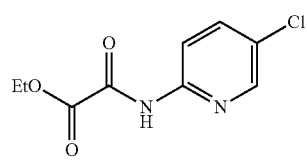

(22)

wherein $R^2$ and G are as defined above.

In the reaction of a compound of Formula (5-A) with a compound of Formula (21) or a salt thereof, G may be selected from OH, halide and $OR^6$. In the compound of Formula (21), $R^6$ may be an aliphatic group, substituted aliphatic group, aryl, substituted aryl, arylalkyl, and substituted arylalkyl. An aliphatic group may be selected from the group consisting of methyl, ethyl, n-propyl, isopropyl, n-butyl, t-butyl, isobutyl, sec-butyl, 2-methyl-2-hexanyl, 1-methylcyclohexyl, cyclopropylmethyl, (cyclohexyl)methyl, homologs and isomers of n-pentyl, homologs and isomers of n-hexyl, homologs and isomers of n-heptyl, homologs and isomers of n-octyl. A substituted aliphatic group may be substituted by trimethylsilyl or halide. Aryl may be selected from the group consisting of phenyl, 1-naphthyl, 2-naphthyl, 4-biphenyl. Substituted aryl may be substituted by one or more substituents selected from the group consisting of R''', OR''', halogen, and $NO_2$ wherein each R''' is methyl. Arylalkyl may be selected from the group consisting of benzyl and phenethyl. Substituted arylalkyl may be substituted by one or more substituents selected from the group consisting of R''', OR''', halogen and $NO_2$ wherein each R''' is methyl. Preferably, G is OH or chloride.

In the reaction of a compound of Formula (5-A) with a compound of Formula (21) or a salt thereof, when G is OH, a coupling agent may be required. Any suitable coupling agent useful for the preparation of peptides may be used, for example. The coupling agent may be selected from the group consisting of dicyclohexylcarbodiimide (DCC)/1-hydroxybenzotriazole (HOBt), N-(3-dimethylaminopropyl)-N'-ethylcarbodiimide hydrochloride (EDC HCl)/1-hydroxybenzotriazole (HOBt), propylphosphonic anhydride (T3P®), phosphoric acid bis(2-oxooxazolidide) chloride (BOP-Cl), N,N,N',N'-tetramethyl-O-(benzotriazol-1-yl)uronium tetrafluoroborate (TBTU), N,N,N',N'-tetramethyl-O-(1H-benzotriazol-1-yl)uronium hexafluorophosphate (HBTU) and 1-[bis(dimethylamino)methylene]-1H-1,2,3-triazolo[4,5-b]pyridinium 3-oxid hexafluorophosphate (HATU). Preferably, the coupling agent is EDC. HCl/HOBt.

Preferably, in the reaction of a compound of Formula (5-A) with a compound of Formula (21) or a salt thereof, G is chloride and a coupling agent is not required. Preferably, a hydrogen halide salt of the compound of Formula (21) is used. More preferably, the hydrogen halide salt is hydrogen chloride.

The reaction of a compound of Formula (5-A) with a compound of Formula (21) or a salt thereof is conducted in the presence of a base B2. Base B2 may be any suitable inorganic or organic base. Base B2 may be selected from the group consisting of tertiary amines, metal carbonates and metal bicarbonates. Preferably, base B2 may be selected from the group consisting of triethylamine, diisopropylethylamine, 4-dimethylaminopyridine (DMAP) and cesium carbonate.

The reaction of a compound of Formula (5-A) with a compound of Formula (21) or a salt thereof may be conducted in a solvent selected from the group consisting of nitriles, chlorinated hydrocarbons, esters, ethers, aromatic hydrocarbons, N,N-dialkylamides and water. For example, the solvent may be selected from the group consisting of acetonitrile, dichloromethane, chloroform, ethyl acetate, isopropyl acetate, 1,2-dimethoxyethane, 1,2-diethoxyethane, diglyme, tetrahydrofuran, 1,4-dioxane, methyl t-butyl ether, anisole, toluene, xylene, N,N-dimethylformamide, N,N-dimethylacetamide and water. Preferably, the solvent is dichloromethane or acetonitrile.

The reaction of a compound of Formula (5-A) with a compound of Formula (21) or a salt thereof may be conducted at any suitable temperature. Preferably, the temperature is in the range of about 0° C. to about 30° C.

The deprotection of a compound of Formula (6-A) to produce a compound of Formula (7-A), that is, the removal of the substituent $CO_2R^2$, is conducted under suitable conditions for cleavage of a carbamate protecting group including, for example, acidolysis, base hydrolysis and hydrogenolysis (when $R^2$ is arylalkyl).

Preferably, the deprotection is conducted by acidolysis using a suitable acid. Suitable acids may be selected from the group consisting of trifluoroacetic acid, methanesulfonic acid, p-toluenesulfonic acid, camphorsulfonic acid, trifluoromethanesulfonic acid and hydrogen chloride. Preferably, the acid is trifluoroacetic acid. The suitable acid may also function as solvent for the deprotection. Alternatively, the deprotection may be conducted in the presence of a solvent selected from the group consisting of nitriles, chlorinated hydrocarbons and water. Preferably, the solvent is dichloromethane.

When $R^2$ is arylalkyl, the deprotection may be conducted using hydrogenolysis conditions in a suitable solvent. The suitable solvent may be selected from the group consisting of alcohols, esters, ethers and aqueous mixtures thereof.

The deprotection of a compound of Formula (6-A) may be conducted at any suitable temperature. Preferably, the temperature is in the range of about 20° C. to about 80° C.

The desulfonylation of a compound of Formula (7-A) to produce a compound of Formula (10-A) may be conducted under suitable conditions for cleavage of a sulfonyl group from thiadiazolidine 1,1-dioxides. Preferably, deprotection occurs in the presence of pyridine. More preferably, the pyridine is provided as an aqueous solution.

The desulfonylation of a compound of Formula (7-A) may be conducted in a solvent selected from the group consisting of alcohols, nitriles, ethers, N,N-dialkylamides, sulfoxides and water. For example, the solvent may be selected from the group consisting of methanol, ethanol, isopropanol, acetonitrile, 1,2-dimethoxyethane, 1,2-diethoxyethane, diglyme, tetrahydrofuran, 1,4-dioxane, methyl t-butyl ether, anisole, N,N-dimethylformamide, N,N-dimethylacetamide, dimethyl sulfoxide and water. Preferably, the solvent is acetonitrile.

The desulfonylation of a compound of Formula (7-A) may be conducted at any suitable temperature. Preferably, the temperature is in the range of about 60° C. to about 100° C.

The compound of Formula (10-A) may be further reacted with an acid HA to produce a salt of Formula (10-AS):

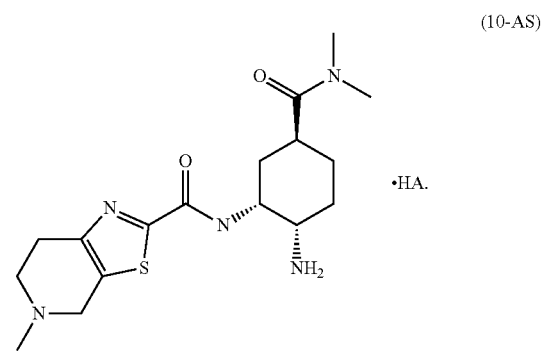

(10-AS)

wherein HA is an organic or inorganic acid.

In the salt of Formula (10-AS), HA may be any suitable organic or inorganic acid. Preferably, acid HA is a sulfonic acid. Preferably, acid HA is camphorsulfonic acid. More preferably, HA is (R)-camphorsulfonic acid and salt (10-AS) is provided as a crystalline solid.

Reaction of a compound of Formula (10-A) or a salt thereof and a compound of Formula (22) or a salt thereof may be conducted in a solvent selected from the group consisting of ethers, aromatic hydrocarbons, N,N-dialkylamides and sulfoxides. For example, the solvent may be selected from the group consisting of 1,2-dimethoxyethane, 1,2-diethoxyethane, diglyme, tetrahydrofuran, 1,4-dioxane, methyl t-butyl ether, anisole, toluene, xylene, N,N-dimethylformamide, N,N-dimethylacetamide, dimethyl sulfoxide and water. Preferably, the solvent is acetonitrile.

The reaction of a compound of Formula (10-A) or a salt thereof and a compound of Formula (22) or a salt thereof is conducted in the presence of a base B3. Base B3 may be any suitable inorganic or organic base. Preferably, base B3 is selected from the group consisting of tertiary amines and alkali metal carbonates. More preferably, base B3 is selected from the group consisting of triethylamine, diisopropylethylamine, 1,8-diazabicyclo(5.4.0)undec-7-ene (DBU), 4-dimethylaminopyridine and cesium carbonate.

The reaction of a compound of Formula (10-A) or a salt thereof and a compound of Formula (22) of a salt thereof may be conducted at any suitable temperature. Preferably, the temperature is in the range of about 50° C. to about 70° C.

In the reaction of a compound of Formula (10-A) and a compound of Formula (22), a salt of Formula (10-AS), as described herein, or a salt of Formula (22) may be used, with a corresponding adjustment of additional base B3 to facilitate reaction. Any crystalline and stable salt of a compound of Formula (22) may be used. Preferably, a hydrogen chloride salt of a compound of Formula (22) is used.

In another embodiment of the present invention, there is provided a compound of Formula (6-A):

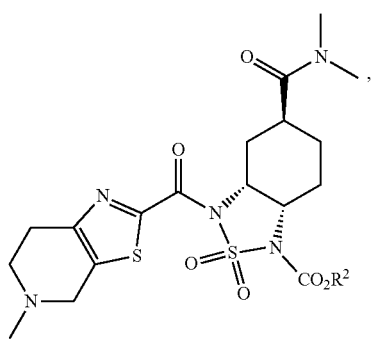

(6-A)

wherein $R^2$ is as defined above.

In another embodiment of the present invention, there is provided a compound of Formula (7-A):

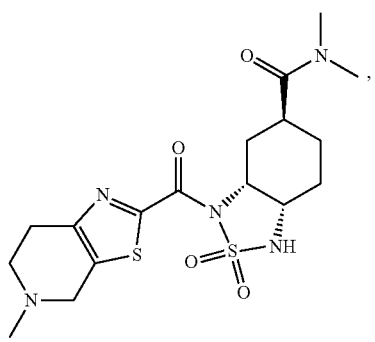

(7-A)

In another embodiment of the present invention, there is provided a process for the preparation of a compound of Formula (1) or a salt thereof:

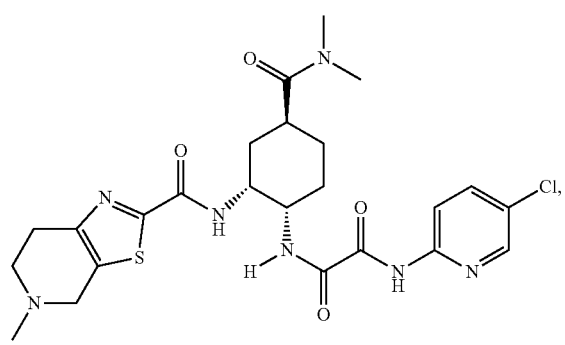

(1)

the process comprising:
(a) deprotecting a compound of Formula (4-A):

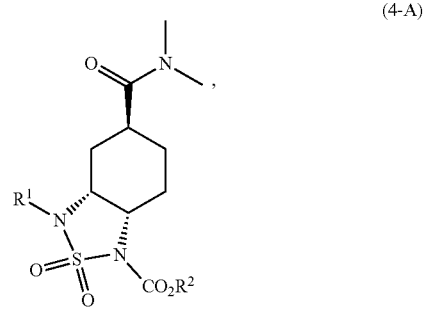

(4-A)

to produce a compound of Formula (5-A):

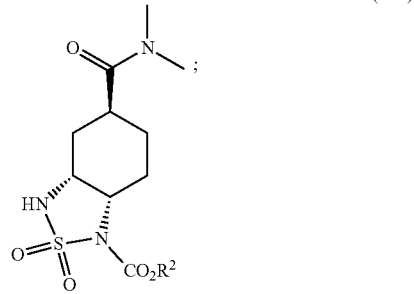

(5-A)

(b) desulfonylating a compound of Formula (5-A) to produce a compound of Formula (8-A):

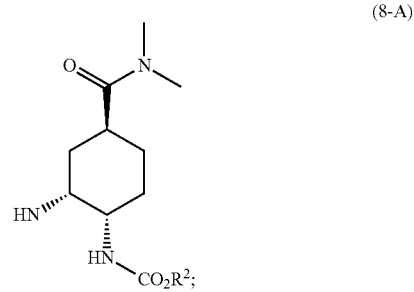

(8-A)

(c) reacting a compound of Formula (8-A) or a salt thereof with a compound of Formula (21) or a salt thereof:

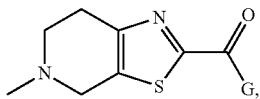
(21)

in the presence of a base B4 and, optionally, in the presence of a coupling agent, to produce a compound of Formula (9-A):

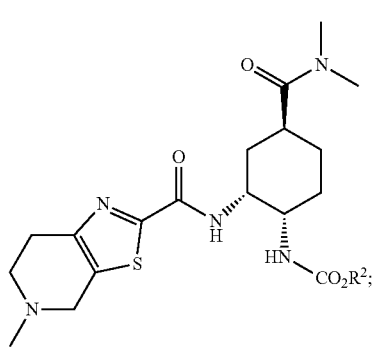
(9-A)

(d) deprotecting a compound of Formula (9-A) to produce a compound of Formula (10-A):

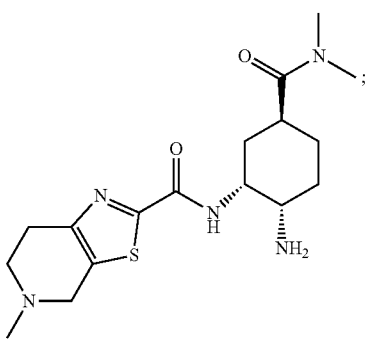
(10-A)

and (e) reacting, in the presence of a base B3, a compound of Formula (10-A) or a salt thereof with a compound of Formula (22) or a salt thereof:

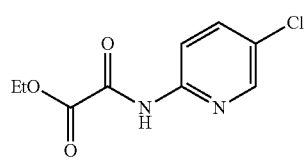
(22)

wherein $R^1$, $R^2$ and G are as defined above.

Preferably, in the compound of Formula (4-A), the protecting group $R^1$ is a substituted or unsubstituted benzylic protecting group. More preferably, $R^1$ is benzyl.

In the deprotection of a compound of Formula (4-A) to produce a compound of Formula (5-A), suitable conditions for cleavage of benzylic, allylic and propargylic type protecting groups from an amine may be employed. For example, suitable methods may be found in T. W. Greene and P. G. M. Wuts, "Protective Groups in Organic Synthesis", Fourth edition, Wiley, New York 2007, in Liu, Yong et al. *Org. Biomol. Chem.* 2005, 3(18), 3329-3335 (de-allylation) and in Zheng, Huaiji et al. *Org. Lett.*, 2011, 13(24), 6448-6451 (de-propargylation). Preferably, hydrogenolysis conditions are employed.

Hydrogenolysis may be conducted in the presence of a suitable catalyst selected from the group consisting of palladium, platinum, rhodium, ruthenium, and Raney-nickel. The suitable catalyst may be finely dispersed solids or adsorbed on an inert support such as carbon or alumina. The suitable catalyst may be wet or dry. Preferably, the suitable catalyst is palladium hydroxide on carbon ($Pd(OH)_2/C$) or palladium on carbon (Pd/C). More preferably, the catalyst is 10 wt % palladium on carbon (10% w/w), 66% wet. The catalyst loading may be from about 0.1 wt % to about 20 wt % palladium with respect to the weight of a compound of Formula (4). Preferably, the catalyst loading is 20 wt % palladium with respect to the weight of a compound of Formula (4).

Hydrogenolysis is conducted in the presence of a hydrogen source selected from hydrogen gas or a hydrogen transfer reagent. The hydrogen transfer reagent may be a derivative of formic acid selected from the group consisting of cyclohexadiene, tetralin, sodium formate, ammonium formate, triethyl ammonium formate and formic acid. Preferably, the hydrogen source is sodium formate.

The deprotection of a compound of Formula (4-A) is conducted in a solvent selected from the group consisting of methanol, ethanol, isopropanol, 1,2-dimethoxyethane, 1,2-diethoxyethane, diglyme, tetrahydrofuran, 1,4-dioxane, methyl t-butyl ether and anisole, aqueous mixtures thereof and water. Preferably, the solvent is selected from group consisting of C1-C3 alcohols.

The deprotection of a compound of Formula (4-A) is conducted at any suitable temperature. Preferably, the temperature is in the range of about 40° C. to about 85° C.

Preferably, the deprotection of a compound of Formula (4-A) is conducted without isolation of a compound of Formula (5-A) and the compound of Formula (5-A) is further subjected to desulfonylation. Conveniently, the deprotection and desulfonylation steps (steps (a) and (b)) may be telescoped to reduce operations associated with the isolation and manipulation of a compound of Formula (5-A).

The desulfonylation of a compound of Formula (5-A) to produce a compound of Formula (8-A) may be conducted under similar conditions as described above for desulfonylation of a compound of Formula (7-A) to produce a compound of Formula (10-A).

The compound of Formula (8-A) may be further reacted with an acid HA to produce a salt of Formula (8-AS):

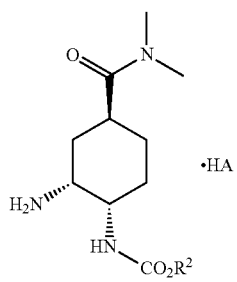

wherein HA is an organic or inorganic acid.

Acid HA may be any suitable organic or inorganic acid. Acid HA may be selected from the group consisting of a mono-, di-, or tricarboxylic acid, a mineral acid and a sulfonic acid. HA may be selected from the group consisting of sulfuric acid, benzoic acid, tartaric acid, citric acid, camphorsulfonic acid and p-toluenesulfonic acid. Preferably, HA is citric acid.

In the reaction of a compound of Formula (8-A) or a salt thereof with a compound of Formula (21) or a salt thereof, when G is OH, a coupling agent may be required. Any suitable coupling agent useful for the preparation of peptides may be used, for example. The coupling agent may be selected from the group consisting of dicyclohexylcarbodiimide (DCC)/1-hydroxybenzotriazole (HOBt), N-(3-dimethylaminopropyl)-N'-ethylcarbodiimide hydrochloride (EDC HCl)/1-hydroxybenzotriazole (HOBt), propylphosphonic anhydride (T3P®), phosphoric acid bis(2-oxooxazolidide) chloride (BOP-Cl), N,N,N',N'-tetramethyl-O-(benzotriazol-1-yl)uronium tetrafluoroborate (TBTU), N,N,N',N'-tetramethyl-O-(1H-benzotriazol-1-yl)uronium hexafluorophosphate (HBTU) and 1-[bis(dimethylamino)methylene]-1H-1,2,3-triazolo[4,5-b]pyridinium 3-oxid hexafluorophosphate (HATU). Preferably, the coupling agent is EDC.HCl/HOBt.

Preferably, in the reaction of a compound of Formula (8-A) or a salt thereof with a compound of Formula (21) or a salt thereof, G is OH and a coupling agent is used. Preferably, the coupling agent is EDC.HCl/HOBt.

The reaction of a compound of Formula (8-A) or a salt thereof with a compound of Formula (21) or a salt thereof is conducted in the presence of a base B4. Base B4 may be any suitable inorganic or organic base. Base B4 may be selected from the group consisting of tertiary amines and metal carbonates and metal bicarbonates. Preferably, base B4 may be selected from the group consisting of triethylamine, diisopropylethylamine and cesium carbonate.

The reaction of a compound of Formula (8-A) or a salt thereof with a compound of Formula (21) or a salt thereof, may be conducted in a solvent selected from the group consisting of nitriles, chlorinated hydrocarbons, esters, ethers, N,N-dialkylamides, sulfoxides and water. For example, the solvent may be selected from the group consisting of acetonitrile, dichloromethane, chloroform, ethyl acetate, isopropyl acetate, 1,2-dimethoxyethane, 1,2-diethoxyethane, diglyme, tetrahydrofuran, 1,4-dioxane, methyl t-butyl ether, anisole, N,N-dimethylformamide, N,N-dimethylacetamide, dimethyl sulfoxide and water. Preferably, the solvent is dichloromethane or acetonitrile.

The reaction of a compound of Formula (8-A) or a salt thereof with a compound of Formula (21) or a salt thereof, may be conducted at any suitable temperature. Preferably, the temperature is in the range of about 0° C. to about 30° C.

The deprotection of a compound of Formula (9-A) to produce a compound of Formula (10-A) is conducted under suitable conditions for cleavage of a carbamate protecting group including acidolysis and hydrogenolysis (when $R^2$ is arylalkyl).

Preferably, the deprotection is conducted by acidolysis using a suitable acid. Suitable acids may be selected from the group consisting of trifluoroacetic acid, methanesulfonic acid, p-toluenesulfonic acid, camphorsulfonic acid, trifluoromethanesulfonic acid and hydrogen chloride. Preferably, the acid is trifluoroacetic acid. The suitable acid may also function as solvent for the deprotection. Alternatively, the deprotection may be conducted in the presence of a solvent selected from the group consisting of nitriles, chlorinated hydrocarbons and water. Preferably, the solvent is acetonitrile.

When $R^2$ is arylalkyl, the deprotection may be conducted using hydrogenolysis conditions in a suitable solvent. The suitable solvent may be selected from the group consisting of alcohols, esters, ethers and aqueous mixtures thereof.

The deprotection of a compound of Formula (9-A) may be conducted at any suitable temperature. Preferably, the temperature is in the range of about 20° C. to about 30° C.

The compound of Formula (10-A) may be further reacted with an acid HA to produce a salt of Formula (10-AS):

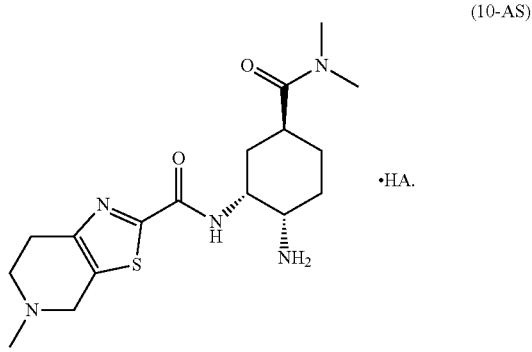 [SMILES: CN1CCc2nc(C(=O)N[C@@H]3C[C@@H](C(=O)N(C)C)CC[C@@H]3N)sc2C1]

wherein HA is an organic or inorganic acid.

In the salt of Formula (10-AS), HA may be any suitable organic or inorganic acid. Preferably, acid HA is a sulfonic acid. More preferably, acid HA is camphorsulfonic acid. Most preferably, HA is (R)-camphorsulfonic acid and salt (10-AS) is provided as a crystalline solid.

Preferably, the deprotection of a compound of Formula (9-A) is conducted without isolation of a compound of Formula (10-A) and the compound of Formula (10-A) is further subjected to the next step. Conveniently, the deprotection and coupling steps (steps (d) and (e)) may be telescoped to reduce operations associated with the isolation and manipulation of a compound of Formula (10-A).

Reaction of a compound of Formula (10-A) or a salt thereof and a compound of Formula (22) or a salt thereof may be conducted as described above.

In the reaction of a compound of Formula (10-A) and a compound of Formula (22), a salt of Formula (10-AS), as described herein, or a salt of Formula (22) may be used, with a corresponding adjustment of base B3 to facilitate reaction. Any crystalline and stable salt of a compound of Formula

(22) may be used. Preferably, a hydrogen chloride salt of a compound of Formula (22) is used.

The coupling sequence of a compound of Formula (10-A) and a compound of Formula (22), as described in the above embodiments, reduces or eliminates generation of 'Impurity X' as described in U.S. Pat. No. 8,357,808 B2. It is believed that coupling of the pyridine ring component to a compound of Formula (10-A) having the tetrahydrothiazolo ring component attached to the upper amino group of the cyclohexyl ring, rather than a t-butyl carbamate group as described in the art, advantageously prevents formation of this impurity.

In another embodiment of the present invention, there is provided a compound of Formula (8-A) or a salt thereof:

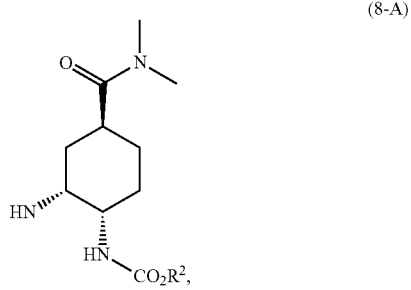

(8-A)

wherein $R^2$ is as defined above.

In another embodiment of the present invention, there is provided a compound of Formula (9-A):

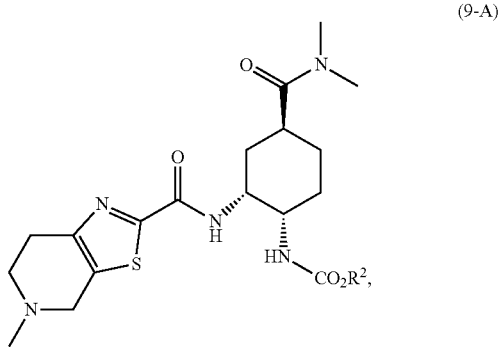

(9-A)

wherein $R^2$ is as defined above.

In another embodiment, there is provided a salt of Formula (10-AS):

(10-AS)

wherein HA is an organic or inorganic acid.

EXAMPLES

The following examples are illustrative of some of the embodiments of the invention described herein. It will be apparent to the skilled reader that various alterations to the described processes in respect of the reactants, reagents and conditions may be made when using the processes of the present invention without departing from the scope or intent thereof.

Example 1

Preparation of (1S,4S,5S)-4-bromo-6-oxabicyclo[3.2.1]octan-7-one

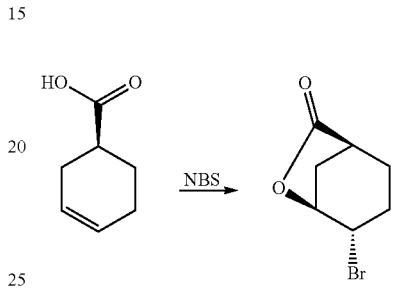

To a solution of (1S)-3-cyclohexene-1-carboxylic acid (24.50 g, 194.2 mmol) in dichloromethane (125 mL) was charged sodium bicarbonate (17.13 g, 203.9 mmol), and the reaction mixture was cooled to 5-10° C. N-bromosuccinimide (36.29 g, 203.9 mmol) was added in four portions (over 20 minutes) while maintaining the temperature below 20° C. The yellow to white suspension was warmed to room temperature and stirring continued for 2 hours until completion of the reaction as measured by TLC (thin-layer chromatography). The reaction mixture was first treated with 10% aqueous sodium thiosulfate solution (122 mL) yielding a negative test for the presence of bromine using potassium iodide starch test paper, followed by slowly adding a solution of sodium phosphate monobasic (32.20 g, 233.4 mmol) in water (122 mL) due to effervescence. After separation of the aqueous and organic phases, the organic phase was extracted with saturated ammonium chloride solution (2×122 mL) and the organic phase was dried over sodium sulfate and concentrated in vacuo to dryness to afford (1S,4S,5S)-4-bromo-6-oxabicyclo[3.2.1]octan-7-one as a white solid: 36.24 g (91% yield);

Example 2

Preparation of 4-Bromo-3-hydroxy-N,N-dimethyl-(1S,3S,4S)-cyclohexane carboxamide

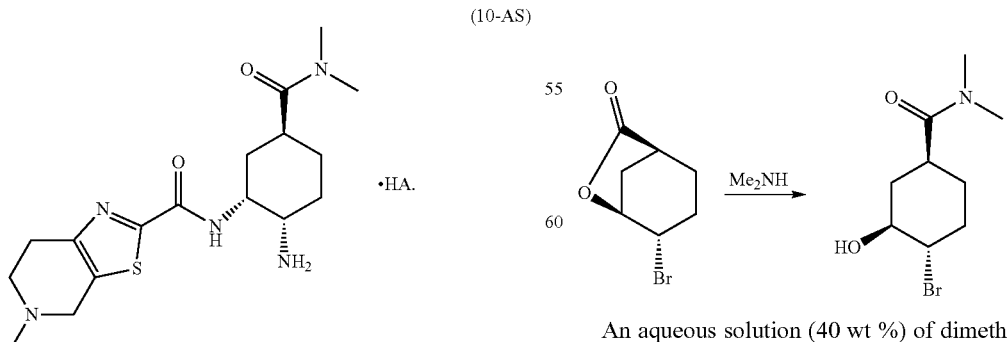

An aqueous solution (40 wt %) of dimethylamine (278.0 g, 312 mL, 2.475 mol) was charged to a mixture of (1S,4S,5S)-4-bromo-6-oxabicyclo[3.2.1]octan-7-one (145.00 g, 0.7070 mmol) in ethyl acetate (700 mL) at about 0° C. The solution was allowed to stir at room temperature for 19.5 hours. After reaction completion, the solution was cooled to about 0° C. and citric acid (138.1 g, 718.8 mmol) and saturated sodium chloride (150 mL) were charged, inducing an increase in the solution temperature to 17° C. The biphasic solution was stirred and warmed to room temperature for 0.5 h. The aqueous and organic phases were separated and the aqueous phase was extracted with ethyl acetate (8×150 mL). The combined organic phases were dried over anhydrous sodium sulfate (100 g), filtered and concentrated in vacuo at about 35° C. to a volume of about 200 mL to afford a slurry. Following addition of methyl t-butyl ether (500 mL), the mixture was cooled to about 0° C., filtered and washed with methyl t-butyl ether (20 mL) to afford 4-bromo-3-hydroxy-N,N-dimethyl-(1S,3S,4S)-cyclohexanecarboxamide (81.06 g, 46% yield) as a white solid.

Example 3

Preparation of N,N-Dimethyl-(1S,3S,6R)-7-oxabicyclo[4.1.0]heptane-3-carboxamide (2-A)

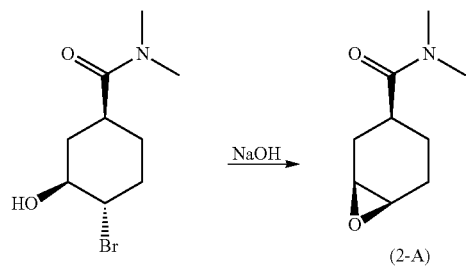

(2-A)

A mixture of 4-bromo-3-hydroxy-N,N-dimethyl-(1S,3S,4S)-cyclohexanecarboxamide (166.06 g, 663.8 mmol), dichloromethane (830 mL), an aqueous solution (50 wt %) of sodium hydroxide (74.35 g, 929.4 mol) and ice cold water (75 mL) was stirred at room temperature for 5 hours. Following reaction completion, the aqueous and organic phases were separated and the aqueous phase was extracted with dichloromethane (160 mL). The combined organic phases were dried over anhydrous sodium sulfate (100 g), filtered and concentrated in vacuo at about 35° C. to afford a thick oil. Methyl t-butyl ether (100 mL) was charged and the solution concentrated in vacuo at about 35° C. to afford a clear, colorless oil (128 g). Methyl t-butyl ether (70 mL) was charged followed by dropwise addition of heptanes (210 mL) to afford a white suspension. The product was collected by filtration, washed with heptanes (100 mL) and dried in vacuo at room temperature to afford N,N-dimethyl-(1S,3S,6R)-7-oxabicyclo[4.1.0]heptane-3-carboxamide (103.6 g, 92% yield) as a white solid.

Example 4

Preparation of (1S,3R,4R)-3-(benzylamino)-4-hydroxy-N,N-dimethylcyclohexane-1-carboxamide (Formula (3-A) wherein R¹=CR¹ᵃR¹ᵇR¹ᶜ; R¹ᵃ, R¹ᵇ=H and R¹ᶜ is phenyl or Formula (3-A1))

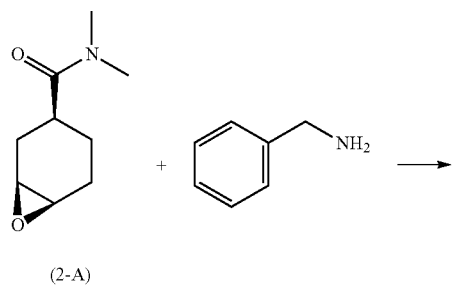

(2-A)

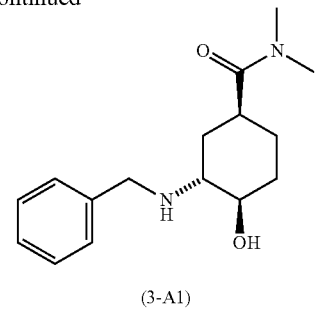

(3-A1)

A mixture of N,N-dimethyl-(1S,3S,6R)-7-oxabicyclo[4.1.0]heptane-3-carboxamide (49.36 g, 291.7 mmol), benzylamine (32.83 g, 306.4 mmol), and water (100 mL) was heated to 84° C. and maintained at this temperature for about 4 hours. The reaction mixture was then cooled to room temperature and extracted with dichloromethane (2×100 mL). The organic phases were combined, dried over anhydrous sodium sulfate, filtered, and concentrated to dryness to afford (1S,3R,4R)-3-(benzylamino)-4-hydroxy-N,N-dimethylcyclohexane-1-carboxamide as an oily residue (80.40 g, 93.4% pure by ¹H-NMR, 99.7% yield).

¹H-NMR (CDCl₃) δ: 1.29-1.40 (1H, m), 1.52-1.60 (1H, m), 1.63-1.76 (1H, m), 1.85-1.95 (2H, m), 2.15-2.27 (1H, m), 2.92 (3H, s), 3.01 (3H, s), 2.94-3.09 (2H, m), 3.38-3.44 (1H, m), 3.75 (1H, d, J=13.0 Hz), 3.89 (1H, d, J=13.0 Hz), 7.31-7.33 (5H, m).

Example 5

Preparation of salts of (1S,3R,4R)-3-(benzylamino)-4-hydroxy-N,N-dimethylcyclohexane-1-carboxamide (salt of Formula (3-A) wherein R¹=CR¹ᵃR¹ᵇR¹ᶜ; R¹ᵃ, R¹ᵇ=H and R¹ᶜ is phenyl or Formula (3-A1S))

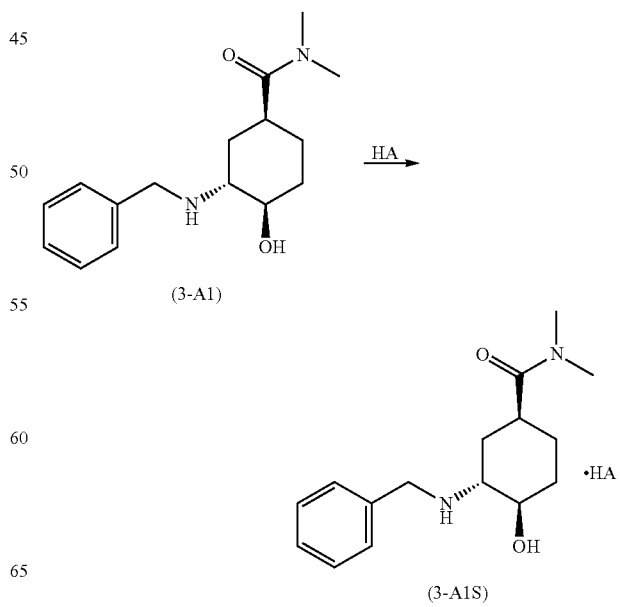

Example 5a

Preparation of Mesylate salt (HA=methanesulfonic acid)

To a solution of (1S,3R,4R)-3-(benzylamino)-4-hydroxy-N,N-dimethylcyclohexane-1-carboxamide (34.79 g, 117.6 mmol) in ethyl acetate (200 mL) was slowly added a solution of methanesulfonic acid (12.56 g, 130.0 mmol) in ethyl acetate (120 mL). The mixture was allowed to stir for 3 hours at room temperature prior to cooling to about 0° C. for one hour. The solid was collected by filtration, washed with cold ethyl acetate (2×50 mL) and dried in vacuo at about 45° C. to afford (1S,3R,4R)-3-(phenylmethyl)amino-4-hydroxy-N,N-dimethylcyclohexanecarboxamide mesylate (41.96 g, 96% yield).

$^1$H-NMR (D$_2$O) δ: 1.36-1.46 (1H, m), 1.55-1.67 (2H, m), 1.79-1.86 (2H, m), 2.16-2.19 (1H, m), 2.70 (3H, s), 2.79 (3H, s), 2.96 (3H, s), 3.15 (1H, bs), 3.48-3.63 (2H, m), 4.20 (1H, d, J=13.3 Hz), 4.29 (1H, d, J=13.3 Hz), 7.25-7.47 (5H, m).

Example 5b

Preparation of Formate salt (HA=formic acid)

To a solution of (1S,3R,4R)-3-(benzylamino)-4-hydroxy-N,N-dimethylcyclohexane-1-carboxamide (1.17 g, 3.95 mmol) in ethyl acetate (3 mL) was slowly added a solution of formic acid (0.22 g, 4.68 mmol) in ethyl acetate (0.3 mL). The mixture was stirred for 3 hours at room temperature, filtered, washed with ethyl acetate, and dried in vacuo at about 45° C. to afford (1S,3R,4R)-3-(phenylmethyl)amino-4-hydroxy-N,N-dimethylcyclohexanecarboxamide formate (0.98 g, 77% yield).

$^1$H-NMR (D$_2$O) δ: 1.27-1.32 (1H, m), 1.36-1.40 (2H, m), 1.47-1.61 (2H, m), 1.73-1.91 (1H, m), 2.72 (3H, s), 2.89 (3H, s), 3.08 (1H, bs), 3.39-3.57 (2H, m) 4.12 (1H, d, J=13.3 Hz), 4.22 (1H, d, J=13.3 Hz), 7.35 (5H, bs), 8.26 (1H, s).

Example 5c

Preparation of Formate salt (HA=acetic acid)

To a solution of (1S,3R,4R)-3-(benzylamino)-4-hydroxy-N,N-dimethylcyclohexane-1-carboxamide (1.13 g, 3.82 mmol) in ethyl acetate (2 mL) was added slowly a solution of acetic acid (0.25 g, 4.16 mmol) in ethyl acetate (0.5 mL). Following concentrating the solution to dryness, the residue was suspended in acetonitrile (3 mL) with stirring for 30 hours at room temperature. The solid was collected by filtration, washed with acetonitrile, and dried in vacuo at about 45° C. to afford (1S,3R,4R)-3-(phenylmethyl)amino-4-hydroxy-N,N-dimethylcyclohexanecarboxamide acetate (0.60 g, 47% yield).

$^1$H-NMR (D$_2$O) δ: 1.40-1.52 (1H, m), 1.36-1.40 (2H, m), 1.58-1.79 (2H, m), 1.60 (3H, s), 2.06-2.11 (1H, m), 2.72 (3H, s), 2.89 (3H, s), 3.07 (1H, bs), 3.33-3.56 (2H, m) 4.08 (1H, d, J=13.4 Hz), 4.18 (1H, d, J=13.4 Hz), 7.34 (5H, bs).

Example 5d

Preparation of (R)-camphorsulfonate salt (HA=(R)-camphorsulfonic acid)

To a solution of (1S,3R,4R)-3-(benzylamino)-4-hydroxy-N,N-dimethylcyclohexane-1-carboxamide (1.13 g, 3.82 mmol) in acetonitrile (5 mL) was added slowly a solution of (R)-camphorsulfonic acid (1.00 g, 4.22 mmol) in acetonitrile (10 mL). Following concentrating the solution to dryness, the residue was suspended in ethyl acetate with stirring for 6 hours at room temperature. The solid was collected by filtration washed with acetonitrile, and dried in vacuo at about 45° C. to afford (1S,3R,4R)-3-(phenylmethyl)amino-4-hydroxy-N,N-dimethylcyclohexanecarboxamide (R)-camphorsulfonate (01.61 g, 83% yield).

$^1$H-NMR (D$_2$O) δ: 0.69 (3H, s), 0.90 (3H, s), 1.28-1.61 (5H, m), 1.76-1.94 (5H, m), 2.00-2.03 (1H, m), 2.12-2.17 (1H, m), 2.22-2.31 (2H, m), 2.75 (3H, s), 2.93 (3H, s), 3.11-3.16 (2H, m), 3.46-3.56 (2H, m) 4.16 (1H, d, J=13.4 Hz), 4.26 (1H, d, J=13.3 Hz), 7.37 (5H, bs).

Example 5e

Preparation of p-toluenesufonate salt (HA=(p)-toluenesulfonic acid)

To a solution of (1S,3R,4R)-3-(benzylamino)-4-hydroxy-N,N-dimethylcyclohexane-1-carboxamide (1.04 g, 3.51 mmol) in acetonitrile (3 mL) was added slowly a solution of p-toluenesulfonic acid (0.74 g, 3.89 mmol) in acetonitrile (1 mL). Following concentrating the solution to dryness, the residue was suspended in ethyl acetate with stirring for 30 minutes at room temperature. The solid was collected by filtration, washed with acetonitrile, and dried in vacuo at about 45° C. to afford (1S,3R,4R)-3-(phenylmethyl)amino-4-hydroxy-N,N-dimethylcyclohexanecarboxamide p-toluenesulfonate (1.29 g, 75% yield).

$^1$H-NMR (D$_2$O) δ: 1.28-1.37 (1H, m), 1.42-1.53 (2H, m), 1.65-1.77 (2H, m), 1.91-2.05 (1H, m), 2.19 (3H, s), 2.69 (3H, s), 2.83 (3H, s), 2.98 (1H, bs), 3.38-3.54 (2H, m) 4.06 (1H, d, J=13.3 Hz), 4.17 (1H, d, J=13.3 Hz), 7.16 (2H, d, J=8.0 Hz), 7.33 (5H, bs), 7.52 (2H, d, J=8.2 Hz).

Example 5f

Preparation of oxalate salt (HA=oxalic acid)

To a solution of (1S,3R,4R)-3-(benzylamino)-4-hydroxy-N,N-dimethylcyclohexane-1-carboxamide (1.07 g, 3.62 mmol) in acetonitrile (3 mL) was added slowly a solution of oxalic acid (0.22 g, 4.68 mmol) in methanol (0.5 mL). After 5 minutes, additional acetonitrile (5 mL) was added and stirring continued for 2 hours further at room temperature. The solid was collected by filtration, washed with acetonitrile, and dried in vacuo at 45° C. to afford (1S,3R,4R)-3-(phenylmethyl)amino-4-hydroxy-N,N-dimethylcyclohexane carboxamide oxalate (1.15 g, 81% yield).

$^1$H-NMR (D$_2$O) δ: 1.33-1.37 (1H, m), 1.55-1.59 (2H, m), 1.75-1.81 (2H, m), 2.11-2.16 (1H, m), 2.74 (3H, s), 2.91 (3H, s), 3.11 (1H, bs), 3.45-3.55 (2H, m) 4.14 (1H, d, J=13.3 Hz), 4.25 (1H, d, J=13.3 Hz), 7.33 (5H, bs).

Example 6

Preparation of tert-Butyl (3aR,5S,7aS)-3-benzyl-5-(dimethylcarbamoyl)-2,2-dioxooctahydro-1H-2,1,3-benzothiadiazole-1-carboxylate (Formula (4-A) wherein $R^1=CR^{1a}R^{1b}R^{1c}$; $R^{1a}$, $R^{1b}$=H; and $R^{1c}$ is phenyl; $R^2$=t-butyl or Formula (4-A1))

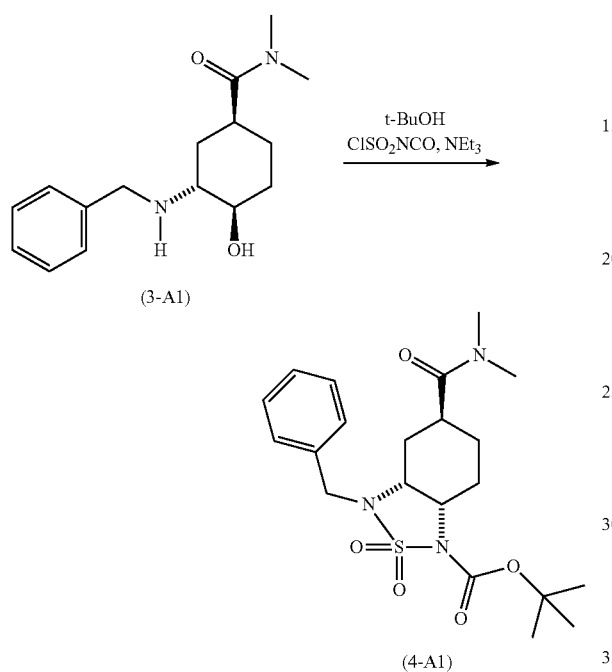

To a solution of tert-butanol (16.76 g, 226.1 mmol) in acetonitrile (50 mL) maintained at 0-10° C. was added a solution of chlorosulfonylisocyanate (98%, 32.66 g, 226.1 mmol) in acetonitrile (75 mL). To the resulting clear, colorless to pale yellowish solution was added a solution of triethylamine (65.9 g, 651.2 mmol) in acetonitrile (25 mL) at 0-10° C. The solution changed to a white suspension after half of the addition, gradually becoming thick at the end of the addition. To the resulting suspension was added a solution of (1S,3R,4R)-3-(benzylamino)-4-hydroxy-N,N-dimethylcyclohexane-1-carboxamide (25.00 g, 90.5 mmol) in acetonitrile (125 mL) at 0-10° C. The resulting thinner suspension was stirred at 0-10° C. for about 30 minutes, before the temperature was allowed to increase to room temperature. Following refluxing for 4 hours, the mixture was concentrated to about 180-200 mL under reduced pressure followed by slow addition of water (250 mL) under stirring. The resulting suspension was stirred for about 30 minutes, filtered, and the cake was washed with water (2×25 mL). The damp cake was finally pulped in hot 2-propanol (70 mL) at about 68° C. for about 30 minutes before stirring at about 0° C. for 1 hour. The crude product was collected by filtration, washed with cold 2-propanol (2×25 mL), and dried in vacuo at about 45° C. to afford tert-Butyl-(3aR,5S,7aS)-3-benzyl-5-(dimethylcarbamoyl)-2,2-dioxooctahydro-1H-2,1,3-benzothiadiazole-1-carboxylate (23.78 g, 60% yield).

$^1$H-NMR (CDCl$_3$) δ: 1.37-1.50 (1H, m), 1.57 (9H, s), 1.64-1.69 (1H, m), 1.83-1.94 (3H, m), 2.14-2.38 (2H, m), 2.38 (3H, s), 2.77 (3H, s), 3.76 (1H, d, J=16.1 Hz), 3.78 (1H, bs) 4.00-4.07 (1H, m), 4.66 (1H, d, J=16.1 Hz), 7.25-7.47 (5H, m).

Example 7

Preparation of 2-methyl-2-hexanyl (3aR,5S,7aS)-3-benzyl-5-(dimethylcarbamoyl)-2,2-dioxooctahydro-1H-2,1,3-benzothiadiazole-1-carboxylate (Formula (4-A) wherein $R^1=CR^{1a}R^{1b}R^{1c}$; $R^{1a}$, $R^{1b}$=H; and $R^{1c}$ is phenyl, $R^2$=2-methyl-2-hexanyl or Formula (4-A2))

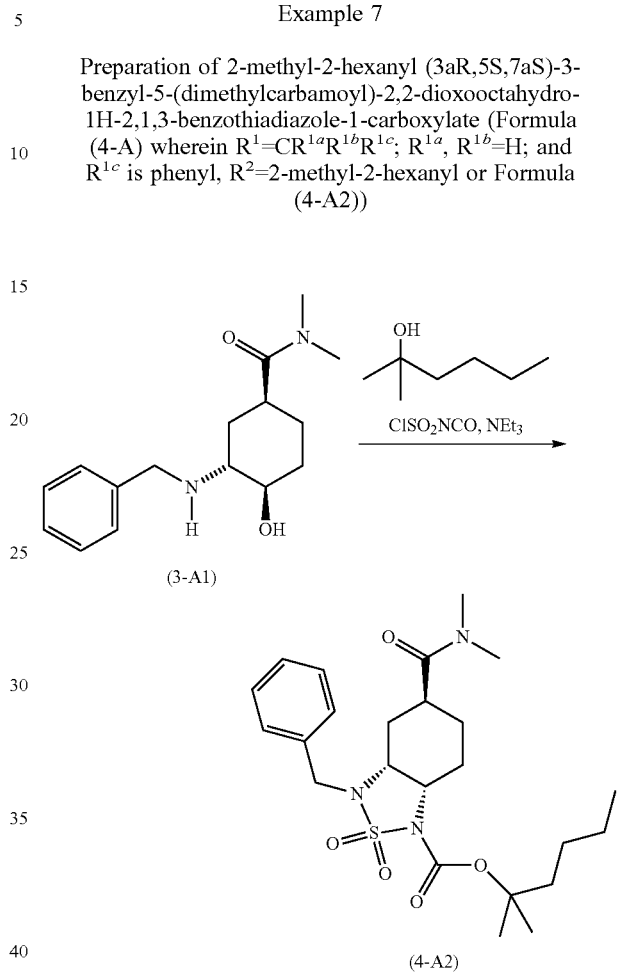

To a solution of 2-methyl-2-hexanol (6.57 g, 209.1 mmol) in acetonitrile (20 mL) maintained at 0-10° C. was added a solution of chlorosulfonylisocyanate (8.00 g, 56.5 mmol) in acetonitrile (25 mL). To the resulting clear, colorless to pale yellowish solution was added a solution of triethylamine (15.15 g, 149.7 mmol) in acetonitrile (30 mL) at 0-10° C. The solution changed to a white suspension after half of the addition, gradually becoming thick at the end of the addition. To the resulting suspension was added a solution of (1S,3R,4R)-3-(benzylamino)-4-hydroxy-N,N-dimethylcyclohexane-1-carboxamide (5.17 g, 18.7 mmol) in acetonitrile (27 mL) at 0-10° C. The resulting thinner suspension was stirred at 0-10° C. for about 30 minutes, before the temperature was allowed to increase to room temperature. Following refluxing for about 4.5 hours, the suspension was filtered at about 25° C. and the filtrate was concentrated to 40 mL. A solution (10 wt %) of ammonium chloride (60 mL) was added to the residue and the mixture allowed to stir at room temperature for 45 minutes. The solid was collected by filtration and washed with water to afford a crude damp solid (6.30 g), which was purified by crystallization using ethanol (15 mL) to afford 2-methyl-2-hexanyl(3aR,5S,7aS)-3-benzyl-5-(dimethylcarbamoyl)-2,2-dioxooctahydro-1H-2,1,3-benzothiadiazole-1-carboxylate as a white solid (4.57 g, 51% yield).

$^1$H-NMR (CDCl$_3$) δ: 0.89-0.94 (3H, m), 1.28-1.45 (6H, m), 1.54 (6H, s), 1.64-1.94 (5H, m), 2.12-2.34 (2H, m), 2.37 (3H, s), 2.77 (3H, s), 3.74 (1H, d, J=16.2 Hz), 3.79-3.80 (1H, m), 4.00-4.07 (1H, m), 4.68 (1H, d, J=16.1 Hz), 7.25-7.48 (5H, m).

Example 8

Preparation of 2-trimethylsilylethyl (3aR,5S,7aS)-3-benzyl-5-(dimethylcarbamoyl)-2,2-dioxooctahydro-1H-2,1,3-benzothiadiazole-1-carboxylate (Formula (4-A) wherein R$^1$=CR$^{1a}$R$^{1b}$R$^{1c}$; R$^{1a}$, R$^{1b}$=H; and R$^{1c}$ is phenyl, R$^2$=2-trimethylsilylethyl or Formula (4-A3))

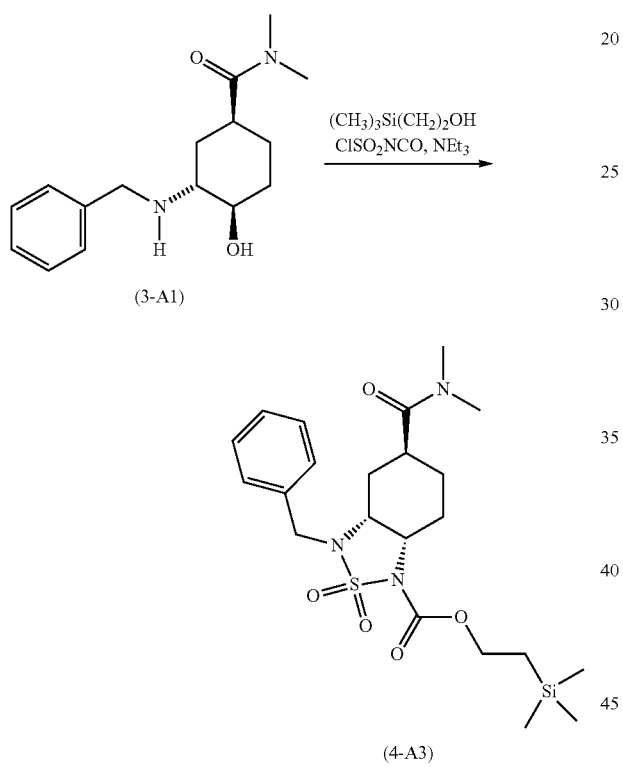

To a solution of 2-trimethylsilylethanol (98%, 2.93 g, 24.3 mmol) in acetonitrile (10 mL) maintained at 0-10° C. was added a solution of chlorosulfonylisocyanate (98%, 3.48 g, 24.1 mmol) in acetonitrile (6 mL). To the resulting clear, colorless to pale yellowish solution was added a solution of triethylamine (99.5%, 7.04 g, 69.2 mmol) in acetonitrile (5 mL) at 0-10° C. The solution changed to a white suspension after half of the addition, gradually becoming thick at the end of the addition. To the resulting suspension was added a solution of (1S,3R,4R)-3-(benzylamino)-4-hydroxy-N,N-dimethylcyclohexane-1-carboxamide (93.4%, 2.84 g, 9.60 mmol) in acetonitrile (10 mL) at 0-10° C. The resulting thinner suspension was stirred at 0-10° C. for about 30 minutes, before the temperature was allowed to increase to room temperature. Following refluxing for 4 hours, the mixture was concentrated to about 20-25 mL under reduced pressure followed by slow addition of water (25 mL). The resulting suspension was cooled to about 0° C. and stirred for about 30 minutes. The product was collected by filtration, washed with cold water (2×5 mL), and dried in vacuo at 70° C. to afford 2-trimethylsilylethyl (3aR,5S,7aS)-3-benzyl-5-(dimethylcarbamoyl)-2,2-dioxooctahydro-1H-2,1,3-benzothiadiazole-1-carboxylate (2.91 g, 63% yield).

$^1$H-NMR (CDCl$_3$) δ: 0.06 (9H, s), 1.14-1.20 (2H, m), 1.33-1.47 (2H, m), 1.79-1.96 (3H, m), 2.14-2.21 (1H, m), 2.22-2.33 (1H, m), 2.38 (3H, s), 2.77 (3H, s), 3.76 (1H, d, J=16.2 Hz), 3.79-3.82 (1H, m), 4.05-4.12 (1H, m), 4.37-4.43 (2H, m), 4.68 (1H, d, J=16.1 Hz), 7.25-7.47 (5H, m).

Example 9

Preparation of 1-methylcyclohexyl (3aR,5S,7aS)-3-benzyl-5-(dimethylcarbamoyl)-2,2-dioxooctahydro-1H-2,1,3-benzothiazole-1-carboxylate (Formula (4-A) wherein R$^1$=CR$^{1a}$R$^{1b}$R$^{1c}$; R$^{1a}$, R$^{1b}$=H; and R$^{1c}$ is phenyl, R$^2$=1-methylcyclohexyl or Formula (4-A4))

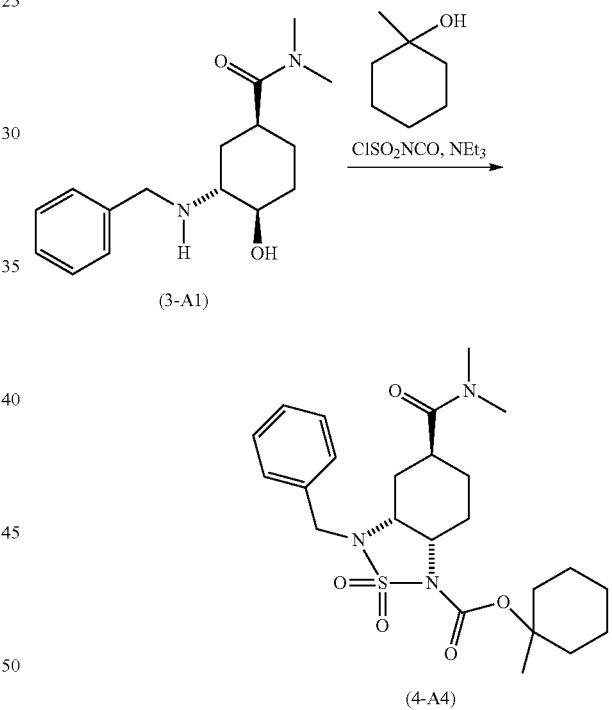

To a solution of 1-methylcyclohexanol (96%, 24.87 g, 209.1 mmol) in acetonitrile (70 mL) maintained at 0-10° C. was added a solution of chlorosulfonylisocyanate (98%, 30.20 g, 209.1 mmol) in acetonitrile (50 mL) at 0-10° C. To the resulting clear, colorless to pale yellowish solution was added a solution of triethylamine (99.5%, 61.28 g, 602.6 mmol) in acetonitrile (100 mL) at 0-10° C. The solution changed to a white suspension after half of the addition, gradually becoming thick at the end of the addition. To the resulting suspension was added a solution of (1S,3R,4R)-3-(benzylamino)-4-hydroxy-N,N-dimethylcyclohexane-1-carboxamide (96.4%, 23.98 g, 83.6 mmol) in acetonitrile (90 mL) at 0-10° C. The resulting thinner suspension was stirred at 0-10° C. for about 30 minutes, before the temperature was allowed to increase to room temperature. Following refluxing for 4 hours, the mixture was concentrated to about 180-200 mL under reduced pressure followed by slow addition of water (240 mL) under stirring. The resulting suspension was stirred for about 30 minutes and filtered. The damp cake was pulped in hot 2-propanol (70 mL) at about 60° C. for about 30 minutes before stirring at about 0° C. for 1 hour. The crude product was collected by filtration, washed with cold 2-propanol (2×20 mL), and dried in vacuo at about 45° C. to afford 1-methyl-cyclohexyl(3aR,5S,7aS)-3-benzyl-5-(dimethylcarbamoyl)-2,2-dioxooctahydro-2,1,3-benzothiazole-1-carboxylate (27.18 g, 68% yield).

$^1$H-NMR (CDCl$_3$) δ: 1.18-1.56 (5H, m), 1.58 (3H, s), 1.65-2.00 (8H, m), 2.13-2.34 (4H, m), 2.37 (3H, s), 2.77 (3H, s), 3.75 (1H, d, J=16.2 Hz), 3.79-3.81 (1H, m), 4.02-4.09 (1H, m), 4.68 (1H, d, J=16.2 Hz), 7.25-7.48 (5H, m).

Example 10

Preparation of 1-methylcyclohexyl (3aR,5S,7aS)-3-benzyl-5-(dimethylcarbamoyl)-2,2-dioxooctahydro-1H-2,1,3-benzothiazole-1-carboxylate (Formula (4-A) wherein $R^1$=$CR^{1a}R^{1b}R^{1c}$; $R^{1a}$, $R^{1b}$=H; and $R^{1c}$ is phenyl, $R^2$=1-methylcyclohexyl or Formula (4-A4))

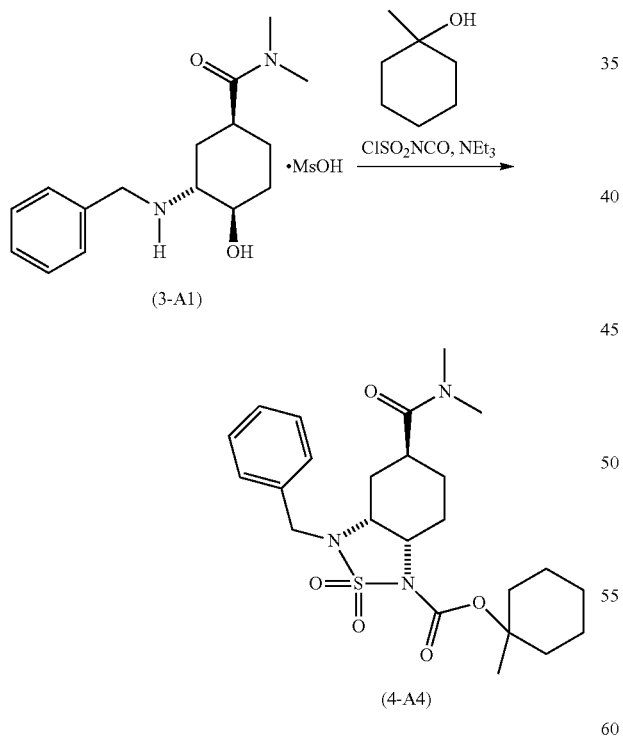

To a solution of 1-methylcyclohexanol (96%, 10.13 g, 85.2 mmol) in acetonitrile (30 mL) maintained at about −8° C. was added a solution of chlorosulfonylisocyanate (98%, 12.29 g, 85.1 mmol) in acetonitrile (30 mL). To the resulting clear, colorless solution was added a solution of triethylamine (99.5%, 24.93 g, 245.1 mmol) in acetonitrile (30 mL) at about −10° C. The solution changed to a white suspension after half of the addition, gradually becoming thick at the end of the addition. To the resulting suspension was added triethylamine (5.22 g, 51.33 mmol) and a solution of (1S, 3R,4R)-3-(phenylmethyl)amino-4-hydroxy-N,N-dimethyl-cyclohexanecarboxamide mesylate (95%, 13.36 g, 34.1 mmol) in acetonitrile (50 mL). The resulting thinner suspension was stirred at about −2° C. for about 30 minutes, before the temperature was allowed to increase to room temperature. Following refluxing for 4 hours, the mixture was concentrated to about 40 mL under reduced pressure followed by slow addition of water (100 mL) under stirring. The resulting suspension was cooled to about 0° C. and stirred for about 1 hour. The product was collected by filtration, washed with cold water (2×20 mL), and dried in vacuo at about 45° C. to afford 1-methyl-cyclohexyl(3aR, 5S,7aS)-3-benzyl-5-(dimethylcarbamoyl)-2,2-dioxooctahydro-1H-2,1,3-benzothiazole-1-carboxylate (9.24 g, 57% yield).

Example 11

Preparation of tert-Butyl (3aR,5S,7aS)-5-(dimethylcarbamoyl)-2,2-dioxooctahydro-3H-2,1,3-benzothiadiazole-1-carboxylate (Formula (5-A) wherein $R^2$=t-butyl or Formula (5-A1))

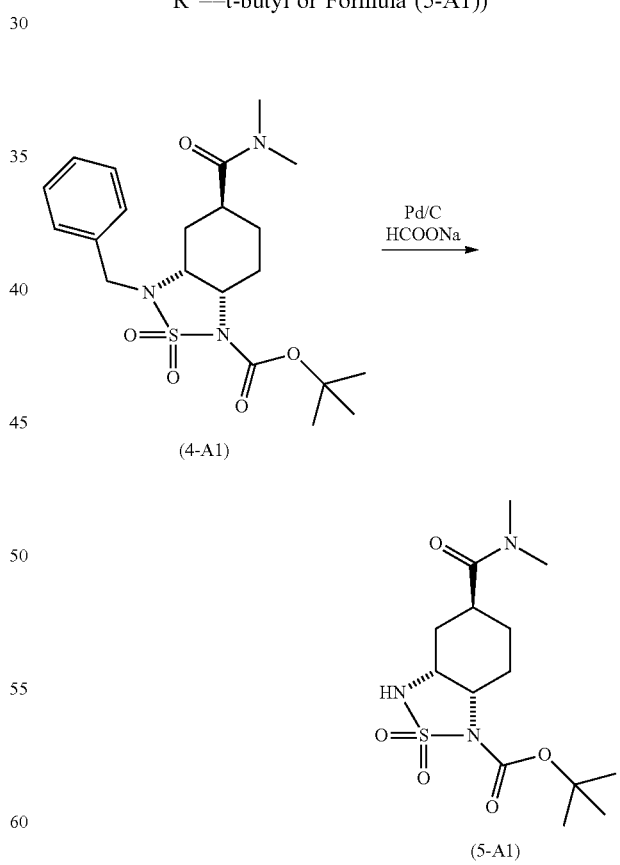

A suspension of tert-butyl(3aR,5S,7aS)-3-benzyl-5-(dimethylcarbamoyl)-2,2-dioxooctahydro-1H-2,1,3-benzothiadiazole-1-carboxylate (23.7 g, 54.2 mmol), palladium on carbon (4.74 g, 10% w/w, 66% wet), and sodium formate (11.05 g, 162.5 mmol) in methanol (166 mL) was stirred at 55° C. for 90 minutes. The mixture was cooled to room temperature, diluted with dichloromethane (75 mL), filtered and concentrated. The product was collected by filtration, washed with water (20 mL), and dried in vacuo at about 45° C. to afford tert-butyl-(3aR,5S,7aS)-5-(dimethylcarbamoyl)-2,2-dioxooctahydro-1H-2,1,3-benzothiadiazole-1-carboxylate (12.68 g, 67% yield).

$^1$H-NMR (CDCl$_3$) δ: 1.35-1.47 (1H, m), 1.52 (9H, s), 1.68-1.88 (2H, m), 2.01-2.17 (2H, m), 2.27-2.33 (1H, m), 2.94 (4H, bs), 3.08 (3H, s), 4.03-4.18(2H, m), 5.74 (NH, d).

Example 12

Preparation of 2-methyl-2-hexanyl (3aR,5S,7aS)-5-(dimethylcarbamoyl)-2,2-dioxooctahydro-1H-2,1,3-benzothiadiazole-1-carboxylate (Formula (5-A) wherein R$^2$=2-methyl-2-hexanyl or Formula (5-A2))

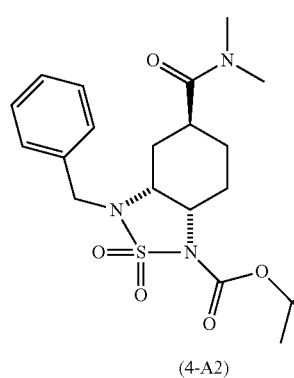

(4-A2)

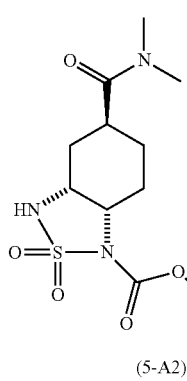

(5-A2)

A suspension of 2-methyl-2-hexanyl(3aR,5S,7aS)-3-benzyl-5-(dimethylcarbamoyl)-2,2-dioxooctahydro-1H-2,1,3-benzothiadiazole-1-carboxylate (5.03 g, 10.5 mmol), palladium hydroxide on carbon (0.77 g, 15% w/w) and ammonium formate (5.54 g, 87.9 mmol) in ethanol was stirred at 60° C. for 6 hours. The mixture was then cooled to room temperature, filtered through diatomaceous earth, and concentrated to dryness to afford 2-methyl-2-hexanyl (3aR,5S,7aS)-5-(dimethylcarbamoyl)-2,2-dioxooctahydro-1H-2,1,3-benzothiadiazole-1-carboxylate (4.17 g, yield 100% yield).

$^1$H-NMR (CDCl$_3$) δ: 0.89-0.92 (3H, m), 1.29-1.48 (2H, m), 1.50 (6H, s), 1.60-1.78 (5H, m), 2.12-2.34 (2H, m), 2.02-2.14 (2H, m), 2.25-2.35 (1H, m), 2.92-2.93 (1H, m), 2.94 (3H, s), 3.08 (3H, s), 4.05-4.11 (2H, m).

Example 13

Preparation of 2-trimethylsilylethyl (3aR,5S,7aS)-5-(dimethylcarbamoyl)-2,2-dioxooctahydro-1H-2,1,3-benzothiadiazole-1-carboxylate (Formula (5-A) wherein R$^2$=2-trimethylsilylethyl or (Formula (5-A3))

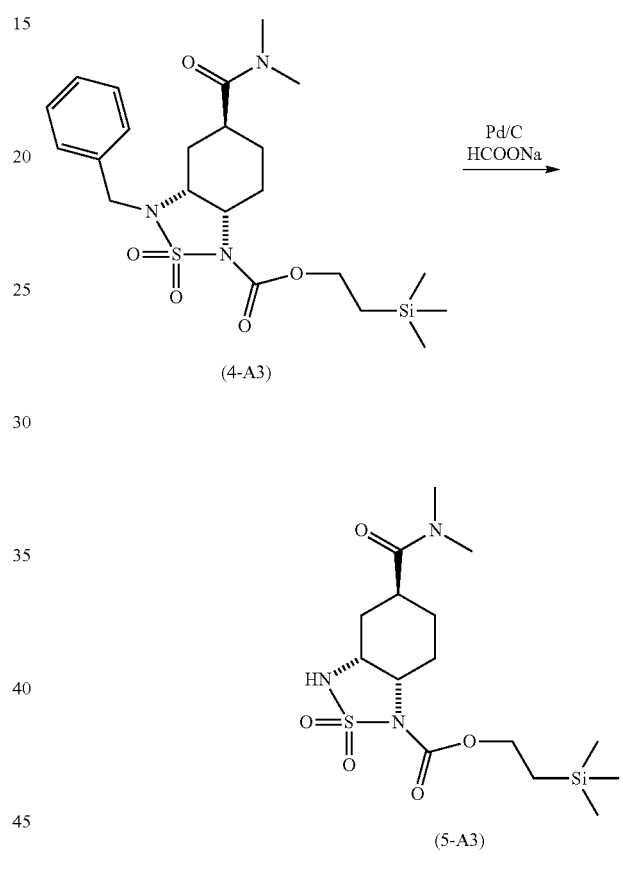

A suspension of 2-trimethylsilylethyl (3aR,5S,7aS)-3-benzyl-5-(dimethylcarbamoyl)-2,2-dioxooctahydro-1H-2,1,3-benzothiadiazole-1-carboxylate (1.72 g, 3.60 mmol), palladium on carbon (0.35 g, 10% w/w, 66% wet) and sodium formate (0.73 g, 10.7 mmol) in a mixture of methanol (12 mL) and water (5 mL) was stirred at 55° C. for 2 hours. The mixture was then cooled to room temperature, diluted with dichloromethane (10 mL), filtered through diatomaceous earth and washed with dichloromethane (10 mL). The filtrate was concentrated to about 6 mL and extracted with dichloromethane. The organic phase was dried over anhydrous sodium sulfate, filtered, and concentrated to dryness. The residue, corresponding with 2-trimethylsilylethyl (3aR,5S, 7aS)-5-(dimethylcarbamoyl)-2,2-dioxooctahydro-1H-2,1,3-benzothiadiazole-1-carboxylate (1.42 g), was used without any further purification in the subsequent step (Example 27).

$^1$H-NMR (CDCl$_3$) δ: 0.05 (9H, s), 1.07-1.13 (2H, m), 1.40-1.53 (1H, m), 1.67-1.81 (2H, m), 2.02-2.12 (2H, m), 2.24-2.26 (1H, m), 2.84-2.89 (1H, m), 2.94 (3H, s), 3.07 (3H, s), 4.05-4.13 (2H, m), 4.28-4.38 (2H, m).

Example 14

Preparation of 1-methyl cyclohexyl (3aR,5S,7aS)-5-(dimethylcarbamoyl)-2,2-dioxooctahydro-1H-2,1,3-benzothiadiazole-1 {3H}-carboxylate (Formula (5-A) wherein $R^2$=1-methylcyclohexyl or Formula (5-A4))

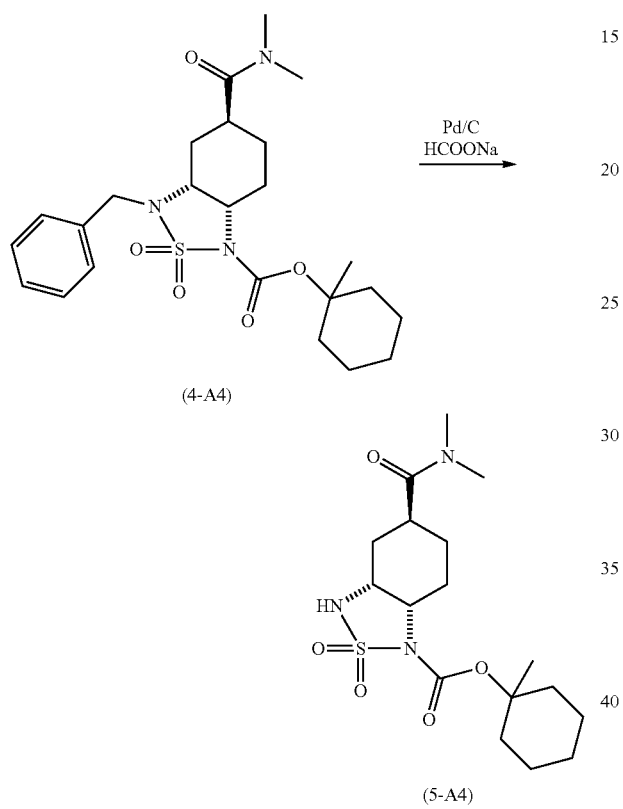

A flask was charged with 1-methyl cyclohexyl (3aR,5S,7aS)-3-benzyl-5-(dimethylcarbamoyl)-2,2-dioxooctahydro-1H-2,1,3-benzothiadiazole-1-carboxylate (12.00 g, 25.1 mmol), sodium formate (5.15 g, 75.4 mmol), and palladium on carbon (2.4 g, 10 wt % Pd, 66% wet) in a mixture of methanol (84 mL) and water (36 mL) and the suspension was heated to 55° C. for 3.5 hours. Following the completion of the reaction the suspension was cooled to room temperature and dichloromethane (36 mL) was charged. The suspension was filtered through a pad of diatomaceous earth and washed with dichloromethane (10 mL). The biphasic solution was concentrated in vacuo at about 35° C. to a volume of 15 mL. To this solution was added dichloromethane (200 mL), the phases separated and the aqueous phase extracted with dichloromethane (24 mL). The combined organic phases were concentrated in vacuo at about 35° C. to afford 1-methyl cyclohexyl (3aR,5S,7aS)-5-(dimethylcarbamoyl)-2,2-dioxooctahydro-1H-2,1,3-benzothiadiazole-1{3H}-carboxylate as a white foamy solid (8.43 g, 87% yield).

$^1$H-NMR (CDCl$_3$, 300 MHz) δ: 1.13-1.35 (1H, m), 1.35-1.70 (8H, m), 1.53 (3H, s), 1.72-1.88 (2H, m), 1.99-2.28 (4H, m), 2.28-2.40 (1H, m), 2.82-2.97 (1H, m), 2.93 (3H, s), 3.08 (3H, s), 4.06-4.13 (1H, m), 4.15 (1H, apparent q, J=5.3 Hz), 5.34 (1H, broad s).

Example 15

Preparation of tert-butyl (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole-1-carboxylate (Formula (6-A) wherein $R^2$=t-butyl or Formula (6-A1))

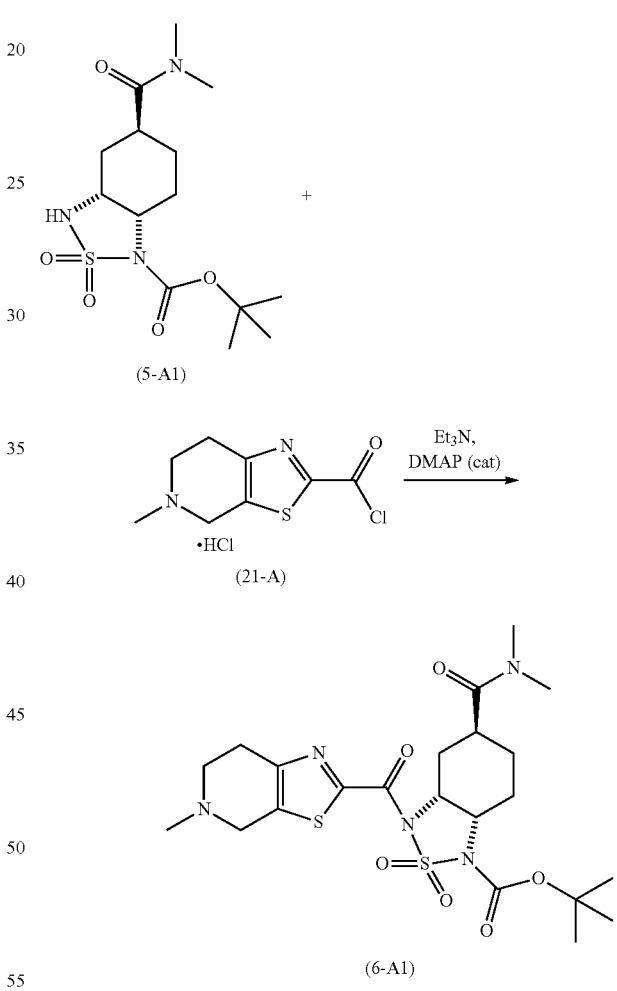

To a cooled (0-10° C.) solution of tert-Butyl-(3aR,5S,7aS)-5-(dimethylcarbamoyl)-2,2-dioxooctahydro-1H-2,1,3-benzothiadiazole-1-carboxylate (2.53 g, 7.3 mmol), triethylamine (2.59 g, 25.6 mmol), and DMAP (catalytic amount) in dichloromethane (10 mL) was added, in portions, 5-methyl-4,5,6,7-tetrahydrothiazolo[5,4-c]pyridine-2-carbonyl chloride hydrochloride (3.03 g, 10.3 mmol). The intense purple reaction mixture was stirred for 1 hour, and then diluted with dichloromethane (30 mL) and the organic phase was washed with water (3×50 mL), dried over anhydrous sodium sulfate and filtered. The filtrate was concentrated to dryness to afford tert-butyl (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole-1-carboxylate (3.75 g, 59% yield).

$^1$H-NMR (CDCl$_3$) δ: 1.55 (9H, s), 1.58-1.69 (1H, m), 1.76-1.87 (1H, m), 2.06-2.29 (3H, m), 2.37-2.49 (1H, m), 2.52 (3H, s), 2.77-2.89 (2H, m), 2.92 (3H, s), 2.97 (3H. s), 3.01-3.07 (3H, m), 3.66-3.83 (2H, m), 4.35-4.41 (1H, m), 5.87 (1H, m).

Example 16

Preparation of tert-butyl (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole-1-carboxylate (Formula (6-A) wherein R$^2$=t-butyl of Formula (6-A1))

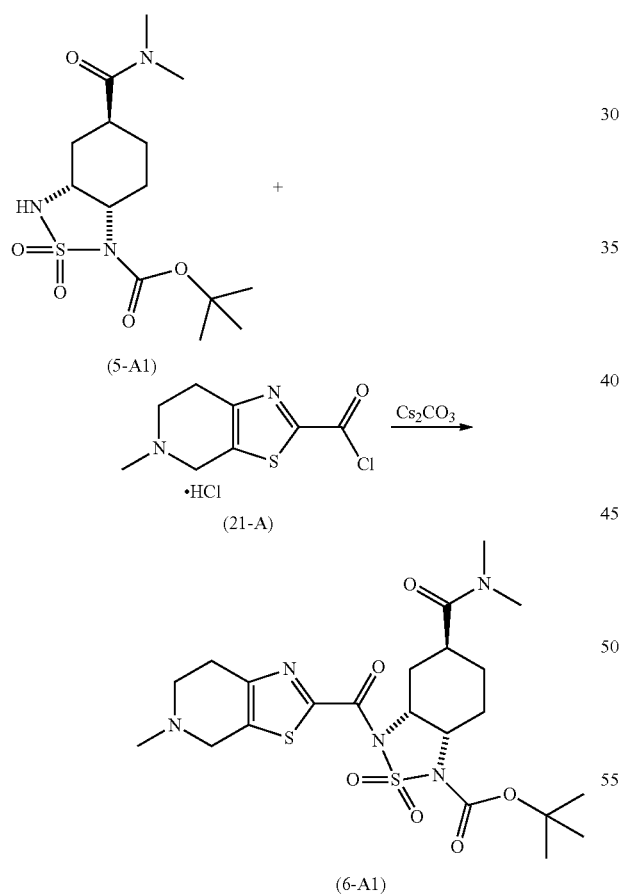

To a suspension of cesium carbonate (1.41 g, 4.317 mmol) in acetonitrile (5 mL) was added tert-butyl-(3aR,5S,7aS)-5-(dimethylcarbamoyl)-2,2-dioxooctahydro-1H-2,1,3-benzothiadiazole-1-carboxylate (500 mg, 1.439 mmol). To the thick suspension was added 5-methyl-4,5,6,7-tetrahydrothiazolo[5,4-c]pyridine-2-carbonyl chloride hydrochloride (475 mg, 1.87 mmol) and stirring was continued at room temperature for 19 hours. About 20% of unreacted starting material was detected by TLC. Additional 5-methyl-4,5,6,7-tetrahydrothiazolo[5,4-c]pyridine-2-carbonyl chloride hydrochloride (182 mg, 0.72 mmol) and acetonitrile were added and stirring was continued at room temperature for 10 hours. The reaction mixture was diluted with dichloromethane (10 mL), filtered through a pad of diatomaceous earth and washed with dichloromethane (2×20 mL). The filtrate was concentrated to dryness to afford crude tert-butyl(3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole-1-carboxylate as a foam (750 mg, 98% yield).

Example 17

Preparation of tert-butyl (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole-1-carboxylate (Formula (6-A) wherein R$^2$=t-butyl or Formula (6-A1))

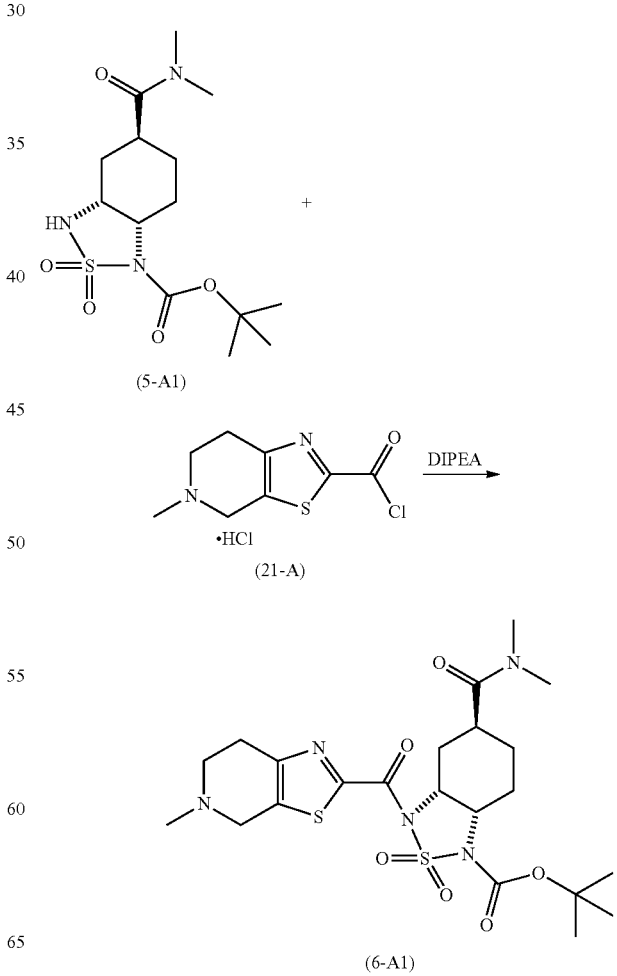

A suspension of tert-butyl-(3aR,5S,7aS)-5-(dimethylcarbamoyl)-2,2-dioxooctahydro-1H-2,1,3-benzothiadiazole-1-carboxylate (2.0 g, 5.756 mmol) in dichloromethane (14 mL) was cooled in and ice-MeOH bath (about −12° C.) and 5-methyl-4,5,6,7-tetrahydrothiazolo[5,4-c]pyridine-2-carbonyl chloride hydrochloride (1.9 g, 7.48 mmol) was added. Diisopropylethylamine (4.1 mL, 23.02 mmol) was added slowly. The reaction mixture was stirred at −5 to −10° C. over 12 hours. A small amount of unreacted starting material was detected by TLC. Additional 5-Methyl-4,5,6,7-tetrahydrothiazolo[5,4-c]pyridine-2-carbonyl chloride hydrochloride (291 mg, 1.15 mmol) was added and stirring was continued for another 3 hours. Following completion of the reaction (TLC), the reaction was quenched with saturated aqueous sodium bicarbonate solution (15 mL) and diluted with dichloromethane (15 mL) and water (15 mL). The organic layer was separated and washed with saturated aqueous sodium bicarbonate solution (10 mL), dried over anhydrous sodium sulfate and filtered. The filtrate was evaporated to dryness to afford the crude product tert-butyl (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole-1-carboxylate as a foam (3.0 g, 99% yield) which was pure by $^1$H NMR.

Example 18

Preparation (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole (Formula (7-A))

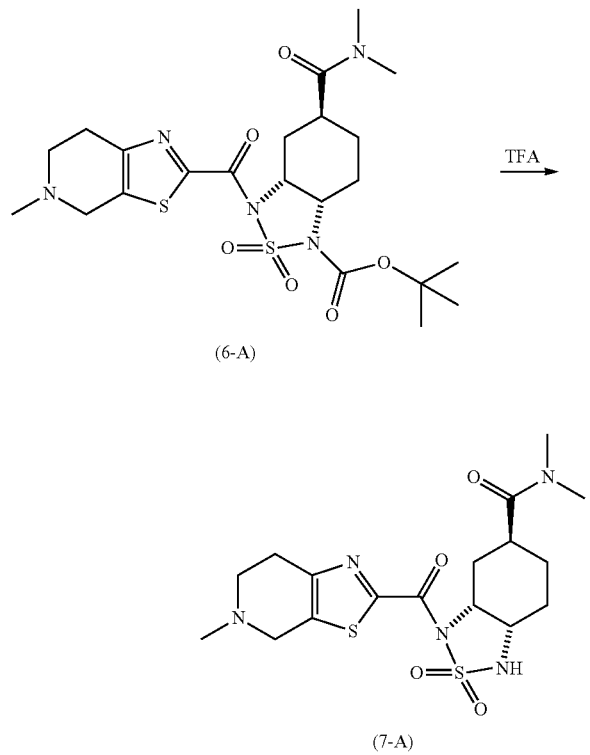

To a solution of tert-butyl-(3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole-1-carboxylate (3.74 g, 7.1 mmol) in dichloromethane (20 mL) was added portion-wise trifluoroacetic acid (8.32 g, 73.0 mmol) at room temperature. The mixture was stirred overnight, then diluted with dichloromethane (15 mL), and the reaction mixture was washed with sodium bicarbonate saturated solution (2×30 mL). The biphasic system was filtered (1.34 g solid) and the organic phase was separated and concentrated to dryness affording (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole (0.75 g).

$^1$H-NMR (CDCl$_3$) δ: 1.00-1.05 (1H, m), 1.55-2.03 (9H, m), 2.51 (3H, s), 2.80-2.90 (1H, m), 2.96 (3H, s), 3.02 (3H. s), 3.66-3.74 (1H, m), 4.02-4.07 (1H, m), 4.80 (1H, bs), 5.87 (1H, bs).

Example 19

Preparation of N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (Formula (10-A))

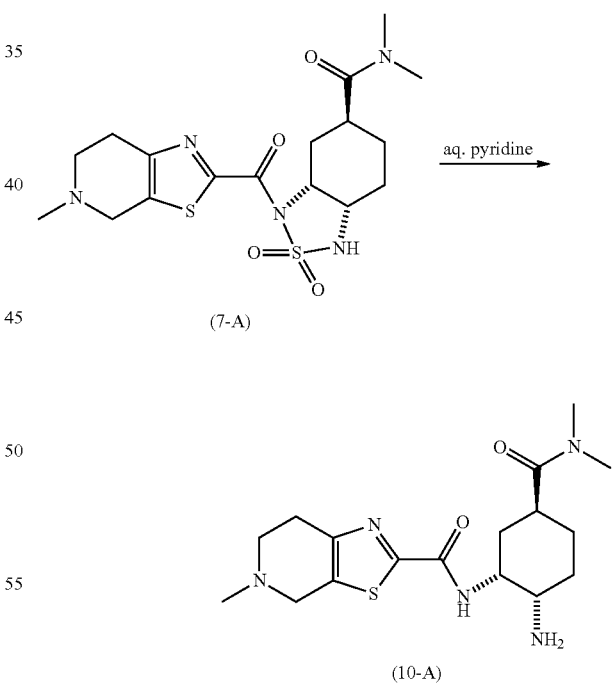

To a suspension of (3aR,5S,7aS)-5-(dimethylcarbamoyl)-3-(5-methyl-4,5,6,7-tetrahydro[1,3]thiazolo[5,4-c]pyridine-2-carbonyl)-2,2-dioxooctahydro-1H-2,1,3-benzothiadiazole (1.0 g, 2.338 mmol) in acetonitrile (10 mL) was added pyridine (1 mL, 11.7 mmol). The mixture was heated in an oil bath at about 90° C. for 1 hour. Thick solids precipitated from the reaction mixture. A solution of water (42 mg, 2.338 mmol) in acetonitrile (1 mL) was added and the reaction mixture was cooled to room temperature whereupon thick solids formed. The supernatant liquid was decanted and washed with acetonitrile. The solids were partitioned between saturated aqueous sodium bicarbonate (20 mL) and dichloromethane (50 mL). The aqueous layer was extracted with dichloromethane (30 mL) and the combined organic layer was dried over anhydrous sodium sulfate, filtered and evaporated to dryness to afford the product N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide as a foam (450 mg, 53% yield).

$^1$H-NMR (CDCl$_3$, 300 mHz) δ: 1.48 (1H, apparent dq, J=4.5 Hz, 12.0 Hz), 1.73-1.89 (4H, m), 2.35 (1H, broad d, J=14.0 Hz), 2.51 (3H, s), 2.67-2.89 (3H, m), 2.90-2.98 (2H, m), 2.92 (3H, s), 2.99 (3H, s), 3.10-3.19 (1H, m), 3.71 (2H, s), 4.25 (1H, broad s), 7.39 (1H, d, J=6.2 Hz).

Example 20

Preparation of N-1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (Edoxaban (1))

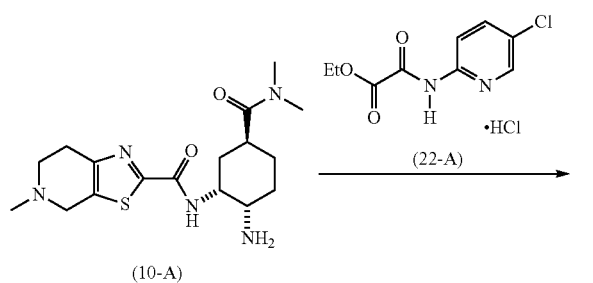

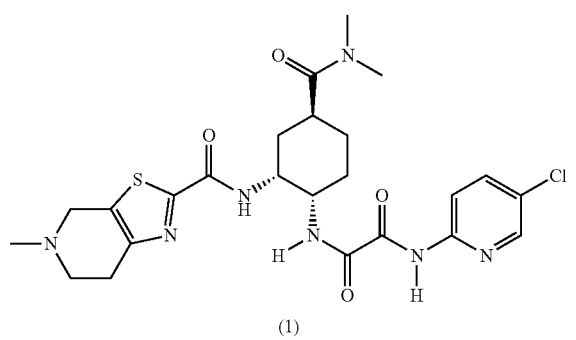

To a suspension of N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (440 mg, 1.203 mmol), 2-[(5-chloropyridin-2-yl)amino]-2-oxoacetate ethyl ester monohydrochloride (390 mg, 1.45 mmol) in acetonitrile (3 mL) was added triethylamine (0.9 mL, 6.1 mmol).

The mixture was heated in an oil bath at 60° C. for about 18 hours. Water (0.6 mL) was added and the solids were filtered, washed with water (2×3 mL) and dried in vacuo at 60° C. for 12 hours to afford N-1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (380 mg, 58% yield).

$^1$H-NMR (CDCl$_3$, 300 MHz) δ: 1.62-2.14 (6H, m), 2.52 (3H, s), 2.78-2.89 (3H, m), 2.89-2.95 (2H, m), 2.95 (3H, s), 3.06 (3H, s), 3.67 (1H, B of AB quartet, J=15.45 Hz), 3.75 (1H, A of AB quartet, J=15.45 Hz), 4.08-4.14 (1H, m), 4.67-4.71 (1H, m), 7.39 (1H, d, J=8.5 Hz), 7.69 (1H, dd, J=8.8, 2.4 Hz), 8.02 (1H, d, J=7.7 Hz), 8.17 (1H, d, J=8.8 Hz), 8.30 (1H, d, J=2.3 Hz), 9.72 (1H, broad s).

Example 21

Preparation of tert-butyl {(1S,2R,4S)-2-amino-4-[(dimethylamino)carbonyl]cyclohexyl}carbamate (Formula (8-A) wherein R$^2$=t-butyl or Formula (8-A1)

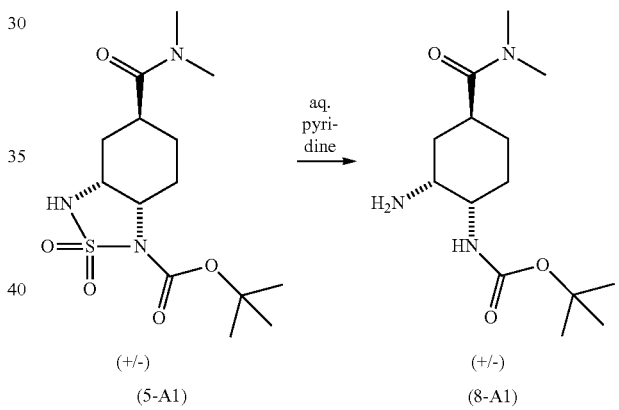

A suspension of racemic tert-butyl-(3aRS,5SR,7aSR)-5-(dimethylcarbamoyl)-2,2-dioxooctahydro-1H-2,1,3-benzothiadiazole-1-carboxylate (0.49 g, 1.4 mmol) in acetonitrile (2 mL) and aqueous pyridine (0.62 g, 61 wt %) was heated to reflux for 4 hours. The resulting reaction mixture was cooled to about 50° C. before addition of aqueous sodium chloride (10 wt %, 1 mL), toluene (5 mL), and sodium hydroxide (50 wt %, 0.5 mL). The mixture was then stirred for about 25 minutes before phase separation. The organic phase was concentrated in vacuo to dryness, affording tert-butyl{(1S,2R,4S)-2-amino-4-[(dimethylamino) carbonyl]cyclohexyl}carbamate (0.40 g, 100% yield).

$^1$H-NMR (CDCl$_3$) δ: 1.04-1.41 (1H, m), 1.45 (9H, s), 1.50-2.02 (5H, m), 2.78-2.91 (1H, m), 2.93 (3H, s), 3.05 (3H, s), 3.35 (1H, bs), 3.58 (1H, bs), 4.91 (1H, bs).

Racemic (5-A) was prepared according to the examples herein starting from racemic 3-cyclohexene-1-carboxylic acid.

Example 22

Preparation of tert-butyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (Formula (9-A) wherein R²=t-butyl or Formula (9-A1))

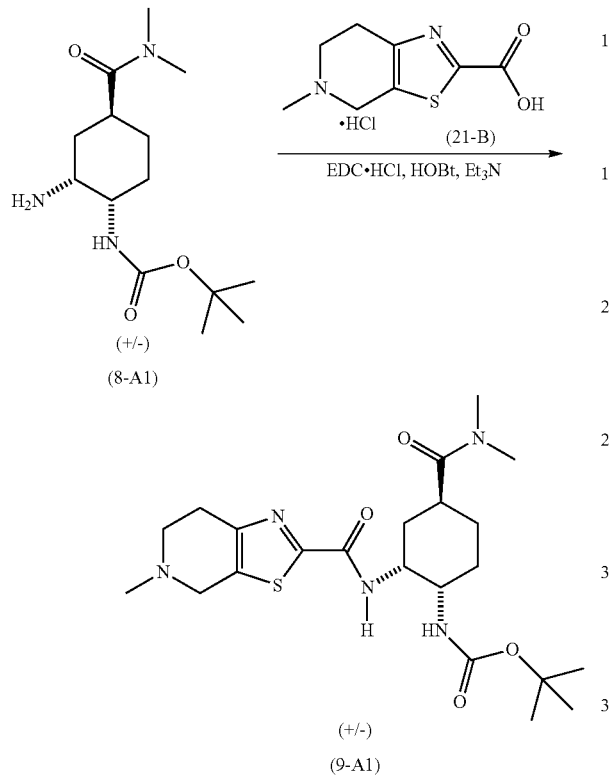

To a suspension of racemic tert-butyl-(3aRS,5SR,7aSR)-5-(dimethylcarbamoyl)-2,2-dioxooctahydro-1H-2,1,3-benzothiadiazole-1-carboxylate (100 mg, 0.35 mmol), 5-methyl-4,5,6,7-tetrahydro[1,3]thiazolo[5,4-c]pyridine-2-carboxylic acid hydrochloric acid salt (100 mg, 0.42 mmol), N-(3-dimethylaminopropyl)-N'-ethylcarbodiimide hydrochloride (85 mg, 0.42 mmol) and 1-hydroxybenzotriazole (10 mg, 0.07 mmol) in acetonitrile (2 mL), was added triethylamine (0.15 mL, 1.05 mmol). The reaction mixture was stirred at room temperature for about 14 hours. Following completion of the reaction (TLC), the solvent was evaporated in vacuo and the residue was dissolved in dichloromethane (15 mL). The solution was washed twice with saturated aqueous sodium bicarbonate solution (5 mL), and the organic layer was dried over anhydrous sodium sulfate, filtered and evaporated to dryness to afford the crude product, racemic tert-butyl {(1SR,2RS,4SR)-4-(dimethylcarbamoyl)-2-[(5-methyl-4,5,6,7-tetrahydro[1,3]thiazolo[5,4-c]pyridine-2-carbonyl)amino]cyclohexyl}carbamate as a foam (160 mg, 98% yield).

$^1$H-NMR (CDCl$_3$, 300 MHz) δ: 1.42 (9H, s), 1.69-2.09 (6H, m), 2.52 (3H, s), 2.71-2.97 (5H, m), 2.92 (3H, s), 3.01 (3H, s), 3.72-3.80 (3H, m), 4.57-4.61 (1H, m), 5.07 (1H, broad s), 7.35-7.38 (1H, m).

Example 23

Preparation of N1-(5-chloropyridin-2-yl)-N2-{(1SR,2RS,4SR)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (racemic Edoxaban (1))

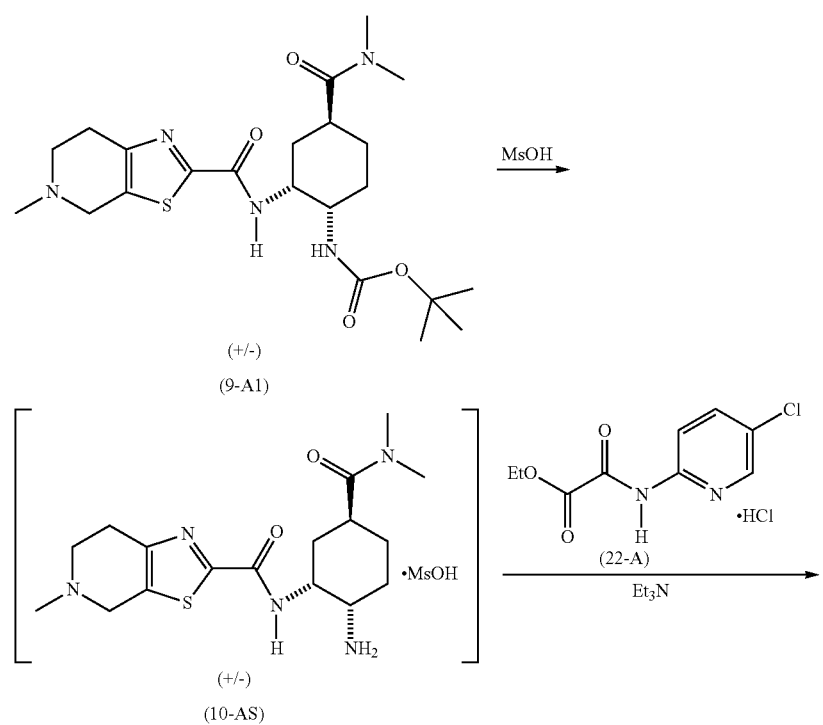

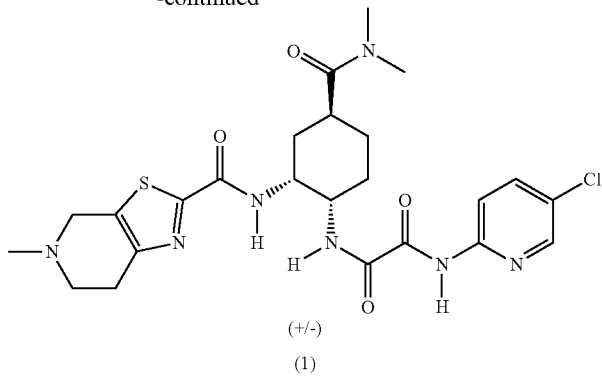

(1) (+/-)

To a solution of racemic tert-butyl {(1 SR,2RS,4SR)-4-(dimethylcarbamoyl)-2-[(5-methyl-4,5,6,7-tetrahydro[1,3]thiazolo[5,4-c]pyridine-2-carbonyl)amino]cyclohexyl}carbamate (160 mg, 0.343 mmol) in acetonitrile (2 mL) was added methanesulfonic acid (0.11 mL, 1.715 mmol) at room temperature. The reaction mixture was stirred at room temperature for 6 hours and following the completion of the deprotection (TLC), the reaction mixture was heated to 70° C. Triethylamine (1 mL, 6.86 mmol) and 2-[(5-chloropyridin-2-yl)amino]-2-oxoacetate ethyl ester monohydrochloride (95 mg, 0.343 mmol) were added and heating at 70° C. was continued for 11 hours. Water (5 drops) was added and the reaction mixture was cooled to room temperature. The resulting suspension was filtered and washed with a mixture of acetonitrile-water (1:1) (5 mL). The damp solids were dried in vacuo at about 55° C. (5 hours) to afford racemic N1-(5-chloropyridin-2-yl)-N2-{(1SR,2RS,4SR)-4-(dimethylcarbamoyl)-2-[(5-methyl-4,5,6,7-tetrahydro[1,3]thiazolo[5,4-c]pyridine-2-carbonyl)amino]cyclohexyl}ethanediamide at crystalline solid (40 mg).

$^1$H-NMR (CDCl$_3$, 300 MHz) δ: 1.62-2.14 (6H, m), 2.52 (3H, s), 2.78-2.89 (3H, m), 2.89-2.95 (2H, m), 2.95 (3H, s), 3.06 (3H, s), 3.67 (1H, B of AB quartet, J=15.45 Hz), 3.75 (1H, A of AB quartet, J=15.45 Hz), 4.08-4.14 (1H, m), 4.67-4.71 (1H, m), 7.39 (1H, d, J=8.5 Hz), 7.69 (1H, dd, J=8.8, 2.4 Hz), 8.02 (1H, d, J=7.7 Hz), 8.17 (1H, d, J=8.8 Hz), 8.30 (1H, d, J=2.3 Hz), 9.72 (1H, broad s).

Example 24

Preparation of 2-methyl-2-hexanyl [(1S,2R,4S)-2-amino-4-(dimethylcarbamoyl)cyclohexyl]carbamate (Formula (8-A2) wherein R$^2$=2-methyl-2-hexanyl or Formula (8-A2))

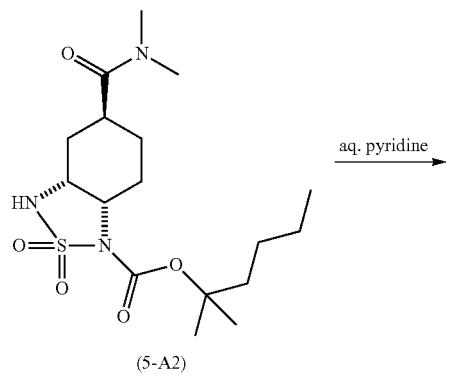

(5-A2)

aq. pyridine →

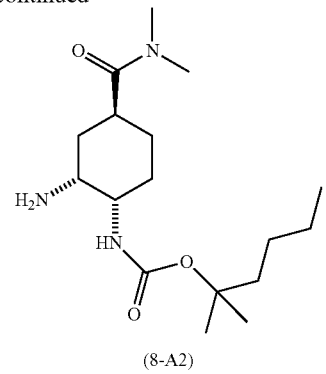

(8-A2)

To a suspension of the crude product from Example 12 in acetonitrile (10 mL) was added aqueous pyridine (4.15 g, 63 wt %), heated to reflux for 4 hours. The resulting reaction mixture was cooled to about 50° C. before addition of sodium chloride (10%, 8 mL), toluene (40 mL), and sodium hydroxide (50%, 3 mL). The mixture was then stirred for about 20 minutes. After phase separation, the organic phase was concentrated in vacuo to dryness, affording 2-methyl-2-hexanyl (1S,2R,5R))-2-amino-4-[(dimethylamino)carbonyl)]cyclohexylcarbamate, (2.92 g, 84% yield).

$^1$H-NMR (CDCl$_3$) δ: 0.89-0.92 (3H, m), 1.03 (2H, bs), 1.29-1.34 (5H, m), 1.42 (6H, s), 1.67-1.77 (5H, m), 2.76-2.86 (1H, m), 2.93 (3H, s), 3.05 (3H, s), 3.35 (1H. bs), 3.57 (1H, bs), 4.87 (NH, bs).

Example 25

Preparation of 2-methylhexan-2-yl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (Formula (9-A) wherein R$^2$=2-methyl-2-hexanyl or Formula (9-A2))

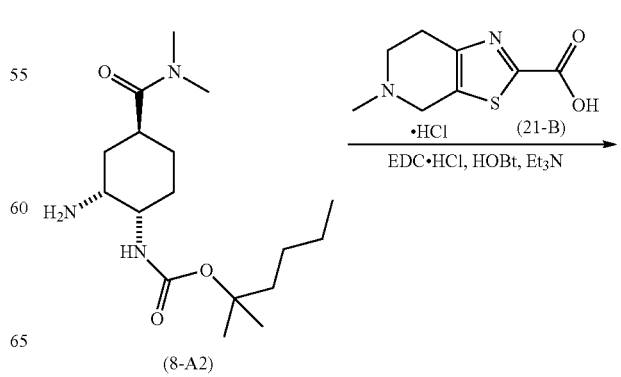

(8-A2)  (21-B)

EDC•HCl, HOBt, Et$_3$N →

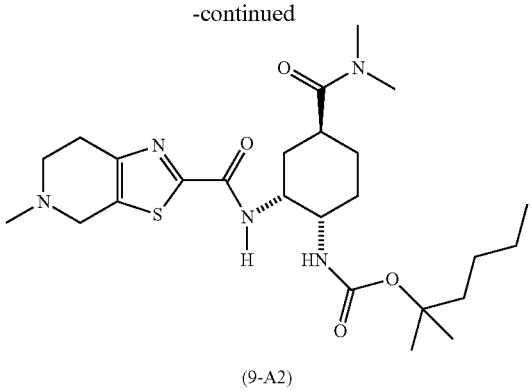

(9-A2)

To a suspension of 2-methyl-2-hexanyl(1S,2R,5R))-2-amino-4-[(dimethylamino) carbonyl)] cyclohexylcarbamate (1.0 g, ca. 90% purity by $^1$HNMR, 2.8 mmol), 5-methyl-4,5,6,7-tetrahydro[1,3]thiazolo[5,4-c]pyridine-2-carboxylic acid hydrochloric acid salt (1.0 g, 4.26 mmol), N-(3-dimethylaminopropyl)-N'-ethylcarbodiimide hydrochloride (850 mg, 4.43 mmol) and 1-hydroxybenzotriazole (100 mg, 0.74 mmol) in acetonitrile (5 mL), was added triethylamine (1.4 mL, 9.66 mmol). The reaction mixture was stirred at room temperature for about 20 hours. Following completion of the reaction (TLC), solvent was evaporated in vacuo and the residue was dissolved in dichloromethane (30 mL). The solution was washed twice with saturated aqueous sodium bicarbonate solution (15 mL), and the aqueous layer was extracted with dichloromethane (10 mL). The combined organic layer was dried over anhydrous sodium sulfate, filtered and evaporated to dryness. The residue was purified by flash chromatography over silica gel (2×18 cm), using 30% to 50% methanol-ethylacetate mixture, to afford 2-methylhexan-2-yl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (1.11 g, 78% yield) as a solid.

$^1$H-NMR (CDCl$_3$, 300 MHz) δ: 0.88 (3H, t, J=6.5 Hz), 1.13-1.28 (4H, m), 1.46 (6H, broad s), 1.46-1.56 (1H, m), 1.69-1.97 (6H, m), 2.06-2.10 (2H, m), 2.52 (3H, s), 2.69-2.81 (1H, m), 2.83-2.85 (2H, m), 2.88 (3H, m), 2.88-2.95 (1H, m), 2.96 (3H, m), 3.69-3.77 (3H, m), 4.57-4.61 (1H, m), 4.89 (1H, m), 7.25-7.29 (1H, m).

Example 26

Preparation of N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (Formula (1), Edoxaban)

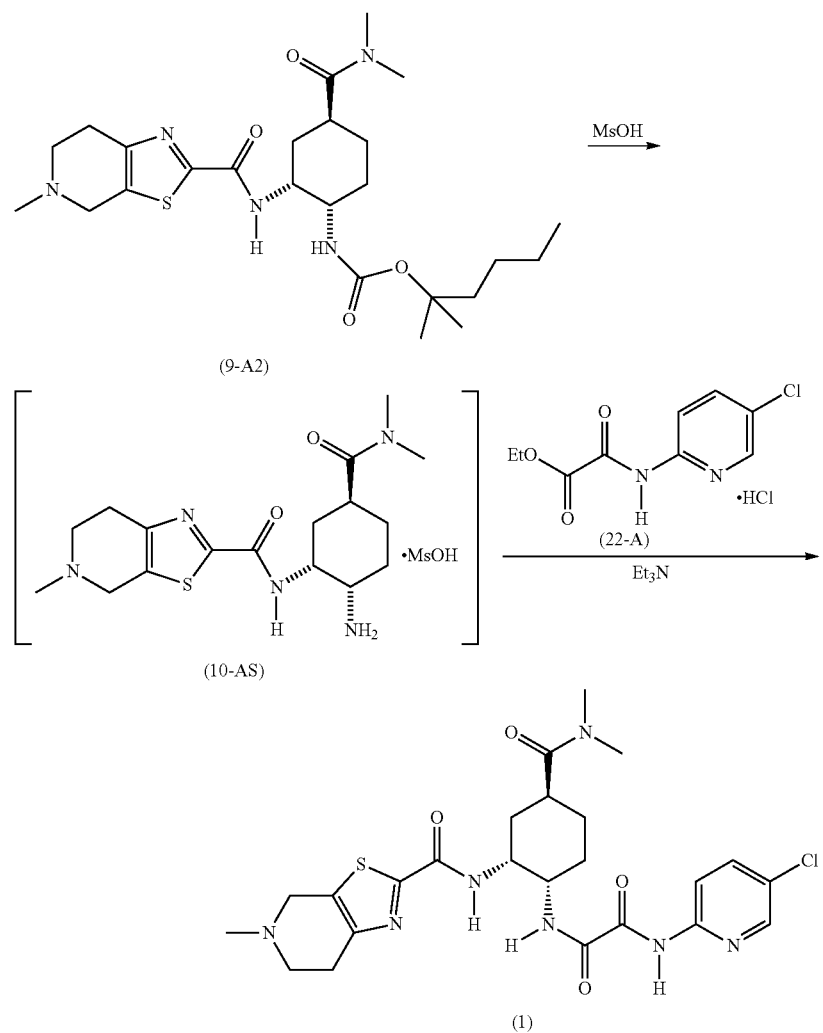

To a solution of 2-methylhexan-2-yl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (520 mg, 1.02 mmol) in acetonitrile (5 mL) was added methanesulfonic acid (0.4 mL, 5.1 mmol) at room temperature. The reaction mixture was stirred at room temperature for 10 hours and following the completion of the deprotection reaction (TLC), triethylamine (2.2 mL, 15.3 mmol) and 2-[(5-chloropyridin-2-yl)amino]-2-oxoacetate ethyl ester monohydrochloride (300 mg, 1.123 mmol) were added. The reaction mixture was heated to reflux for 20 hours. Water (0.5 mL) was added and the reaction mixture was cooled to room temperature. The resulting suspension was treated with a mixture of acetonitrile (4 mL) and water (1 mL). Most of the solids dissolved. The solvents were then evaporated to dryness and the residue was triturated with small quantities of ethyl acetate and water. The solid was collected by filtration, washed with water and then ethyl acetate to yield a sticky solid. $^1$HNMR (CDCl$_3$) corresponded with the mesylate salt of the compound of Formula (1). A small sample was free-based with aqueous sodium bicarbonate to afford N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethane diamide.

$^1$H-NMR (CDCl$_3$, 300 MHz) δ: 1.62-2.14 (6H, m), 2.52 (3H, s), 2.78-2.89 (3H, m), 2.89-2.95 (2H, m), 2.95 (3H, s), 3.06 (3H, s), 3.67 (1H, B of AB quartet, J=15.45 Hz), 3.75 (1H, A of AB quartet, J=15.45 Hz), 4.08-4.14 (1H, m), 4.67-4.71 (1H, m), 7.39 (1H, d, J=8.5 Hz), 7.69 (1H, dd, J=8.8, 2.4 Hz), 8.02 (1H, d, J=7.7 Hz), 8.17 (1H, d, J=8.8 Hz), 8.30 (1H, d, J=2.3 Hz), 9.72 (1H, broad s).

Example 27

Preparation of 2-trimethylsilylethyl (1S,2R,5R)-2-amino-4-[(dimethylamino)carbonyl]cyclohexylcarbamate (Formula (8-A) wherein R$^2$=2-trimethylsilylethyl or Formula (8-A3)

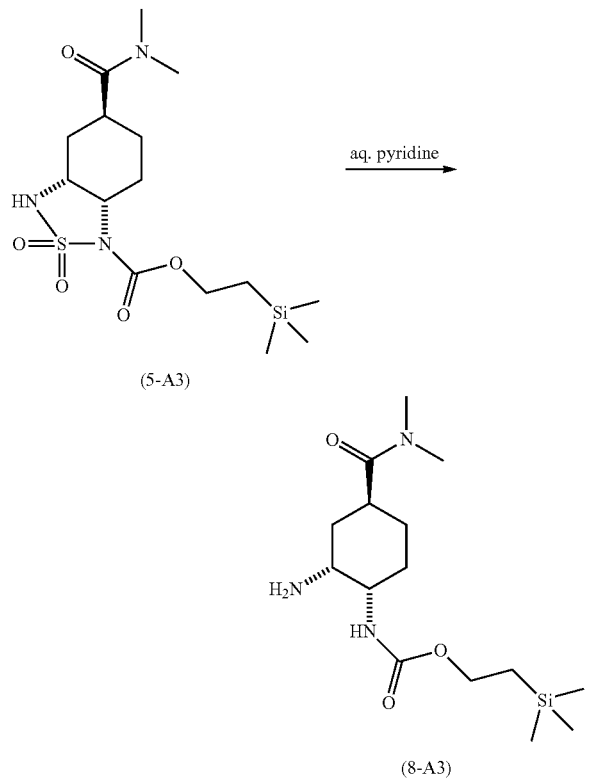

A mixture of crude product from Example 13 (1.42 g), acetonitrile (5 mL), and aqueous pyridine (8 mL, 63%) was heated to 85° C. for 4 hours. Following cooling to room temperature, sodium carbonate solution (6% w/w 7.43 g, 4.1 mmol) and dichloromethane (16 mL) were added and the mixture stirred vigorously for 30 minutes. Phase separation afforded an aqueous phase which was extracted with dichloromethane (50 mL). The extract was concentrated to 10 mL, diluted with toluene and concentrated again (3×30-40 mL), and finally concentrated to dryness, achieving a residue, 2-trimethylsilylethyl (1S,2R,5R)-2-amino-4-[(dimethylamino)carbonyl]cyclohexylcarbamate, (0.78 g) which was used in the next step without purification.

$^1$H-NMR (CDCl$_3$) δ: 0.04 (9H, s), 0.95-1.01 (2H, m), 1.57-2.04 (7H, m), 2.93 (3H, s), 3.05 (3H, s), 3.40 (1H, bs), 3.64 (1H, bs), 4.12-4.17 (2H, m), 5.08 (NH, bs).

Example 28

Preparation of 2-(trimethylsilyl)ethyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (Formula (9-A) wherein R$^2$=2-trimethylsilylethyl) or Formula (9-A3)

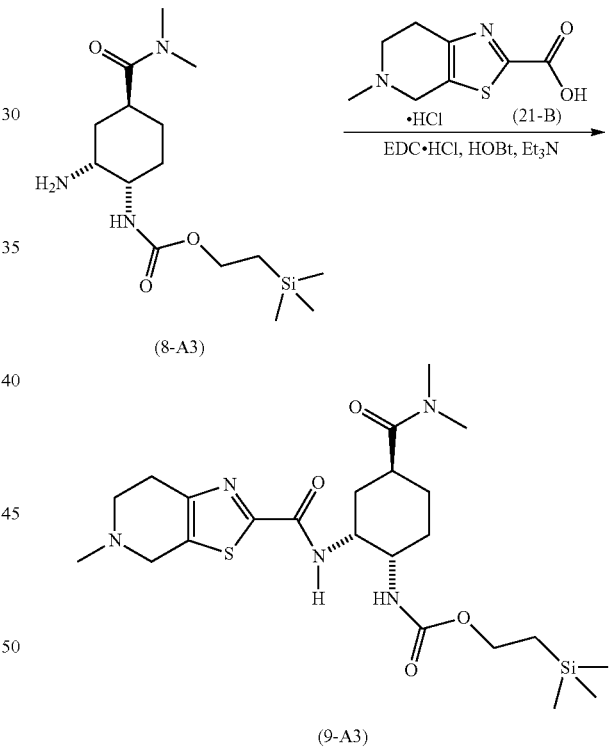

A suspension of 2-(trimethylsilyl)ethyl [(1S,2R,4S)-2-amino-4-(dimethylcarbamoyl)cyclohexyl]carbamate (0.77 g, 2.34 mmol), 5-methyl-4,5,6,7-tetrahydro[1,3]thiazolo[5,4-c]pyridine-2-carboxylic acid hydrochloric acid salt (0.66 g, 2.80 mmol), EDC.HCl (0.58 g, 3.04 mm), hydroxybenzotriazole (0.32 g, 2.34 mmol), dichloromethane (6 mL), and triethylamine (0.71 g, 7.02 mmol) was stirred at room temperature for 17 hours. Following the completion of the reaction, the thin suspension was washed with a saturated aqueous sodium bicarbonate solution (2×3 mL). The organic phase was then washed with a saturated aqueous sodium chloride solution (3 mL). The organic phase was dried over anhydrous sodium sulfate and concentrated in vacuo at about 35° C. to dryness to yield 1.06 g of a yellow solid. To the flask containing the yellow solid was added acetonitrile (2.3 mL) to form a thin suspension which was stirred at room temperature for 1 hour. The suspension was diluted with methyl tert-butyl ether (0.8 mL) and cooled to about 0° C. for 3.5 hours. The product was then collected by filtration, washed with methyl tert-butyl ether (2×1.5 mL), and dried in vacuo at room temperature to afford 2-(trimethylsilyl)ethyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (0.45 g, 38% yield).

$^1$H-NMR (CDCl$_3$, 300 mHz) δ: 0.00 (9H, s), 0.94 (2H, t, J=8.1 Hz), 1.48 (1H, apparent dq, J=4.3 Hz, 12.8 Hz), 1.61-2.19 (6H, m), 2.51 (3H, s), 2.65-2.79 (1H, m), 2.80-2.88 (2H, m), 2.91 (4H, s), 2.99 (3H, s), 3.70 (1H, s), 3.79 (2H, broad s), 4.11 (2H, t, J=8.1 Hz), 4.57 (1H, apparent dd, J=3.7 Hz, 8.1 Hz), 5.10 (1H, s), 7.28 (1H, d, J=8.6 Hz).

Example 29

Preparation of N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (Formula (10-A)

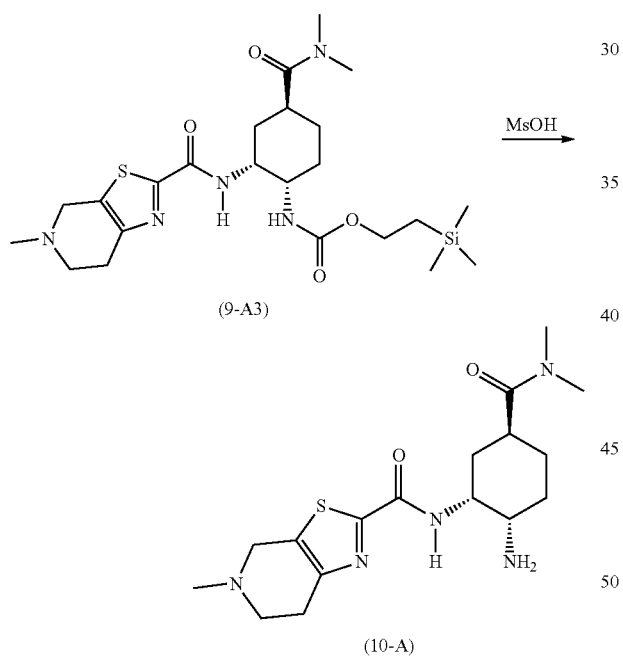

A suspension of 2-(trimethylsilyl)ethyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (0.45 g, 0.88 mmol) and methanesulfonic acid (0.34 g, 3.53 mmol) in acetonitrile (1.4 ml) was stirred at room temperature for 5 hours. Gas and heat evolution was observed during the addition of methanesulfonic acid. Following the completion of the reaction, the reaction solution was concentrated in vacuo at about 35° C. to dryness. The residue was dissolved in dichloromethane (8 mL) at room temperature and treated with saturated aqueous sodium bicarbonate solution (4 mL) at which point the evolution of CO$_2$ was observed. The aqueous phase was saturated with sodium chloride and sodium bicarbonate and the biphasic suspension was stirred at room temperature for 10 minutes. The suspension was filtered and washed with dichloromethane (1 mL). The aqueous and organic phases of the filtrate were separated, and the aqueous phase was extracted with dichloromethane (4×6 mL). The combined organic phases were dried over anhydrous sodium sulfate and concentrated in vacuo at about 35° C. to afford N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (0.060 g, 32% yield).

Example 30

Preparation of 1-methyl cyclohexyl {(1S,2R,4S)-2-amino-4-[(dimethylamino)carbonyl]cyclohexyl}carbamate (Formula (8-A) wherein R$^2$=1-methylcyclohexyl or Formula (8-A4))

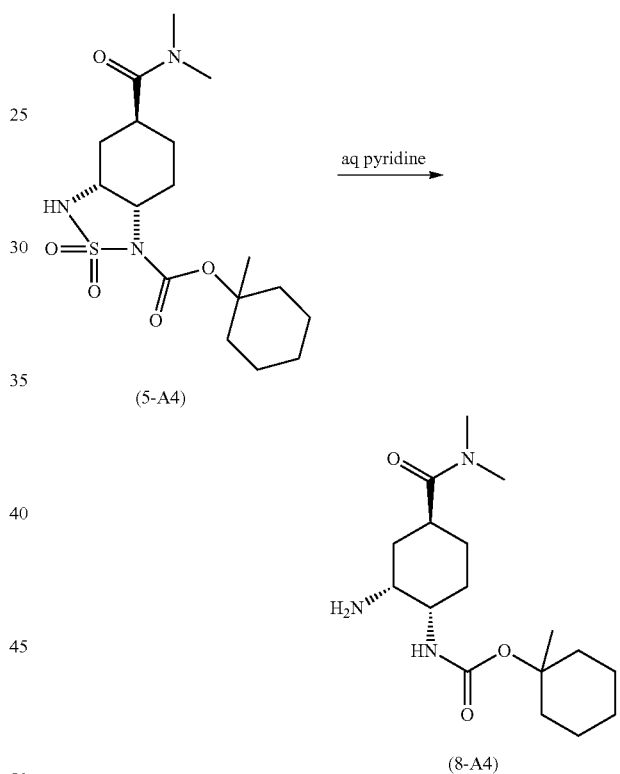

A solution of 1-methyl cyclohexyl (3aR,5S,7aS)-5-(dimethylcarbamoyl)-2,2-dioxooctahydro-1H-2,1,3-benzothiadiazole-1{3H}-carboxylate (8.40 g, 21.7 mmol), and aqueous pyridine (12.1 mL, 99.7 mmol, 65%) in acetonitrile (34 mL) was heated to 85° C. for 4 hours. Following the completion of the reaction the solution was cooled to room temperature at which point a thick suspension was obtained. To this suspension was added dichloromethane (92 mL) and a solution of sodium carbonate (2.53 g, 23.9 mmol) in water (42 mL) and the biphasic mixture was stirred vigorously. The aqueous and organic phases were separated, the aqueous phase was extracted with dichloromethane (32 mL) and concentrated in vacuo at about 35° C. to yield 1-methyl cyclohexyl {(1S,2R,4S)-2-amino-4-[(dimethylamino) carbonyl] cyclohexyl}carbamate (6.68 g, 95% yield) as a white solid.

$^1$H-NMR (CDCl$_3$, 300 MHz) δ: 1.30-1.82 (13H, m), 1.48 (3H, s), 1.88 (1H, dt, J=3.3, 13.2 Hz), 2.02-2.20 (2H, m), 2.79-2.94 (1H, m), 2.93 (3H, s), 3.06 (3H, m). 3.37 (1H, apparent q, J=3.2 Hz) 3.50-3.64 (1H, m), 5.01 (1H, broad d, J=7.6 Hz).

Example 31

Preparation of Salts of 1-methylcyclohexyl {(1S,2R,4S)-2-amino-4-[(dimethylamino)carbonyl]cyclohexyl}carbamate (salt of Formula (8A) wherein R$^2$=1-methylcyclohexyl or Formula (8-A4S))

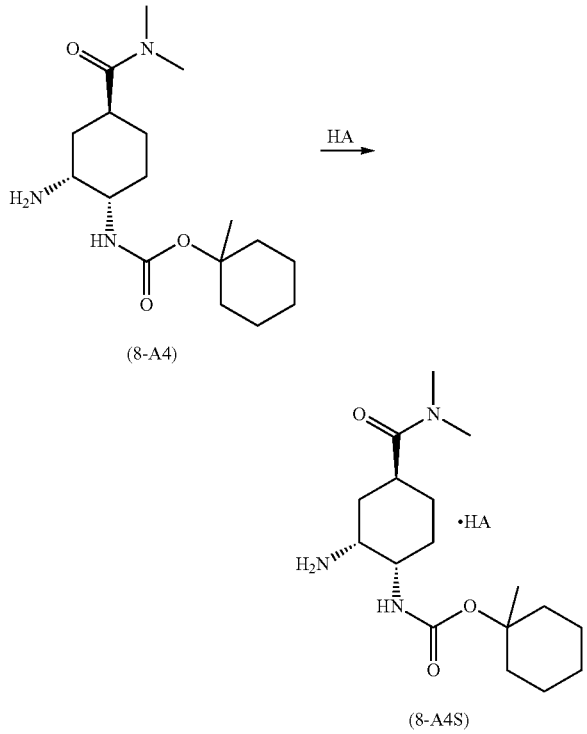

Example 31a

Preparation of (R)-camphorsulfonate salt (HA=(R)-camphorsulfonic acid)

A mixture of 1-methyl cyclohexyl {(1S,2R,4S)-2-amino-4-[(dimethylamino) carbonyl] cyclohexyl}carbamate (0.50 g, 1.5 mmol, HPLC purity=96.6 area %) and (R)-camphor sulfonic acid (0.35 g, 1.5 mmol) in ethyl acetate (5 mL) was stirred at room temperature for 16 hours. The suspension was filtered and dried to yield 1-methyl cyclohexyl {(1S,2R,4S)-2-amino-4-[(dimethylamino)carbonyl]cyclohexyl}carbamate (R)-camphor sulfonate (0.75 g, 90% yield, HPLC purity=99.94 area %).

$^1$H-NMR (DMSO-d6, 300 MHz) δ:0.74 (3H, s), 1.05 (3H, s), 1.21-1.36 (3H, m), 1.37-1.54 (7H, m), 1.43 (3H, s), 1.55-1.66 (3H, m), 1.66-2.13 (8H, m), 2.23 (1H, dt, J=3.6, 17.7 Hz), 2.36 (1H, A of AB system, J=14.7 Hz), 2.70 (1H, apparent t, J=11.0 Hz), 2.80 (3H, s), 2.86 (1H, B of AB system, J=14.7 Hz), 2.93-3.08 (1H, m), 3.00 (3H, s), 3.64-3.53 (2H, m), 6.91 (1H, d, J=6.0 Hz), 7.50 (3H, broad s).

Example 31b

Preparation of p-toluenesulfonate salt (HA=p-toluene sulfonic acid)

A mixture of 1-methyl cyclohexyl {(1S,2R,4S)-2-amino-4-[(dimethylamino)carbonyl]cyclohexyl}carbamate (0.50 g, 1.5 mmol, HPLC purity=96.6 area %) and p-toluenesulfonic acid (0.28 g, 1.5 mmol) in ethyl acetate (5 mL) was stirred at room temperature for 16 hours. The suspension was filtered and dried to afford 1-methyl cyclohexyl {(1S,2R,4S)-2-amino-4-[(dimethylamino) carbonyl] cyclohexyl}carbamate p-toluenesulfonate (0.71 g, 93% yield, HPLC purity=99.91 area %).

$^1$H-NMR (DMSO-d6, 300 MHz) δ: 1.2-2.16 (18H, m), 1.43 (3H, s), 2.28 (3H, s), 2.92-3.05 (1H, m), 2.99 (3H, s), 3.34 (3H, s), 3.61 (2H, broad s), 3.94 (1H, broad d, J=5.6 Hz), 7.11 (2H, d, J=7.9 Hz), 7.47 (2H, d, J=8.1 Hz), 7.73 (3H, broad s).

Example 31c

Preparation of meso-tartrate salt (HA=meso-tartaric acid)

A mixture of 1-methyl cyclohexyl {(1S,2R,4S)-2-amino-4-[(dimethylamino)carbonyl]cyclohexyl}carbamate (0.50 g, 1.5 mmol, HPLC purity=96.6 area %) and meso-tartaric acid (0.25 g, 1.5 mmol) in ethyl acetate (5 mL) was stirred at room temperature for 16 hours. The suspension was then filtered and dried to afford 1-methyl cyclohexyl {(1S,2R,4S)-2-amino-4-[(dimethylamino)carbonyl]cyclohexyl}carbamate meso-tartrate (0.60 g, 80% yield, HPLC purity=97.98 area %)

$^1$H-NMR (DMSO-d6, 300 MHz) δ: 1.21-1.88 (14H, m), 1.43 (3H, s), 1.89-2.14 (2H, m), 2.80 (3H, s), 2.93-3.08 (1H, m), 3.00 (3H, s), 3.24 (2H, broad s), 3.58 (2H, broad s), 3.93 (2H, s), 6.96 (1H, broad d, J=5.3 Hz), 8.47 (4H, broad s).

Example 31d

Preparation of benzoate salt (HA=benzoic acid)

A mixture of 1-methyl cyclohexyl {(1S,2R,4S)-2-amino-4-[(dimethylamino) carbonyl] cyclohexyl}carbamate (0.50 g, 1.5 mmol, HPLC purity=96.6 area %) and benzoic acid (0.18 g, 1.5 mmol) in ethyl acetate (5 mL) was stirred at room temperature for 16 hours. The suspension was then filtered and dried to yield 1-methyl cyclohexyl {(1S,2R,4S)-2-amino-4-[(dimethylamino)carbonyl]cyclohexyl}carbamate benzoate (0.60 g, 91% yield, HPLC purity=98.33 area %).

$^1$H-NMR (DMSO-d6, 300 MHz) δ: 1.12-1.76 (14H, m), 1.39 (3H, s), 1.91-2.08 (2H, m), 2.78 (3H, s), 2.83-3.08 (1H, m), 3.00 (3H, s), 3.19-3.28 (1H, m), 3.34-3.48 (1H, m), 6.95 (1H, broad d, J=7.8 Hz), 7.43 (2H, apparent t, J=7.3 Hz), 7.52 (1H, apparent t, J=7.3 Hz), 7.93 (2H, d, J=6.9 Hz).

Example 31e

Preparation of citrate salt (HA=citric acid)

A mixture of 1-methyl cyclohexyl {(1S,2R,4S)-2-amino-4-[(dimethylamino)carbonyl]cyclohexyl}carbamate (0.50 g, 1.5 mmol, HPLC purity=96.6 area %) and citric acid (0.28 g, 1.5 mmol) in acetonitrile (4.5 mL) and water (0.5 mL) was stirred at room temperature for 16 hours. The suspension was then filtered and dried to yield 1-methyl cyclohexyl {(1S,2R,4S)-2-amino-4-[(dimethylamino)carbonyl]cyclohexyl}carbamate citrate (0.74 g, 97% yield, HPLC purity=99.94 area %).

$^1$H-NMR (DMSO-d6, 300 MHz) δ: 1.20-1.87 (14H, m), 1.43 (3H, s), 1.87-2.12 (2H, m), 2.49 (2H, A of AB system, J=15.1 Hz), 2.55 (2H, B of AB system, J=15.1 Hz), 2.80 (3H, s), 2.94-3.06 (1H, m), 3.00 (3H, s), 3.55-3.67 (3H, m), 6.96 (1H, broad d, J=5.8 Hz), 9.54 (5H, broad s).

Example 32

1-methyl cyclohexyl {(1S,2R,4S)-2-amino-4-[(dimethylamino)carbonyl]cyclohexyl}carbamate citrate (Formula (8-A) wherein $R^2$=1-methylcyclohexyl or Formula (8-A4S) wherein HA=citric acid)

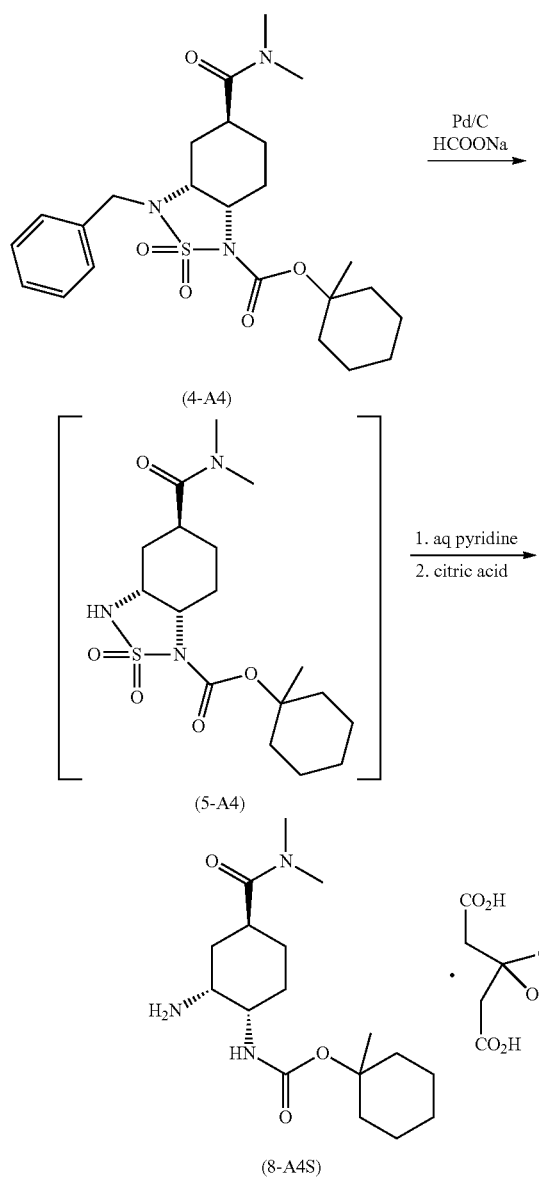

A suspension of 1-methyl cyclohexyl (3aR,5S,7aS)-3-benzyl-5-(dimethylcarbamoyl)-2,2-dioxooctahydro-1H-2,1,3-benzothiadiazole-1-carboxylate (52.21 g, 109.4 mmol), sodium formate (22.32 g, 328.2 mmol), and palladium on carbon (10.5 g, 10 wt % Pd, 66% wet) in methanol (370 mL) and water (150 mL) was heated to about 55° C. for 2.5 hours. Following the completion of the reaction, the suspension was cooled to room temperature and dichloromethane (200 mL) was charged. The suspension was filtered through a pad of diatomaceous earth and washed with dichloromethane (100 mL). The biphasic solution was concentrated in vacuo at about 35° C. to a volume of 150 mL. To this solution was added dichloromethane (200 mL) and the aqueous and organic phases were separated. The aqueous phase was extracted with dichloromethane (100 mL) and the combined organic phases were concentrated in vacuo at about 35° C. to 100 mL. Acetonitrile (200 mL) was added and the solution concentrated in vacuo at about 35° C. to 100 mL. This was repeated twice more to afford 1-methyl cyclohexyl (3aR,5, S7aS)-5-(dimethylcarbamoyl)-2,2-dioxooctahydro-1H-2,1,3-benzothiadiazole-1{3H}-carboxylate in acetonitrile. The solution was transferred to a clean flask, diluted with acetonitrile (150 mL) and aqueous pyridine (61 mL, 503.2 mmol, 65%) and heated to 85° C. for 4 hours. Following the completion of the reaction, the solution was cooled to room temperature at which point a thick suspension was obtained. To this suspension was added dichloromethane (450 mL) and a solution of sodium carbonate (12.65 g, 120.3 mmol) in water (210 mL) and the biphasic mixture was stirred vigorously. Following phase separation, the aqueous phase was extracted with dichloromethane (150 mL) and the organic phase concentrated in vacuo at about 35° C. to 75 mL. Toluene (150 mL) was added and the solution was concentrated in vacuo at about 35° C. to 75 mL. The operation was repeated twice more. To the resulting solution was added acetonitrile (450 mL), water (52 mL) and citric acid (21.1 g, 328.2 mmol). After stirring for 30 minutes seeds of (8-A4S) were charged to initiate precipitation and the suspension stirred at room temperature for 6 hours. The product was collected by filtration, washed with acetonitrile (100 mL) and dried in vacuo at 50° C. to afford 1-methyl cyclohexyl {(1S,2R,4S)-2-amino-4-[(dimethylamino)carbonyl]cyclohexyl}carbamate citrate (43.27 g, 76% yield from Formula (4-A4) as a white solid.

The free base form of Formula (8-A4) was prepared by stirring the citrate salt (2.00 g, 3.86 mmol) in a mixture of dichloromethane (10 mL) and aqueous sodium carbonate (0.67 g in 10 mL water) for 1 hour. The aqueous and organic phases were separated, the aqueous phase was extracted with dichloromethane (2×10 mL) and the combined organic extracts concentrated in vacuo at about 35° C. to afford 1-methyl cyclohexyl {(1S,2R,4S)-2-amino-4-[(dimethylamino)carbonyl]cyclohexyl}carbamate (1.26 g, 100% yield).

Example 33

Preparation of 1-methylcyclohexyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (Formula (9-A) wherein $R^2$=1-methylcyclohexyl or Formula (9-A4))

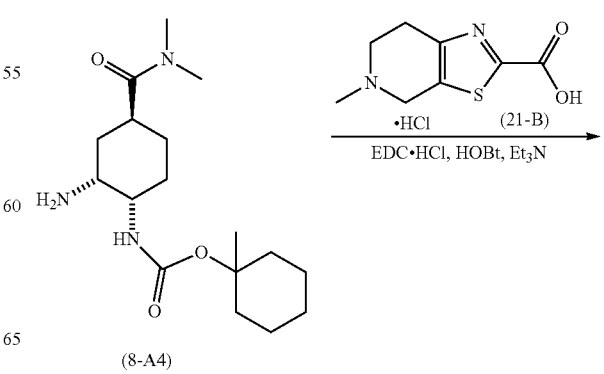

-continued

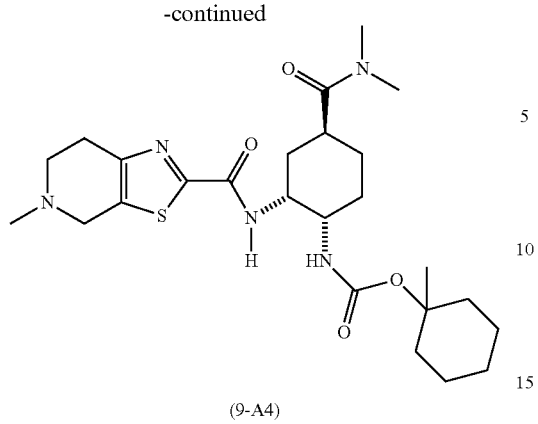

(9-A4)

To a suspension of 1-methyl cyclohexyl {(1S,2R,4S)-2-amino-4-[(dimethylamino)carbonyl]cyclohexyl}carbamate (6.5 g, ca. 97% purity by $^1$HNMR, 19.37 mmol), 5-methyl-4,5,6,7-tetrahydro[1,3]thiazolo[5,4-c]pyridine-2-carboxylic acid hydrochloric acid salt (5.46 g, 23.25 mmol), N-(3-dimethylaminopropyl)-WV-ethylcarbodiimide hydrochloride (4.83 g, 25.18 mmol) and 1-hydroxybenzotriazole (2.62 g, 19.37 mmol) in dichloromethane (42 mL), was added triethylamine (8.1 mL, 58.11 mmol). The reaction mixture was stirred at room temperature for about 20 hours. Following completion of the reaction (TLC), the reaction mixture was washed twice with saturated aqueous sodium bicarbonate solution (25 mL), and then with brine (20 mL). The organic layer was dried over anhydrous sodium sulfate, filtered and evaporated to dryness to yield a foam (11.08 g). The crude product was dissolved in acetonitrile (20 mL) and immediately a thick suspension was formed. Methyl t-butyl ether (5 mL) was added and the suspension was cooled in an ice bath and stirred for 1 hour. The solids were filtered and washed with cold (about 0° C.) methyl t-butyl ether (8 mL). The damp cake was dried in vacuo at room temperature for 18 hours to afford 1-methylcyclohexyl {(1S,2R,4S)-4-(dimethylcarbamoyl)-2-[(5-methyl-4,5,6,7-tetrahydro[1,3]thiazolo[5,4-c]pyridine-2-carbonyl)amino] cyclohexyl}carbamate as a crystalline solid (7.28 g, 74% yield; HPLC=99.9 area %). A second crop of 600 mg, 6% yield was obtained from acetonitrile (3 mL).

$^1$H-NMR (CDCl$_3$, 300 MHz) δ: 1.21-1.26 (1H, m), 1.35-1.59 (11H, m), 1.75-2.01 (3H, m), 2.06-2.10 (4H, m), 2.52 (3H, s), 2.69-2.88 (3H, m), 2.90 (3H, s), 2.90-2.94 (2H, m), 2.96 (3H, s), 3.0-3.78 (3H, m), 4.59-4.63 (1H, m), 4.96 (broad s, 1H), 7.33-7.35 (1H, m).

Example 34

Preparation of N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide monohydrochloride (Formula (10-AS) wherein HA=hydrochloric acid)

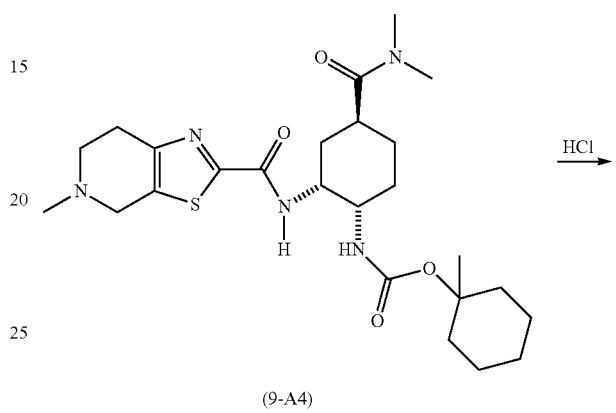

(9-A4)

HCl ⟶

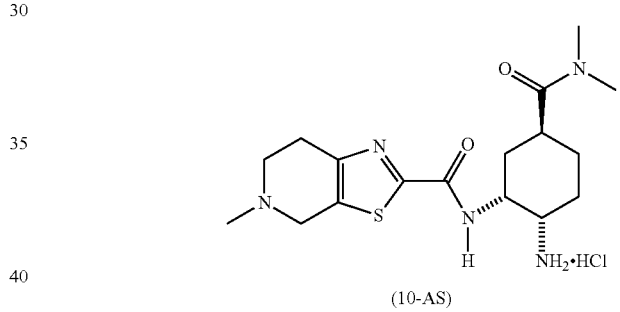

(10-AS)

To a suspension of 1-methylcyclohexyl {(1S,2R,4S)-4-(dimethylcarbamoyl)-2-[(5-methyl-4,5,6,7-tetrahydro[1,3] thiazolo[5,4-c]pyridine-2-carbonyl)amino] cyclohexyl}carbamate (600 mg, 1.186 mmol) in acetonitrile (2.5 mL) was added 4M hydrogen chloride in dioxane (1.5 mL, 5.93 mmol) at room temperature. A momentary clear solution turned into a thick suspension. The suspension was stirred at room temperature for 6 hours and the solids were filtered, washed with methyl t-butyl ether (5 mL) and dried in vacuo at room temperature to afford crystalline, white, hygroscopic solids (620 mg). A small sample was partitioned between aqueous sodium bicarbonate and chloroform to afford N-[(1R,2S,5S)-2-amino-5-(dimethylcarbamoyl)cyclohexyl]-5-methyl-4,5,6,7-tetrahydro[1,3]thiazolo[5,4-c] pyridine-2-carboxamide.

$^1$H-NMR free base (CDCl$_3$, 300 mHz) δ: 1.48 (1H, apparent dq, J=4.5 Hz, 12.0 Hz), 1.73-1.89 (4H, m), 2.35 (1H, broad d, J=14.0 Hz), 2.51 (3H, s), 2.67-2.89 (3H, m), 2.90-2.98 (2H, m), 2.92 (3H, s), 2.99 (3H, s), 3.10-3.19 (1H, m), 3.71 (2H, s), 4.25 (1H, broad s), 7.39 (1H, d, J=6.2 Hz).

Example 35

Preparation of N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (Formula (10-A))

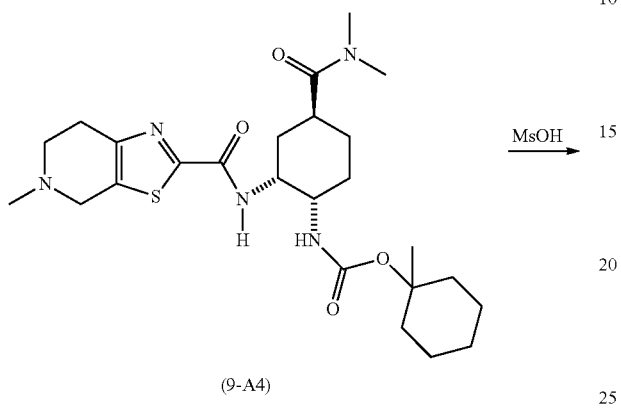

To a suspension of 1-methylcyclohexyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (4.0 g, 7.91 mmol) in acetonitrile (12 mL) was added methanesulfonic acid (2.05 mL, 31.64 mmol) at room temperature. The reaction mixture became exothermic with gas evolution. The reaction mixture was stirred at room temperature for 0.5 hours and following the completion of reaction (TLC), the solvent was evaporated and the residue was dissolved in dichloromethane (100 mL). The organic layer was treated with saturated aqueous sodium bicarbonate (50 mL) and solid sodium chloride (10 g). The organic layer was separated and the aqueous mixture was extracted with dichloromethane (3×30 mL). The combined organic layer was dried over anhydrous sodium sulfate, filtered and evaporated to dryness to yield N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide as a foam (2.88 g, 99% yield).

Example 36

Preparation of N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (R)-camphorsulfonate (salt of formula (10-AS) wherein HA=(R)-camphorsulfonic acid)

To a solution of N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (300 mg, 0.821 mmol) in ethylacetate (1 mL) was added a hot (about 65° C.) solution of (R)-camphor sulfonic acid (191 mg, 0.821 mmol). A gummy mass separated out. The reaction flask was heated in a water bath (about 50° C.) for about 25 minutes and a white suspension was formed. The suspension was cooled to room temperature and filtered, washed with ethyl acetate and dried in vacuo at room temperature to yield N-[(1R,2S,5S)-2-amino-5-(dimethylcarbamoyl)cyclohexyl]-5-methyl-4,5,6,7-tetrahydro[1,3]thiazolo[5,4-c]pyridine-2-carboxamide (R)-camphorsulfonate as a white solid (480 mg, 98% yield).

$^1$H-NMR (CDCl$_3$, 300 mHz) δ: 0.76 (3H, s), 1.0 (3H, s), 1.28-1.36 (1H, m), 1.53-1.69 (2H, m), 1.78-2.05 (7H, m), 2.13-2.28 (2H, m), 2.42-2.51 (1H, m), 2.61-2.67 (2H, m), 2.63 (3H, s), 2.91 (3H, s), 3.05 (3H, s), 2.91-3.10 (5H, m), 3.55-3.60 (1H, m), 3.89 (2H, broad s), 4.77-4.79 (1H, m), 4.8-6.75 (3H, very broad peak), 7.95 (1H, d, J=8.5 Hz).

Example 37

Preparation of N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (Formula (1), Edoxaban)

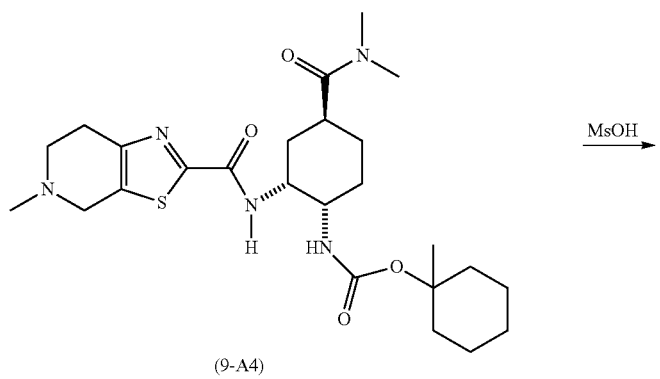

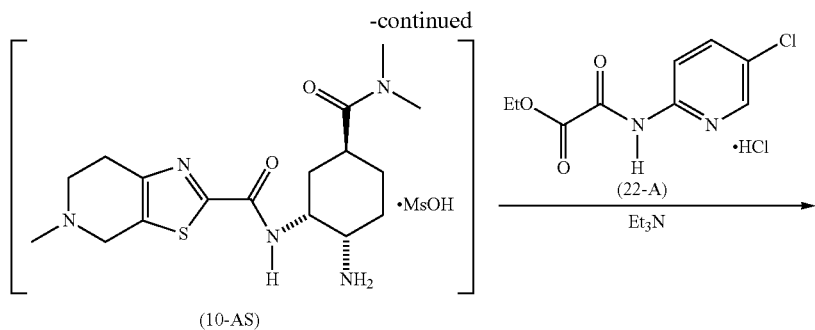

To a solution of crude 1-methylcyclohexyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (850 mg, 1.5 mmol) in acetonitrile (3 mL) was added methanesulfonic acid (0.3 mL, 4.5 mmol). The reaction mixture was stirred at room temperature for 10 hours and the solvent was distilled off. 2-[(5-Chloropyridin-2-yl)amino]-2-oxoacetate ethyl ester monohydrochloride (480 mg, 1.8 mmol), acetonitrile (3 mL) and triethylamine (1.3 mL, 9.0 mmol) were added. The reaction mixture was heated in an oil bath at 70° C. for 26 hours and cooled to room temperature. A mixture of acetonitrile (2 mL) and water (2 mL) was added and cooled in an ice bath. The solids were filtered, washed with acetonitrile-water (1:1, 4 mL) and dried in vacuo at 50° C. for 18 hours to afford N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (440 mg, 54% yield).

Example 38

Preparation of N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (Edoxaban(1))

To a solution of 1-methylcyclohexyl {(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}carbamate (2.22 g, 4.39 mmol) in acetonitrile (3 mL) was added methanesulfonic acid (1.2 mL, 17.6 mmol). The reaction mixture was exothermic with gas evolution. The reaction was stirred at room temperature for 4 hours and $^1$H NMR analysis of an aliquot indicated the completion of the deprotection reaction. 2-[(5-Chloropyridin-2-yl)amino]-2-oxoacetate ethyl ester monohydrochloride (1.4 g, 5.27 mmol), and triethylamine (4.9 mL, 35.12 mmol) were carefully added as fumes were formed. The reaction mixture was heated in an oil bath at 70° C. for 20 hours and cooled to room temperature. Water (6 mL) was added and the mixture cooled in an ice bath. The solids were filtered, washed with acetonitrile-water (1:5, 10 mL) and dried in vacuo at 50° C. for 18 hours to afford N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (2.0 g, 83% yield).

Example 29

Preparation of N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide p-toluene sulfonic acid mono hydrate (Edoxaban tosylate monohydrate)

To a suspension of N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide (1.0 g, 1.82 mmol) in absolute ethanol (6 mL) and water (2 mL) was added p-toluene sulfonic acid monohydrate (365 mg, 1.91 mmol). A thick suspension was formed. The suspension was heated in an oil bath at 75° C. for 2 hours and then cooled to room temperature. The solids were filtered and washed with ethanol (2×5 mL) to afford N1-(5-chloropyridin-2-yl)-N2-{(1S,2R,4S)-4-(dimethylcarbamoyl)-2-[(5-methyl-4,5,6,7-tetrahydro[1,3]thiazolo[5,4-c]pyridine-2-carbonyl)amino]cyclohexyl}ethanediamide p-toluene sulfonic acid mono hydrate (1.32 g, 98% yield) as a crystalline white solid, 99.3 area % purity by HPLC.

What is claimed is:

1. A compound of Formula (9-A):

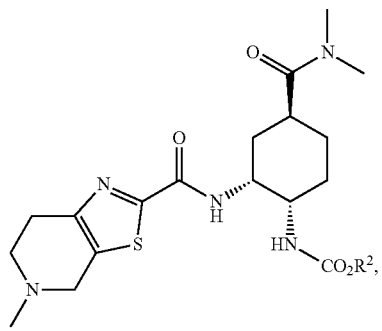 (9-A)

wherein
- R² is selected from the group consisting of an aliphatic group, substituted aliphatic group, aryl, substituted aryl, arylalkyl, and substituted arylalkyl; wherein the aliphatic group is an alkyl group selected from the group consisting of methyl, ethyl, n-propyl, iso-propyl, n-butyl, t-butyl, sec-butyl, hexanyl, 2-methyl-2-hexanyl, cyclohexyl, 1-methylcyclohexyl, cyclopropylmethyl, and isomers of n-pentyl, n-hexyl, n-heptyl, and n-octyl; and
- wherein substituted refers to the replacement of one or more hydrogen atoms with a substituent selected from the group consisting of R''', OR'', NR''R'', SR'', halogen, SiR'''R'''R''', OCOR''', COR'', CO₂R'', CONR''R'', NR''CO₂R''', NR''COR''', SOR''', SO₂R''', CN, NO₂ and CF₃;
- R'' is selected, independently, from the group consisting of hydrogen, an aliphatic group, aryl and arylalkyl; and
- R''' is selected, independently, from the group consisting of an aliphatic group, aryl and arylalkyl.

2. The compound of claim 1, wherein R² is an aliphatic group or a substituted aliphatic group.

3. The compound of claim 2, selected from the group consisting of:

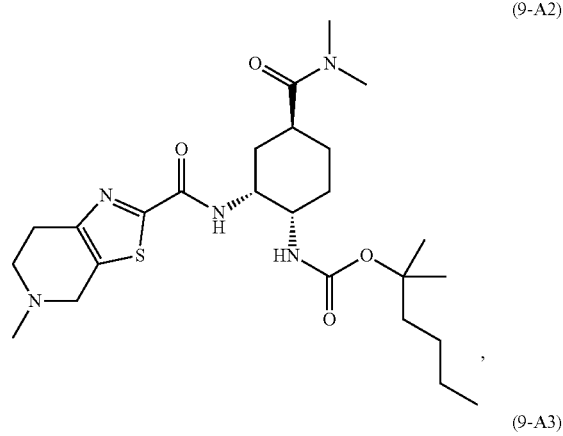 (9-A2)

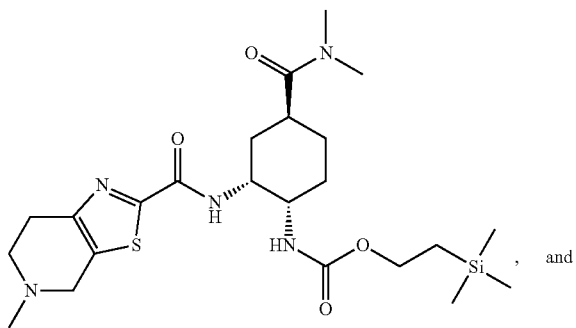 (9-A3)

and

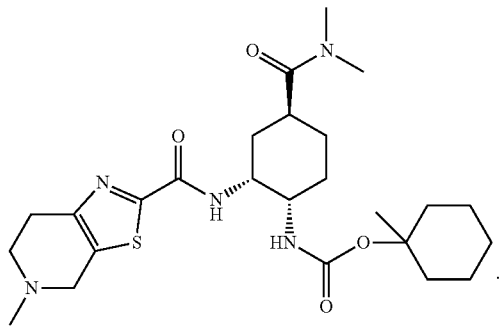 (9-A4)

* * * * *